US005981138A

United States Patent [19]

Suzuki et al.

[11] Patent Number: 5,981,138

[45] Date of Patent: Nov. 9, 1999

[54] HYDRAZINE COMPOUND AND SILVER HALIDE PHOTOGRAPHIC LIGHT-SENSITIVE MATERIAL USING THE SAME

[75] Inventors: Hiroyuki Suzuki; Kohzaburoh Yamada; Hiroshi Takeuchi; Toshihide Ezoe; Takashi Hoshimiya, all of Kanagawa, Japan

[73] Assignee: Fuji Photo Film Co., Ltd., Kanagawa, Japan

[21] Appl. No.: 08/923,417

[22] Filed: Sep. 4, 1997

[30] Foreign Application Priority Data

Sep. 4, 1996 [JP] Japan .................................... 8-234544

[51] Int. Cl.$^6$ .......................... G03C 1/06; C07D 213/42; C07D 213/70; C07D 235/06

[52] U.S. Cl. .......................... 430/264; 430/598; 430/505; 430/605; 564/310; 564/81; 564/148

[58] Field of Search .................................... 430/264, 598, 430/505, 605; 564/310, 81, 148

[56] References Cited

U.S. PATENT DOCUMENTS

| | | | |
|---|---|---|---|
| 4,994,365 | 2/1991 | Looker et al. | 430/598 |
| 5,126,227 | 6/1992 | Machonkin et al. | 430/264 |
| 5,288,590 | 2/1994 | Kuwabara et al. | 430/264 |
| 5,316,890 | 5/1994 | Okamura et al. | 430/264 |
| 5,439,776 | 8/1995 | Pilot et al. | 430/264 |
| 5,451,486 | 9/1995 | Pilot et al. | 430/264 |
| 5,550,003 | 8/1996 | Inoue | 430/264 |
| 5,589,323 | 12/1996 | Adkins et al. | 430/492 |
| 5,667,936 | 9/1997 | Yamada et al. | 430/264 |
| 5,688,630 | 11/1997 | Yamada et al. | 430/264 |
| 5,691,107 | 11/1997 | Kaneko et al. | 430/264 |
| 5,744,279 | 4/1998 | Ezoe et al. | 430/264 |

FOREIGN PATENT DOCUMENTS

A1 736798 10/1996 European Pat. Off. .......... G03C 1/06

*Primary Examiner*—Mark F. Huff
*Attorney, Agent, or Firm*—Sughrue, Mion, Zinn, Macpeak & Seas, PLLC

[57] ABSTRACT

A hydrazine compound represented by the following formula (I):

$$Ar_1—NH—NH—G_1—R_1 \quad (I)$$

wherein $Ar_1$ represents an aromatic group; $G_1$ represents a carbonyl group, a sulfonyl group, a sulfoxy group, a phosphoryl group, an oxalyl group or an iminomethylene group; $R_1$ represents a hydrogen atom or a block group; and at least one of $Ar_1$ and $R_1$ has a group represented by the following formula (II):

(II)

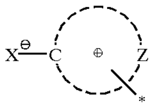

wherein * represents a bond for connecting directly or through a liking group to $Ar_1$ or $R_1$; Z represents a nonmetallic atom group capable of forming a 5- or 6-membered unsaturated heterocyclic ring having a conjugated positive charge; and $X^-$ represents —$O^-$, —$S^-$ or —$N^-$—$R_2$, wherein $R_2$ represents an alkyl group, an alkenyl group, an alkynyl group, an aryl group or a heterocyclic group. Also disclosed is a silver halide photographic light-sensitive material containing the hydrazine compound.

8 Claims, No Drawings

HYDRAZINE COMPOUND AND SILVER HALIDE PHOTOGRAPHIC LIGHT-SENSITIVE MATERIAL USING THE SAME

FIELD OF THE INVENTION

The present invention relates to a negative or direct positive silver halide photographic light-sensitive material containing a hydrazine compound having a specific structure.

BACKGROUND OF THE INVENTION

In the field of graphic arts, in order to obtain good reproduction of a halftone image in continuous gradation or good reproduction of a line work, a system of showing ultrahigh contrast (particularly, having γ of 10 or more) photographic properties is necessary. An image formation system capable of obtaining ultrahigh contrast photographic properties by the development with a processing solution having good storage stability has been demanded and to cope with this demand, as described in U.S. Pat. Nos. 4,166,742, 4,168,977, 4,221,857, 4,224,401, 4,243,739, 4,272,606 and 4,311,781, a system of forming an ultrahigh contrast negative image having a γ value exceeding 10 has been proposed, where a surface latent image type silver halide photographic light-sensitive material having added thereto a specific acylhydrazine compound is processed with a developer containing 0.15 mol/l or more of a sulfurous acid preservative and having a pH of from 11.0 to 12.3. This new system is characterized in that silver iodobromide or silver chloroiodobromide can be used, though only silver chlorobromide having a high silver chloride content can be used in conventional ultrahigh image-formation systems. Further, the new system is characterized in that a large amount of sulfurous acid preservative can be contained and relatively good storage stability is achieved, though conventional lith developers allow use of a very small amount of sulfurous acid preservative. However, developers having a pH of 11 or more are prone to air oxidation and unstable and cannot endure use or storage over a long period of time. A design for developing a silver halide light-sensitive material containing a hydrazine compound with a developer having a lower pH and forming a high contrast image is being attempted. JP-A-1-179939 (the term "JP-A" as used herein means an "unexamined published Japanese patent application") and JP-A-1-179940 describe a method of using a light-sensitive material containing a nucleation development accelerator having an adsorptive group to a silver halide emulsion grain and a nucleating agent having the same adsorptive group, with a developer at a pH of 11.0 or less. However, the emulsion used in these inventions is a silver bromide or silver chlorobromide emulsion and fails to reach a satisfactory level in view of stability because the photographic properties greatly change along the progress of development or due to fluctuation in the composition of the processing solution.

U.S. Pat. Nos. 4,998,604, 4,994,365 and 4,975,354 disclose a hydrazine compound having a repeating unit of ethylene oxide or a hydrazine compound having a pyridinium group. However, seeing from the description in the Examples of these patents, the high contrast level is not satisfactory and it is difficult to achieve high contrast and necessary Dmax under practical development processing conditions. Further, the nucleation high contrast light-sensitive material using a hydrazine derivative is large in the variation width of the photographic properties ascribable to the change in the pH of the developer. The pH of the developer greatly changes, for example, by the increase due to air oxidation of the developer or thickening of the developer resulting from evaporation of water or by the decrease due to absorption of carbon dioxide in air. Accordingly, a design to reduce the dependency of the photographic properties on the pH of the developer is being attempted.

A dot-to-dot working light-sensitive material which is generally handled in a bright room predominates in the field of light-sensitive materials for photomechanical process. In this field, the reprinted letter is required to have high quality such that lean Chinese letters can be reproduced. Accordingly, development of nucleating agents having higher activity is being demanded. In particular, the bright room light-sensitive materials having sensitivity sufficiently low to allow handling even in a bright room are difficult of giving high contrast by the nucleating agent and therefore, development of nucleating agents having yet higher activity is being demanded.

To achieve these objects, for example, highly active hydrazine-base nucleating agents disclosed in JP-A-6-148828, JP-A-6-180477 and JP-A-6-194774 have been developed.

The nucleating agent having as an acyl group a substituted alkyl group substituted by at least one electron withdrawing group is particularly excellent because extremely high contrast photographic property can be obtained even with a developer having a pH of 11 or less and also changes in the photographic capability due to fatigue of the developer is small. However, in some cases, the nucleating agent itself is readily oxidized and the storability is in need of much improvement.

As the nucleating agent having an adsorption accelerating group, highly active hydrazine-base nucleating agents disclosed in JP-A-63-234244, JP-A-63-234245, JP-A-6-148828, JP-A-6-180477 and JP-A-6-194774 are already known, however, the nucleating agent itself is readily oxidized and many compounds need be improved in view of the storability. Further, yet higher activity is required for obtaining desired dot quality.

On the other hand, a method of obtaining a direct positive image by surface developing an internal latent image-type silver halide photographic emulsion in the presence of a nucleating agent and a photographic emulsion or light-sensitive material for use in the method are known, for example, in U.S. Pat. Nos. 2,456,953, 2,497,875, 2,497,876, 2,588,982, 2,592,250, 2,675,318, 3,227,552 and 3,317,322, British Patents 1,011,062, 1,151,363, 1,269,640 and 2,011,391, JP-B-43-19405 (the term "JP-B" as used herein means an "examined Japanese patent publication[|P]'), JP-B-49-38164, JP-A-53-16623, JP-A-53-137133, JP-A-54-37732, JP-A-54-40629, JP-A-54-74536, JP-A-54-74729, JP-A-55-52055 and JP-A-55-90940.

In the above-described method for obtaining a direct positive image, a nucleating agent may be added to the developer, however, a method of adding the nucleating agent to a photographic emulsion layer or other appropriate layer of a light-sensitive material is more commonly used.

As the nucleating agent added to a direct positive silver halide light-sensitive material, hydrazine compounds are most well known and specific examples thereof include those described in *Research Disclosure*, No. 23510 (November, 1953), *ibid.*, No. 15162, Vol. 151 (November, 1976), *ibid.*, No. 17626, Vol. 176 (December, 1978). In general, the hydrazine-base nucleating agent provides large difference between the maximum density (Dmax) and the minimum density (Dmin) and is most excellent in the point of discrimination, however, it is deficient in that a high pH (11 or more) is required in the processing and improvement in this point has been demanded.

SUMMARY OF THE INVENTION

Accordingly, an object of the present invention is to provide a novel hydrazine compound.

Another object of the present invention is to provide a silver halide photographic light-sensitive material capable of obtaining extremely high contrast photographic characteristics having a γ value exceeding 10 using a stable developer.

A further other object of the present invention is to provide a silver halide photographic light-sensitive material for plate making, having high processing stability and excellent storability.

A still other object of the present invention is to provide a direct positive light-sensitive material capable of exhibiting sufficiently high reversibility even with a small addition amount of a processing solution having a low pH.

Other objects and effects of the present invention will be apparent from the following description.

These objects of the present invention have been achieved by providing:

a hydrazine compound represented by the following formula (I):

$$Ar_1—NH—NH—G_1—R_1 \quad (I)$$

wherein $Ar_1$ represents an aromatic group; $G_1$ represents a carbonyl group, a sulfonyl group, a sulfoxy group, a phosphoryl group, an oxalyl group or an iminomethylene group; $R_1$ represents a hydrogen atom or a block group; and at least one of $Ar_1$ and $R_1$ has a group represented by the following formula (II):

(II)

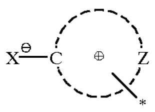

wherein * represents a bond for connecting directly or through a liking group to $Ar_1$ or $R_1$; Z represents a nonmetallic atom group capable of forming a 5- or 6-membered unsaturated heterocyclic ring having a conjugated positive charge; and $X^-$ represents —$O^-$, —$S^-$ or —$N^-$—$R_2$, wherein $R_2$ represents an alkyl group, an alkenyl group, an alkynyl group, an aryl group or a heterocyclic group; and a silver halide photographic light-sensitive material comprising the hydrazine compound.

DETAILED DESCRIPTION OF THE INVENTION

The compound represented by formula (I) is described in detail below.

In the compound represented by formula (I) of the present invention, $Ar_1$ represents an aromatic group, specifically, a substituted or unsubstituted phenyl, naphthyl or unsaturated heterocyclic group. The unsaturated heterocyclic group is a 5- or 6-membered heterocyclic group containing one or more of an oxygen atom, a nitrogen atom and a sulfur atom. Examples of the heterocyclic ring corresponds to the heterocyclic group represented by $Ar_1$ include include a pyridine ring, an imidazole ring, a triazine ring, a pyrimidine ring, a thiazole ring, a thiadiazole ring, an oxazole ring, a quinoline ring, an isoquinoline ring, a benzothiazole ring, a pyrazole ring and a benzimidazole ring.

The group represented by $Ar_1$ in formula (I) is preferably a substituted phenyl group and examples of the substituent include the following groups.

The substituent of $Ar_1$ includes a halogen atom and substituents bonding to $Ar_1$ at a carbon atom, an oxygen atom, a nitrogen atom or a sulfur atom thereof. Examples of the substituent bonded at a carbon atom thereof include an alkyl group, an alkenyl group, an alkynyl group, an aryl group, a carbamoyl group, an alkoxycarbonyl group, an aryloxycarbonyl group, an acyl group, a carboxy group, a cyano group and a heterocyclic group. Examples of the substituent bonded at an oxygen atom thereof include a hydroxy group, an alkoxy group, an aryloxy group, a heterocyclic oxy group, an acyloxy group, a carbamoyloxy group and a sulfonyloxy group. Examples of the substituent bonded at a nitrogen atom thereof include an acylamino group, an amino group, an alkylamino group, an arylamino group, a heterocyclic amino group, a ureido group, a sulfamoylamino group, an alkoxycabonylamino group, an aryloxycarbonylamino group, a sulfonamido group, an imido group and a heterocyclic group. Examples of the substituted bonded at a sulfur atom thereof include a mercapto group, an alkylthio group, an arylthio group, a heterocyclic thio group, a sulfamoyl group, an alkoxysulfonyl group, an aryloxysulfonyl group, a sulfonyl group, a sulfo group and a sulfinyl group. The substituent may further be substituted by these substituents.

The substituent is described in more detail below. Examples of the halogen atom include a fluorine atom, a chlorine atom and a bromine atom. The alkyl group is a linear, branched or cyclic alkyl group having from 1 to 16, preferably from 1 to 10, carbon atoms, and examples thereof include methyl, ethyl, isopropyl, t-butyl, benzyl and cyclopentyl. The alkenyl group is an alkenyl group having from 2 to 16 carbon atoms, and examples thereof include vinyl, 1-propenyl, 1-hexenyl and styryl. The alkynyl group is an alkynyl group having from 2 to 16 carbon atoms, and examples thereof include ethynyl, 1-butynyl, 1-dodecenyl and phenylethynyl. The aryl group is an aryl group having from 6 to 24 carbon atoms, and examples thereof include phenyl, naphthyl and p-methoxyphenyl.

The carbamoyl group is a carbamoyl group having from 1 to 18 carbon atoms, and examples thereof include carbamoyl, N-ethylcarbamoyl, N-octylcarbamoyl and N-phenylcarbamoyl. The alkoxycarbonyl group is an alkoxycarbonyl group having from 2 to 18 carbon atoms, and examples thereof include methoxycarbonyl and benzyloxycarbonyl. The aryloxycarbonyl group is an aryloxycarbonyl group having from 7 to 18 carbon atoms, and examples thereof include phenoxycarbonyl. The acyl group is an acyl group having from 1 to 18 carbon atoms, and examples thereof include acetyl and benzoyl. The heterocyclic group linked at a carbon atom on the ring is a 5- or 6-membered, saturated or unsaturated heterocyclic ring having from 1 to 5 carbon atoms and containing one or more of an oxygen atom, a nitrogen atom and a sulfur atom, in which the number of hetero atoms and the kind of elements constituting the ring may be either single or plural, and examples thereof include 2-furyl, 2-thienyl, 2-pyridyl and 2-imidazolyl.

The alkoxy group is an alkoxy group having from 1 to 16, preferably from 1 to 10, carbon atoms, and examples thereof include methoxy, 2-methoxyethoxy and 2-methanesulfonylethoxy. The aryloxy group is an aryloxy group having from 6 to 24 carbon atoms, and examples thereof include phenoxy, p-methoxyphenoxy and m-(3-hydroxypropionamido)phenoxy. The heterocyclic oxy group is a 5- or 6-membered, saturated or unsaturated heterocyclic oxy group having from 1 to 5 carbon atoms and containing one or more of an oxygen atom, a nitrogen atom and a sulfur atom, in which the number of hetero atoms and the kind of elements constituting the ring may be either single or plural, and examples thereof include 1-phenyltetrazolyl-5-oxy, 2-tetrahydropyranyloxy and 2-pyridyloxy. The acyloxy group is an acyloxy group having from 1 to 16, preferably from 1 to 10, carbon atoms, and examples thereof include acetoxy, benzoyloxy and 4-hydroxybutanoyloxy. The carbamoyloxy group is a carbamoyloxy group having from 1 to 16, preferably from 1 to 10 carbon atoms, and examples thereof include N,N-dimethylcarbamoyloxy, N-hexylcarbamoyloxy and N-phenylcarbamoyloxy. The sulfonyloxy group is a sulfonyloxy group having from 1 to 16 carbon atoms, and examples thereof include methanesulfonyloxy and benzenesulfonyloxy.

The acylamino group is an acylamino group having from 1 to 16, preferably from 1 to 10 carbon atoms, and examples thereof include acetamido and p-chlorobenzoylamido. The alkylamino group is an alkylamino group having from 1 to 16, preferably from 1 to 10 carbon atoms, and examples thereof include N,N-dimethylamino and N-(2-hydroxyethyl) amino. The arylamino group is an arylamino group having from 6 to 24 carbon atoms, and examples thereof include anilino and N-methylanilino. The heterocyclic amino group is a 5- or 6-membered, saturated or unsaturated heterocyclic amino group having from 1 to 5 carbon atoms and containing one or more of an oxygen atom, a nitrogen atom and a sulfur atom, in which the number of hetero atoms and the kind of elements constituting the ring may be either single or plural, and examples thereof include 2-oxazolylamino, 2-tetrahydropyranylamino and 4-pyrimidylamino. The ureido group is a ureido group having from 1 to 16, preferably from 1 to 10, carbon atoms, and examples thereof include ureido, methylureido, N,N-diethylureido and 2-methanesulfonamidoethylureido.

The sulfamoylamino group is a sulfamylamino group having from 0 to 16, preferably from 0 to 10 carbon atoms, and examples thereof include methylsulfamoylamino and 2-methoxyethylsulfamoylamino. The alkoxycarbonylamino group is an alkoxycarbonylamino group having from 2 to 16, preferably from 2 to 10, carbon atoms, and examples thereof include methoxycarbonylamino. The aryloxycarbonylamino group is an aryloxycarbonylamino group having from 7 to 24 carbon atoms, and examples thereof include phenoxycarbonylamino and 2,6-dimethoxyphenoxycarbonylamino. The sulfonamido group is a sulfonamido group having from 1 to 16, preferably from 1 to 10, carbon atoms, and examples thereof include methanesulfonamido and p-toluenesulfonamido. The imido group is an imido group having from 4 to 16 carbon atoms, and examples thereof include N-succinimido and N-phthalimido. The heterocyclic group linking at a nitrogen atom on the ring is a 5- or 6-membered heterocyclic ring comprising a nitrogen atom and at least one of a carbon atom, an oxygen atom and a sulfur atom, and examples thereof include pyrrolidino, morpholino and imidazolino.

The alkylthio group is an alkylthio group having from 1 to 16, preferably from 1 to 10 carbon atoms, and examples thereof include methylthio and 2-phenoxyethylthio. The arylthio group is an arylthio group having from 6 to 24 carbon atoms, and examples thereof include phenylthio and 2-carboxyphenylthio. The heterocyclic thio group is a 5- or 6-membered, saturated or unsaturated heterocyclic thio group having from 1 to 5 carbon atoms and containing one or more of an oxygen atom, a nitrogen atom and a sulfur atom, in which the number of hetero atoms and the kind of elements constituting the ring may be either single or plural, and examples thereof include 2-benzothiazolylthio and 2-pyridylthio.

The sulfamoyl group is a sulfamoyl group having from 0 to 16, preferably from 0 to 10, carbon atoms, and examples thereof include sulfamoyl, methylsulfamoyl and phenylsulfamoyl. The alkoxysulfonyl group is an alkoxysulfonyl group having from 1 to 16, preferably from 1 to 10, carbon atoms, and examples thereof include methoxysulfonyl. The aryloxysulfonyl group is an aryloxysulfonyl group having from 6 to 24, preferably from 6 to 12, carbon atoms, and examples thereof include phenoxysulfonyl. The sulfonyl group is a sulfonyl group having from 1 to 16, preferably from 1 to 10, carbon atoms, and examples thereof include methanesulfonyl and benzenesulfonyl. The sulfinyl group is a sulfinyl group having from 1 to 16, preferably from 1 to 10, carbon atoms, and examples thereof include methanesulfinyl and benzenesulfinyl.

The substituent of $Ar_1$ is preferably a halogen atom, an alkyl group, an aryl group, a carbamoyl group, an alkoxycarbonyl group, an aryloxycarbonyl group, an acyl group, a cyano group, an alkoxy group, an aryloxy group, a carbamoyloxy group, an acylamino group, a ureido group, a sulfamoylamino group, an alkoxycarbonylamino group, a sulfonamido group, a sulfamoyl group or a sulfonyl group, more preferably an alkyl group, an aryl group, a carbamoyl group, an alkoxy group, an acylamino group, a ureido group, a sulfonamido group or a sulfamoyl group, and most preferably an acylamino group, a ureido group or a sulfonamido group.

$G_1$ in formula (I) represents a carbonyl group, an oxalyl group, a sulfonyl group, a phosphoryl group, a sulfoxy group or an iminomethylene group, preferably a carbonyl group or an oxalyl group, and more preferably a carbonyl group.

$R_1$ in formula (I) represents a block group, specifically, an alkyl group, an aralkyl group, an alkenyl group, an alkynyl group, an aryl group, a heterocyclic group, an alkoxy group, an aryloxy group, an amino group or a hydrazino group, and these groups each may be substituted.

Examples of the alkyl group include a methyl group, a trifluoromethyl group, a difluoromethyl group, a 2-carboxytetrafluoroethyl group, a methoxyethyl group, a phenoxymethyl group, a pyridiniomethyl group, a 3-hydroxypropyl group, a 3-methanesulfonamidopropyl group and a phenylsulfonylmethyl group. Examples of the aralkyl group include an o-hydroxybenzyl group and an o-aminobenzyl group. Examples of the alkenyl group include a vinyl group and a 2-ethoxycarbonylvinyl group. Examples of the alkynyl group include an ethynyl group and a 2-methoxycarbonylethynyl group. Examples of the aryl group include a 3,5-dichlorophenyl group, a 2-hydroxymethylphenyl group, a 2-carbamoylphenyl group, a 3,5-dichloro-2-hydroxymethylphenyl group, a 2-methanesulfonamidophenyl group, a 4-cyanophenyl group and a 3,4-dinitrophenyl group. Examples of the heterocyclic group include a 4-nitroindazolyl group, a 4-pyridyl group, a benzotriazol-5-yl group, a 3-(2-mercaptotetrazolyl) phenyl group, an N-methyl-4-pyridinio group, a morpholino group and a piperidino group. Examples of the alkoxy group include a methoxy group, a propoxy group and 2-hydroxyethoxy group. Examples of the aryloxy group include a phenoxy group and a 1-naphthyloxy group. Examples of the amino group include an amino group, a propylamino group, a dimethylamino group, a 2,2,6,6-tetramethylpiperidin-4-yl group, an anilino group, a 2-hydroxyanilino group, a 5-benzotriazolylamino group and a 1-benzyl-3-pyridinioamino group. Examples of the hydrazino group include a hydrazino group, a 2-phenylhydrazino group and a 4-benzenesulfonamidophenylhydrazino group.

When these groups have a substituent, examples of the substituent include those described above as the substituent of $Ar_1$ in formula (I). The total carbon number of the substituents is preferably from 0 to 12, more preferably from 0 to 8.

When $G_1$ in formula (I) represents a carbonyl group, $R_1$ is preferably a hydrogen atom, an alkyl group, an alkenyl group, an alkynyl group, an aryl group or a saturated or unsaturated heterocyclic group, more preferably a hydrogen atom, an alkyl group or an aryl group, and most preferably an alkyl group.

When $G_1$ in formula (I) represents an oxalyl group, $R_1$ is preferably an alkoxy group, an aryloxy group or an amino group, and more preferably a substituted amino group.

The linking group which may intervene between the group represented by formula (II) and the compound of formula (I) is —O—, —S—, —N($R_N$)— (wherein $R_N$ represents a hydrogen atom, an alkyl group or an aryl group), —CO—, —C(=S)—, —$SO_2$—, —SO—, —P(=O)—, an alkylene group, an arylene group or a group comprising a combination of these groups.

Specific examples of the group comprising a combination of the groups include —CON($R_N$)—, —$SO_2$N($R_N$)—, —COO—, —N($R_N$)CON($R_N$)—, —N($R_N$)CSN($R_N$)—, —N($R_N$)$SO_2$N($R_N$)—, —$SO_2$N($R_N$)CO—, —$SO_2$N($R_N$) CON($R_N$)—, —N($R_N$)COCON($R_N$)—, —CON($R_N$)CO—, —S—(alkylene group)—CONH—, —O—(alkylene group)—CONH—, —O—(alkylene group)—NHCO—, —N($R_N$)N($R_N$)CONH—, (—O—)$_2$P(=O)O— and —NHCO—(arylene group)—$SO_2$NH—. These groups each may be linked at either the left or right site.

The group represented by formula (II) is described in more detail below.

The unsaturated heterocyclic ring formed by Z and the carbon atom on which $X^-$ is substituted is a 5- or 6-membered unsaturated heterocyclic ring having a conjugate positive charge. The unsaturated heterocyclic ring having a conjugate positive charge includes rings having resonance structures. In the case of the 5-membered heterocyclic ring, for example, rings having resonance structures are represented as follows.

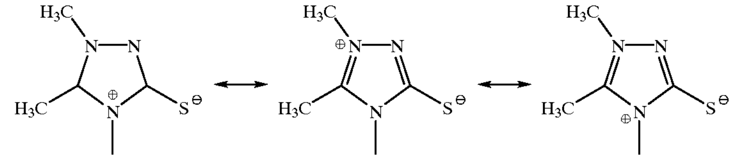

Examples of the unsaturated heterocyclic ring formed by Z and the carbon atom include imidazoliums, pyrazoliums, oxazoliums, thiazoliums, triazoliums, tetrazoliums, thiadiazoliums, oxadiazoliums, thiatriazoliums and oxatriazoliums, dithianiums, pyridaziniums, pyrimidiniums, triaziniums, tetraziniums, oxathianiums, thiaziniums, oxadiniums, oxadiaziniums and thiadiaziniums. The unsaturated heterocycric ring is preferably a 5-membered unsaturated heterocyclic ring, and particularly preferred are thiadiazoliums, oxadiazoliums and triazoliums.

The above described heterocyclic ring may be substituted by the substituents exemplified for $Ar_1$ in formula (I), and among those substituents, an alkyl group, an aryl group, an alkenyl group, an alkynyl group, a heterocyclic group, a carbamoyl group, a sulfamoyl group, an alkoxy group, an aryloxy group, an alkylamino group, an arylamino group, an alkylthio group and an arylthio group are preferred.

When $X^-$ is —$N^-R_2$, $R_2$ represents a substituted or unsubstituted alkyl group (e.g., methyl, ethyl, n-propyl, n-butyl, isopropyl, n-octyl, carboxyethyl, ethoxycarbonylmethyl, dimethylaminoethyl), a substituted or unsubstituted cycloalkyl group (e.g., cyclohexyl, 4-methylcyclohexyl, cyclopentyl), a substituted or unsubstituted alkenyl group (e.g., propenyl, 2-methylpropenyl), a substituted or unsubstituted alkynyl group (e.g., propargyl, butynyl, 1-methylpropargyl), a substituted or unsubstituted aralkyl group (e.g., benzyl, 4-methoxybenzyl), a substituted or unsubstituted aryl group (e.g., phenyl, naphthyl, 4-methylphenyl, 3-methoxyphenyl, 4-ethoxycarbonylphenyl) or a substituted or unsubstituted heterocyclic group (e.g., pyridyl, imidazolyl, morpholino, triazolyl, tetrazolyl, thienyl).

$X^-$ is most preferably —$S^-$.

Specific examples of the chemical formula of the group represented by formula (II) are set forth below, however, the present invention is by no means limited to these chemical formulae.

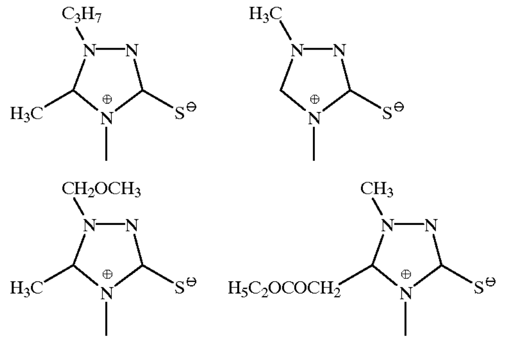

-continued
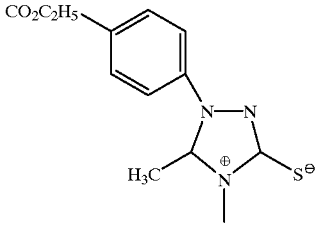
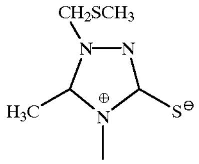
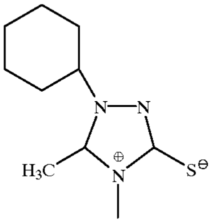
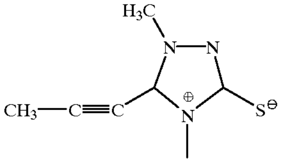
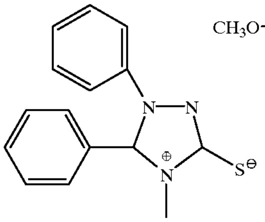
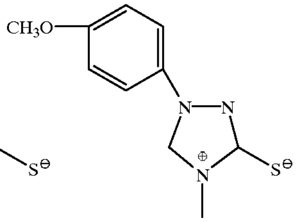
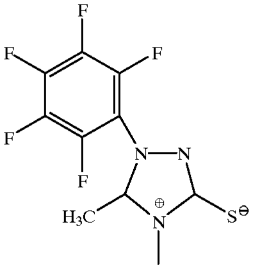
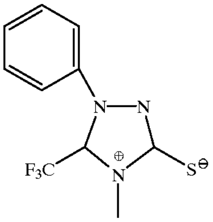
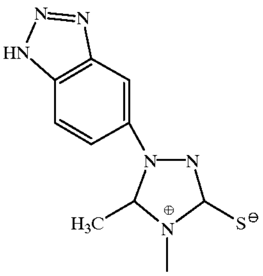
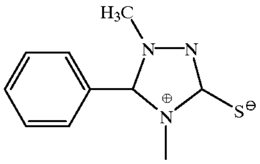
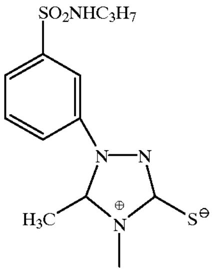
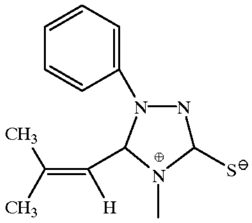
-continued
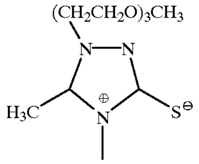
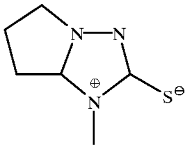
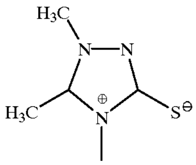
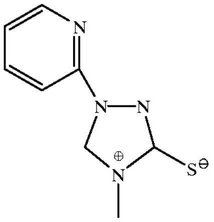
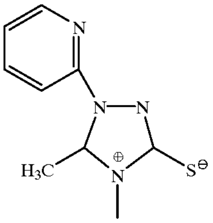
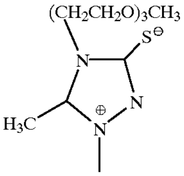
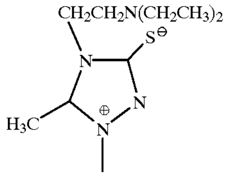
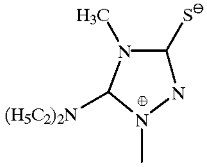
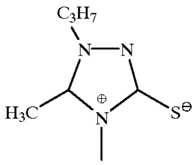
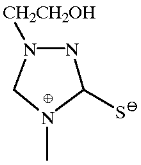
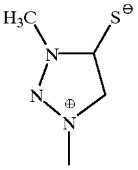
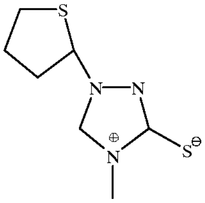
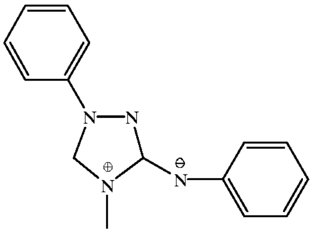
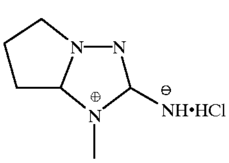
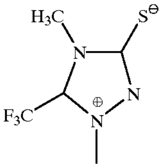

-continued
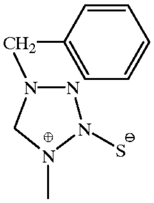
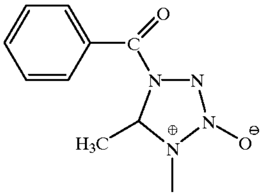
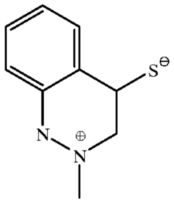
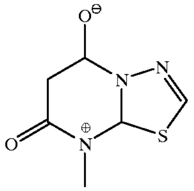
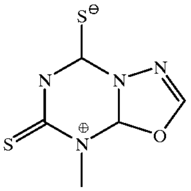
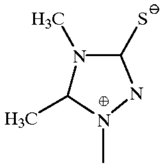
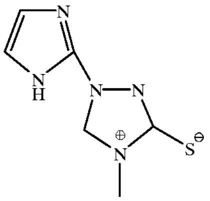
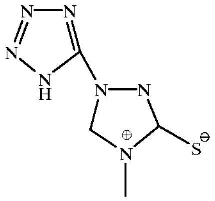
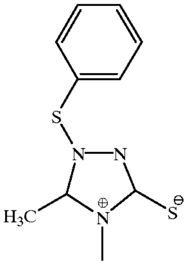
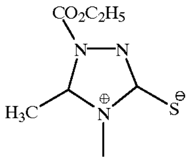
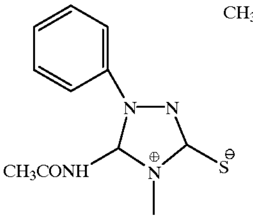
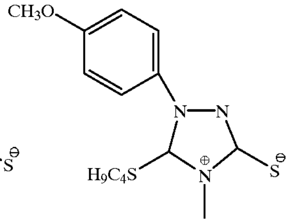
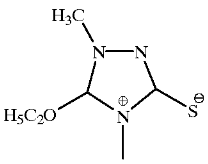
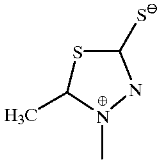
-continued
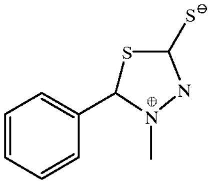
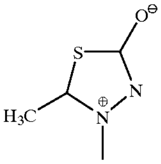
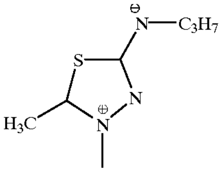
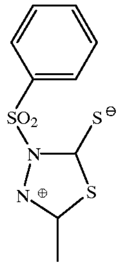
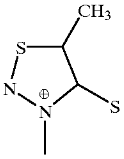
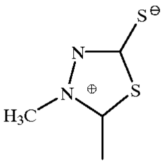
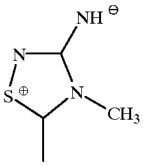
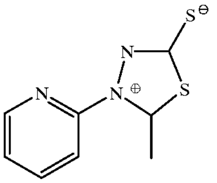
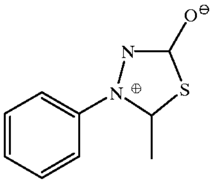
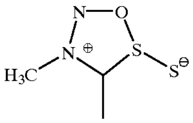
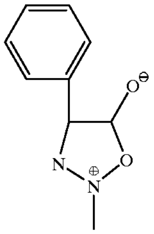
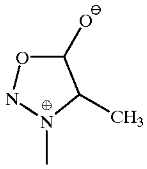
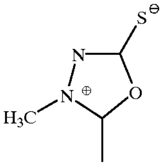
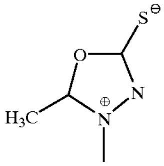
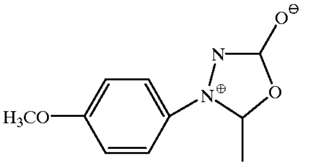

-continued

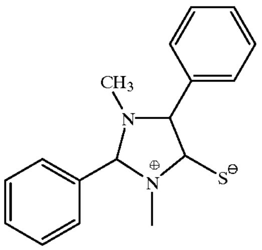

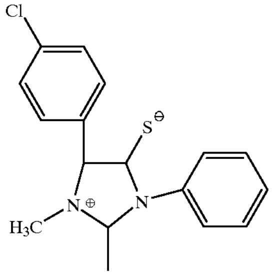

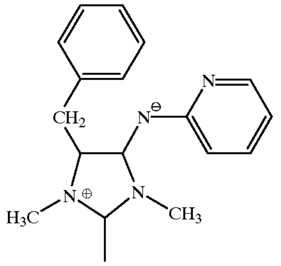

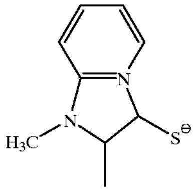

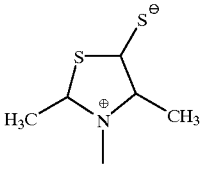

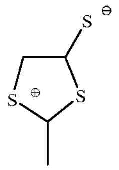

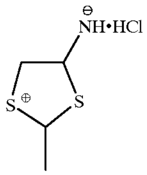

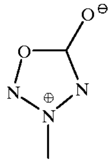

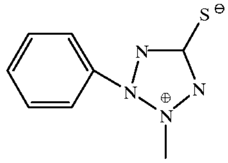

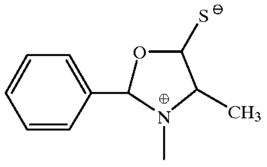

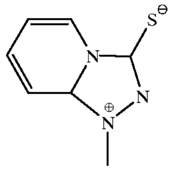

Among the compounds represented by formula (I), more preferred are the compounds represented by the following formulae (III-A) and (III-B):

(III-A)

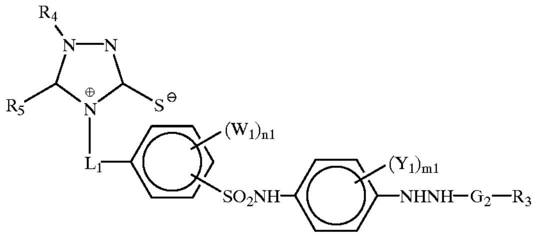

(III-B)

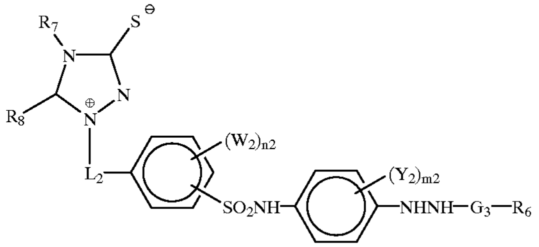

wherein $L_1$ and $L_2$ each represents a linking group and the linking group has the same definition as the linking group described above for the case where the group represented by formula (II) is bonded to $Ar_1$ or $R_1$ through a linking group in formula (I); $G_2$ and $G_3$ each has the same definition as $G_1$ in formula (I) and the preferred range is also the same; $R_3$ and $R_6$ each has the same definition as $R_1$ in formula (I) and the preferred range is also the same; $W_1$ and $W_2$ each has the same definition as the substituent described above for $Ar_1$ in formula (I) and the preferred range is also the same; $Y_1$ and $Y_2$ each represents a substituent and the substituent has the same definition as the substituent described for $Ar_1$, however, $Y_1$ and $Y_2$ each is preferably an alkyl group, a hydroxy group, an acylamino group, an alkoxy group, a sulfonamido group, a carboxy group, a sulfo group, a salt of these groups, an alkylthio group, a mercapto group, an acyloxy group or a halogen atom; $n_1$, $n_2$, $m_1$ and $m_2$ each represents an integer of from 0 to 4, preferably 0 or 1, and $m_1$ and $m_2$ each is more preferably 0; $R_4$ and $R_7$ each represents a substituent and the substituent is the same as the substituent described for Z in formula (II), of which preferred range is also the same; and $R_5$ and $R_8$ each represents a hydrogen atom or a substituent and when $R_5$ and $R_8$ each represents a substituent, the substituent is the same as the substituent described above for Z in formula (II) and the preferred range thereof is also the same.

Specific examples of the compound represented by formula (I) are set forth below, however, the present invention is by no means limited to these compounds.

TABLE 1
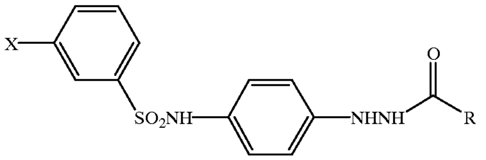
| X | R | | | |
|---|---|---|---|---|
| | —H | —$CF_3$ | —$CF_2H$ | —$C_2F_4CO_2H$ |
| 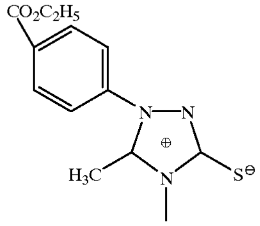 | 1 a | 1 b | 1 c | 1 d |
| 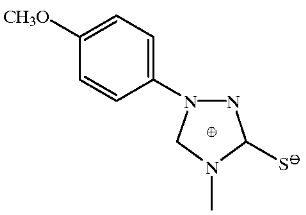 | 2 a | 2 b | 2 c | 2 d |
| 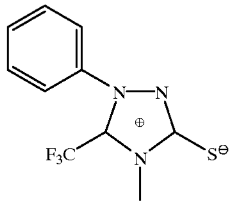 | 3 a | 3 b | 3 c | 3 d |
| 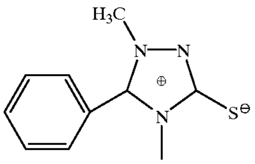 | 4 a | 4 b | 4 c | 4 d |
| 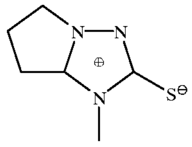 | 5 a | 5 b | 5 c | 5 d |
| 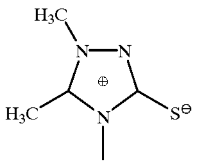 | 6 a | 6 b | 6 c | 6 d |

TABLE 1-continued
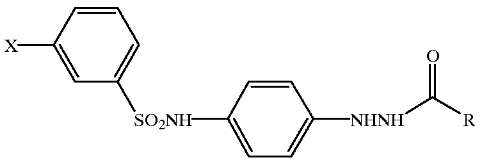
| X | R | | | |
|---|---|---|---|---|
| | —H | $—CF_3$ | $—CF_2H$ | $—C_2F_4CO_2H$ |
| 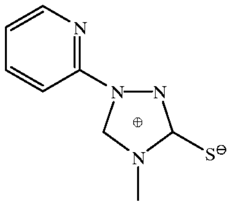 | 7 a | 7 b | 7 c | 7 d |
| 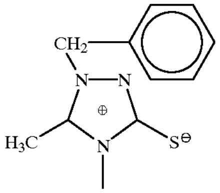 | 8 a | 8 b | 8 c | 8 d |
TABLE 2
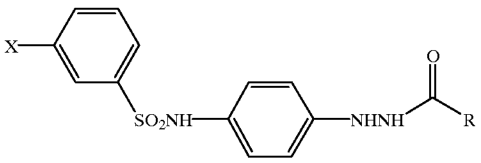
| X | R | | | |
|---|---|---|---|---|
| | —H | $—CF_3$ | $—CF_2H$ | $—C_2F_4CO_2H$ |
| 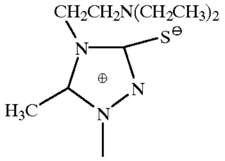 | 9 a | 9 b | 9 c | 9 d |
| 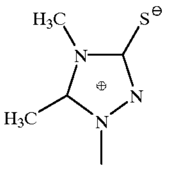 | 10 a | 10 b | 10 c | 10 d |
| 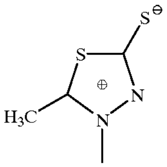 | 11 a | 11 b | 11 c | 11 d |

TABLE 2-continued
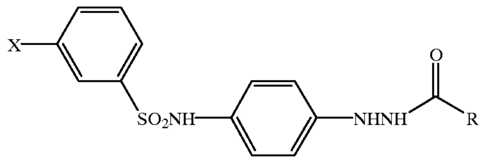
| | R | | | |
|---|---|---|---|---|
| X | —H | —$CF_3$ | —$CF_2H$ | —$C_2F_4CO_2H$ |
| 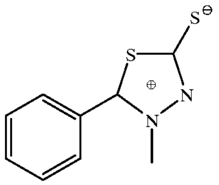 | 12 a | 12 b | 12 c | 12 d |
| 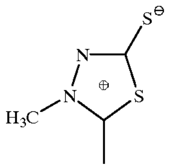 | 13 a | 13 b | 13 c | 13 d |
| 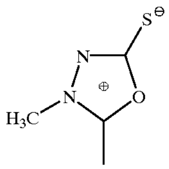 | 14 a | 14 b | 14 c | 14 d |
| 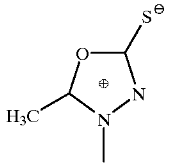 | 15 a | 15 b | 15 c | 15 d |

TABLE 3
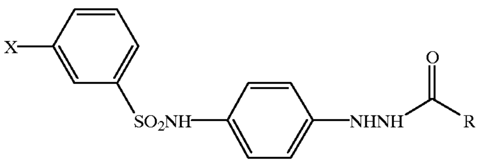
| X | R | | | | |
|---|---|---|---|---|---|
| | —CONHPh | —CONH $C_3H_7$ | —CONH $(CH_2)_2OH$ | 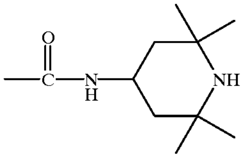 | 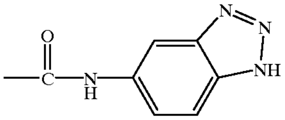 |
| 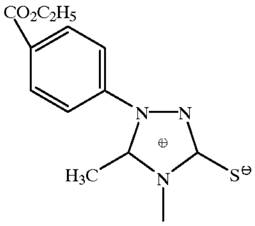 | 1 e | 1 f | 1 g | 1 h | 1 i |
| 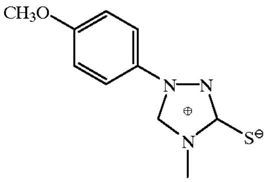 | 2 e | 2 f | 2 g | 2 h | 2 i |
| 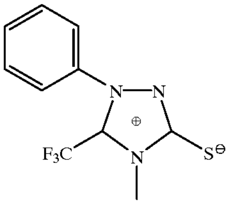 | 3 e | 3 f | 3 g | 3 h | 3 i |
| 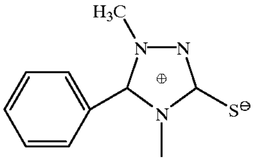 | 4 e | 4 f | 4 g | 4 h | 4 i |
| 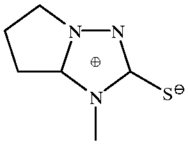 | 5 e | 5 f | 5 g | 5 h | 5 i |

TABLE 3-continued
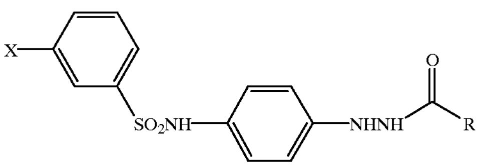
| | R | | | | |
|---|---|---|---|---|---|
| X | —CONHPh | —CONH $C_3H_7$ | —CONH $(CH_2)_2OH$ | 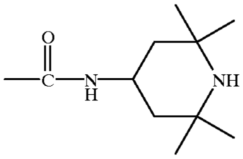 | 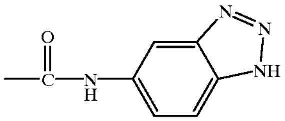 |
| 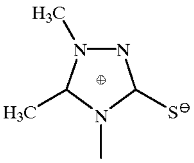 | 6 e | 6 f | 6 g | 6 h | 6 i |
| 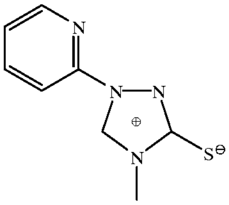 | 7 e | 7 f | 7 g | 7 h | 7 i |
| 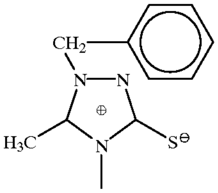 | 8 e | 8 f | 8 g | 8 h | 8 i |

TABLE 4
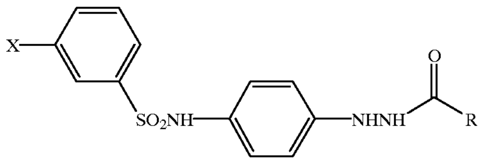
| X | R | | | | |
|---|---|---|---|---|---|
| | —CONHPh | —CONH $C_3H_7$ | —CONH $(CH_2)_2OH$ | 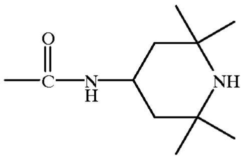 | 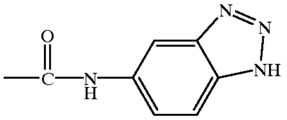 |
| 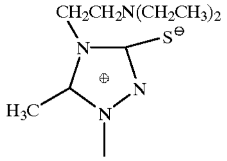 | 9 e | 9 f | 9 g | 9 h | 9 i |
| 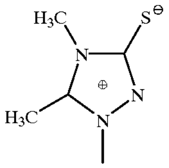 | 10 e | 10 f | 10 g | 10 h | 10 i |
| 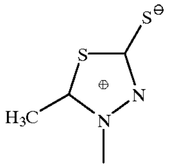 | 11 e | 11 f | 11 g | 11 h | 11 i |
| 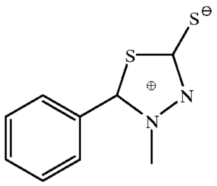 | 12 e | 12 f | 12 g | 12 h | 12 i |
| 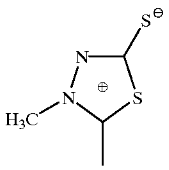 | 13 e | 13 f | 13 g | 13 h | 13 i |
| 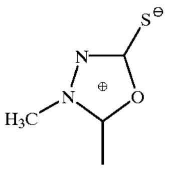 | 14 e | 14 f | 14 g | 14 h | 14 i |

TABLE 4-continued
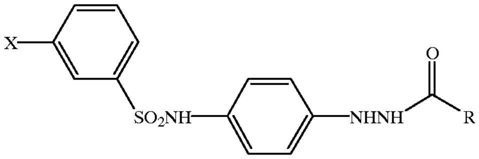
| X | R | | | | |
|---|---|---|---|---|---|
| | —CONHPh | —CONH $C_3H_7$ | —CONH $(CH_2)_2OH$ | 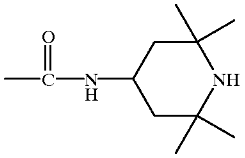 | 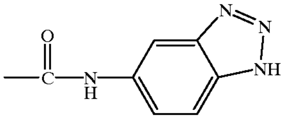 |
| 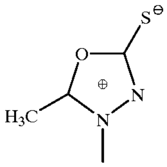 | 15 e | 15 f | 15 g | 15 h | 15 i |

TABLE 5
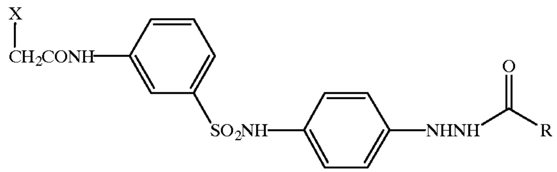
| X | R | | | | | | |
|---|---|---|---|---|---|---|---|
| | —H | $—CF_3$ | $—CF_2H$ | $—C_2F_4CO_2H$ | —CONHPh | 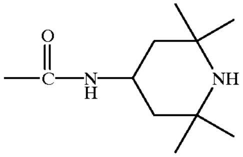 — | 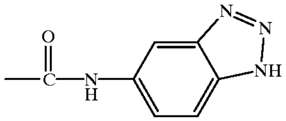 — |
| 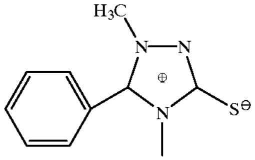 | 16 a | 16 b | 16 c | 16 d | 16 e | 16 f | 16 g |
| 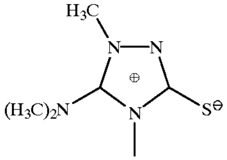 | 17 a | 17 b | 17 c | 17 d | 17 e | 17 f | 17 g |
| 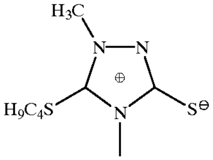 | 18 a | 18 b | 18 c | 18 d | 18 e | 18 f | 18 g |

TABLE 5-continued
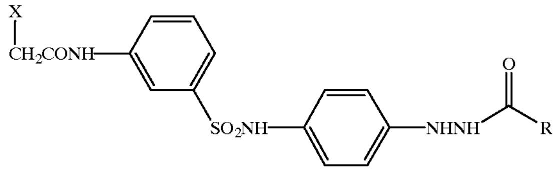
| X | R | | | | | | |
|---|---|---|---|---|---|---|---|
| | —H | —$CF_3$ | —$CF_2H$ | —$C_2F_4CO_2H$ | —CONHPh | 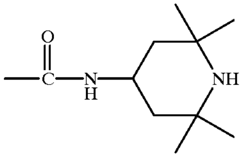 — | 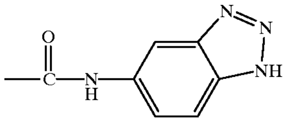 — |
| 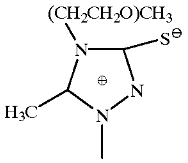 | 19 a | 19 b | 19 c | 19 d | 19 e | 19 f | 19 g |

TABLE 6
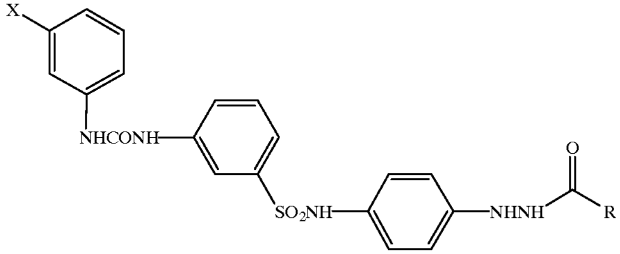
| X | R | | | | | | |
|---|---|---|---|---|---|---|---|
| X | —H | $—CF_3$ | $—CF_2H$ | $—C_2F_4CO_2H$ | —CONHPh | 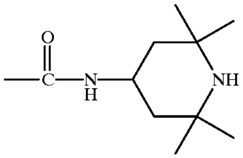 — | 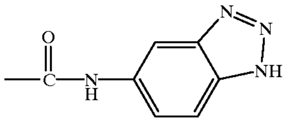 — |
| 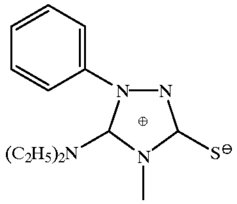 | 20 a | 20 b | 20 c | 20 d | 20 e | 20 f | 20 g |
| 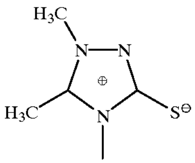 | 21 a | 21 b | 21 c | 20 d | 21 e | 21 f | 21 g |

TABLE 6-continued
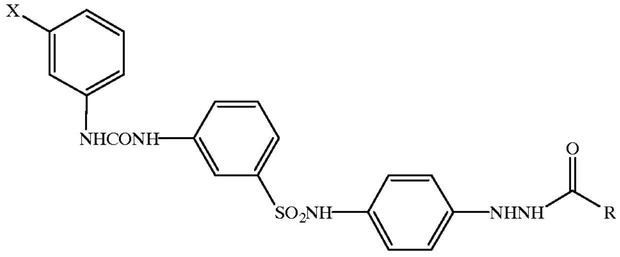
| X | R | | | | | | |
|---|---|---|---|---|---|---|---|
| | —H | —$CF_3$ | —$CF_2H$ | —$C_2F_4CO_2H$ | —CONHPh | 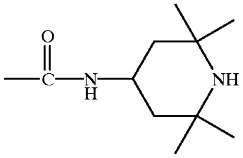 — | 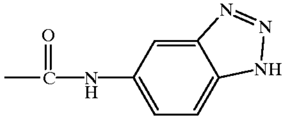 — |
| 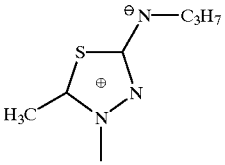 | 22 a | 22 b | 22 c | 22 d | 22 e | 22 f | 22 g |
| 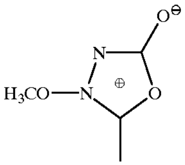 | 23 a | 23 b | 23 c | 23 d | 23 e | 23 f | 23 g |

TABLE 7
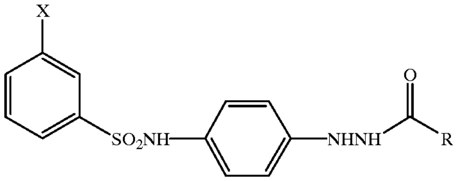
| X | R | | | | |
|---|---|---|---|---|---|
| | 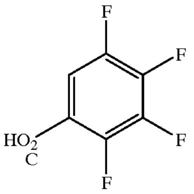 | 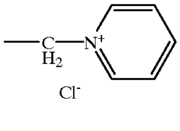 | 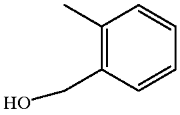 | $-C_3F_6CO_2H$ | 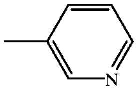 |
| 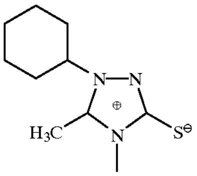 | 24 a | 24 b | 24 c | 24 d | 24 e |
TABLE 8
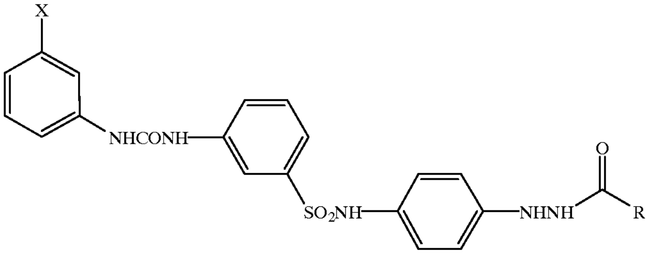
| X | R | | | |
|---|---|---|---|---|
| | 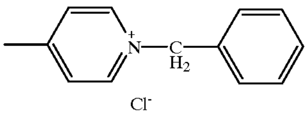 | 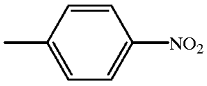 | 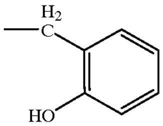 | 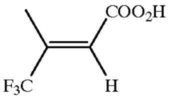 |
| 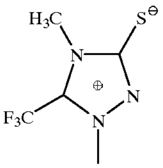 | 25 a | 25 b | 25 c | 25 d |

TABLE 9
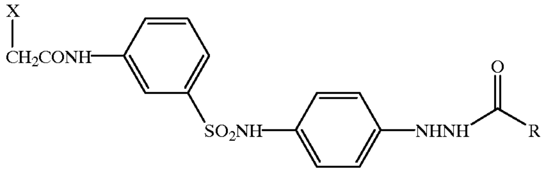
| | R | | | |
|---|---|---|---|---|
| X | 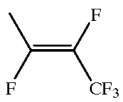 | —COOEt | 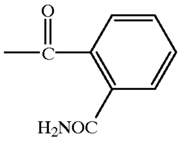 — | 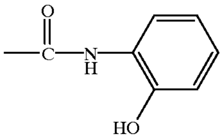 — |
| 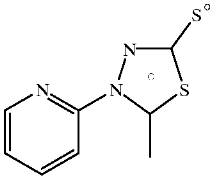 | 26 a | 26 b | 26 c | 26 d |
TABLE 10
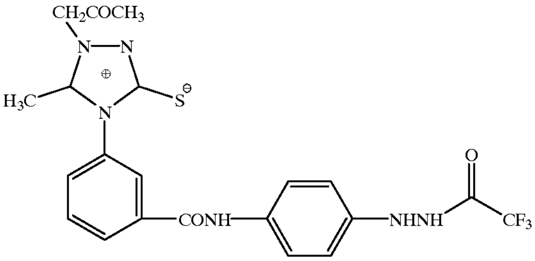
27
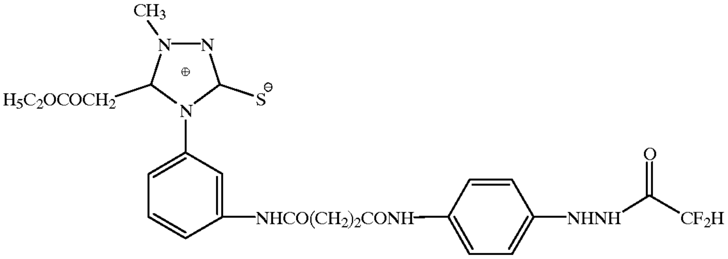
28
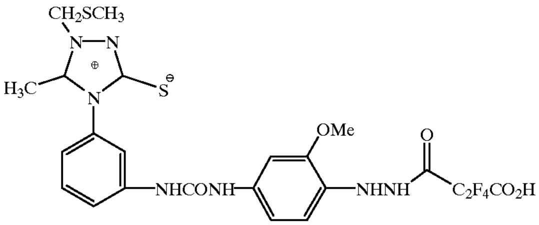
29

TABLE 10-continued
30
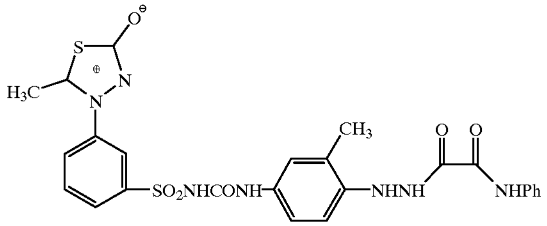
31
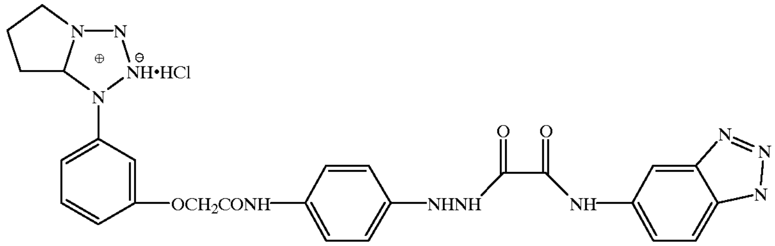
32
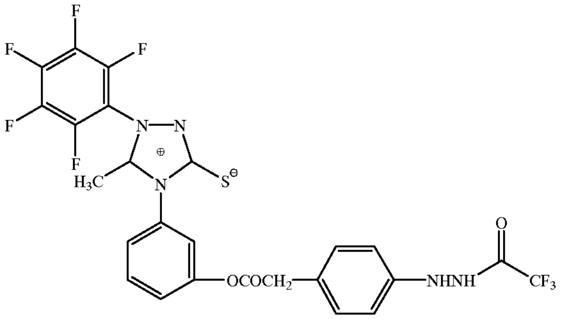
TABLE 11
33
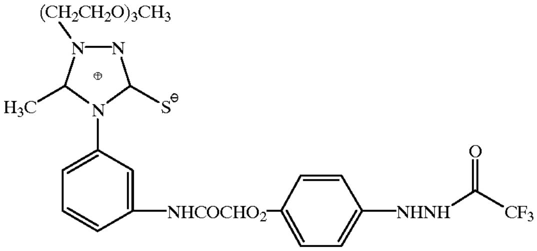
34
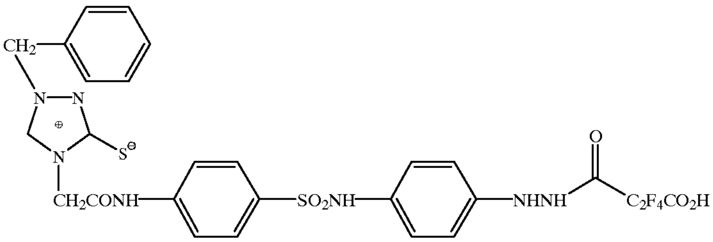

TABLE 11-continued
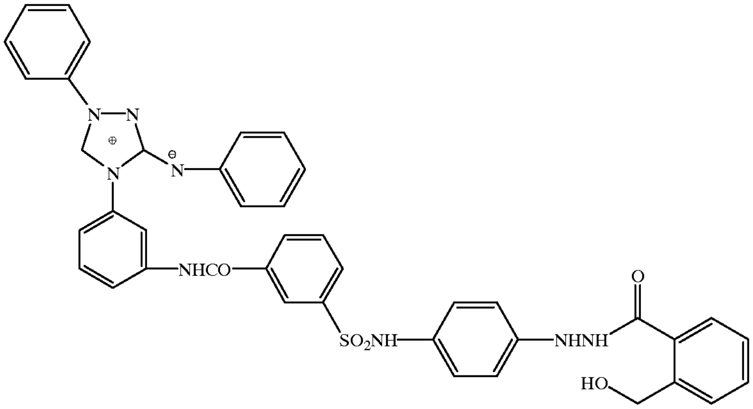
35
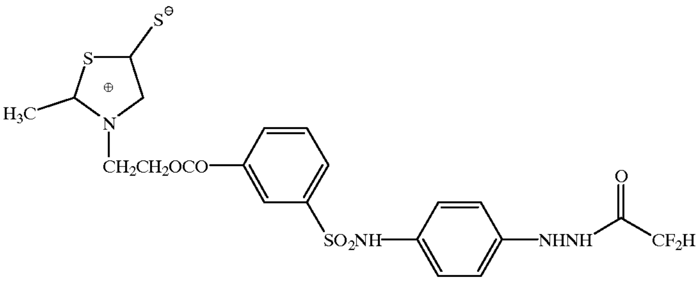
36
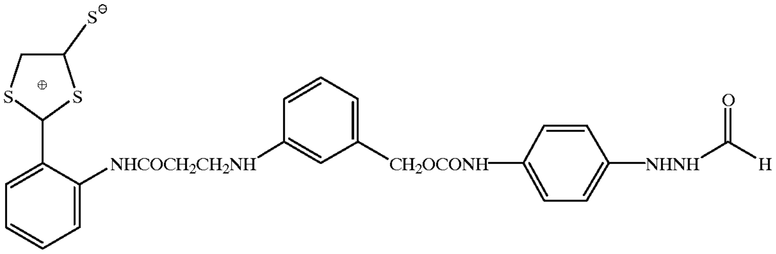
37
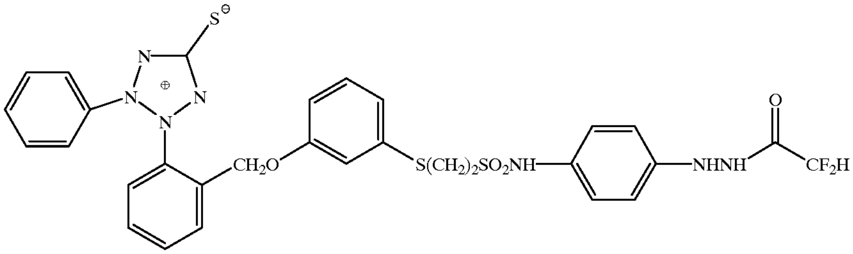
38

TABLE 12
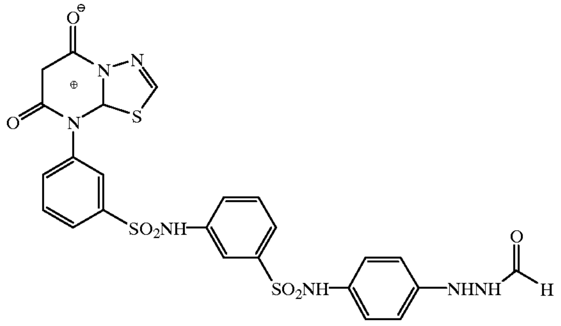
39
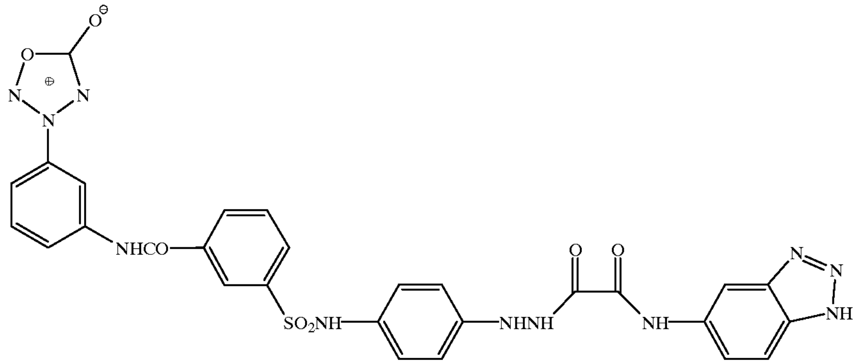
40

TABLE 13
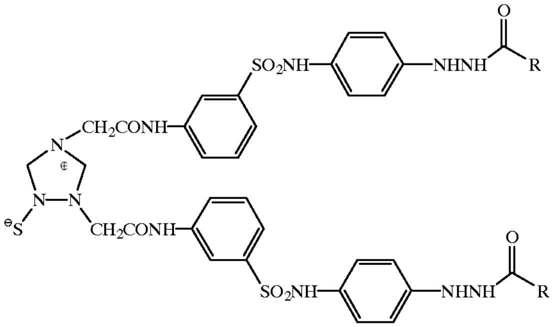
| R | —H | $—CF_2H$ | $—CF_3$ | $—C_2F_4CO_2H$ | 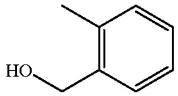 | —CONHPh | 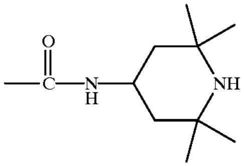 — | 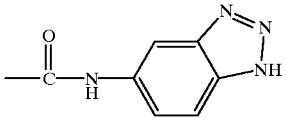 — |
|---|---|---|---|---|---|---|---|---|
| Compound No. | 41 a | 41 b | 41 c | 41 d | 41 e | 41 f | 41 g | 41 h |

The compound represented by formula (I) of the present invention can be synthesized by various known methods. An optimal synthesis method is selected depending on individual compounds and the synthesis method in general cannot be specified, however, several examples of useful synthesis routes are described below.

SYNTHESIS EXAMPLES

Synthesis of Compound 4a

Compound 4a was synthesized according to Scheme 1.

Synthesis of Compound 4a

To an acetonitrile 10 ml solution containing 1.9 g of Intermediate 2, 1 g of N-benzoyl-N-methylhydrazine was added in a nitrogen atmosphere, and the mixture was stirred at room temperature for 2 hours. After distilling off the solvent, 10 ml of methanol and 0.1 ml of triethylamine were added and then 0.1 g of SM-28 was added dropwise in a nitrogen atmosphere while heating at 50° C. After stirring the solution as it is for 2 hours, 0.1 ml of concentrated hydrochloric acid was added and the product material was extracted by adding an aqueous solution of saturated sodium chloride and ethyl acetate, then dried and concentrated to obtain 1.1 g of Compound 4a by column chromatography.

Scheme 1

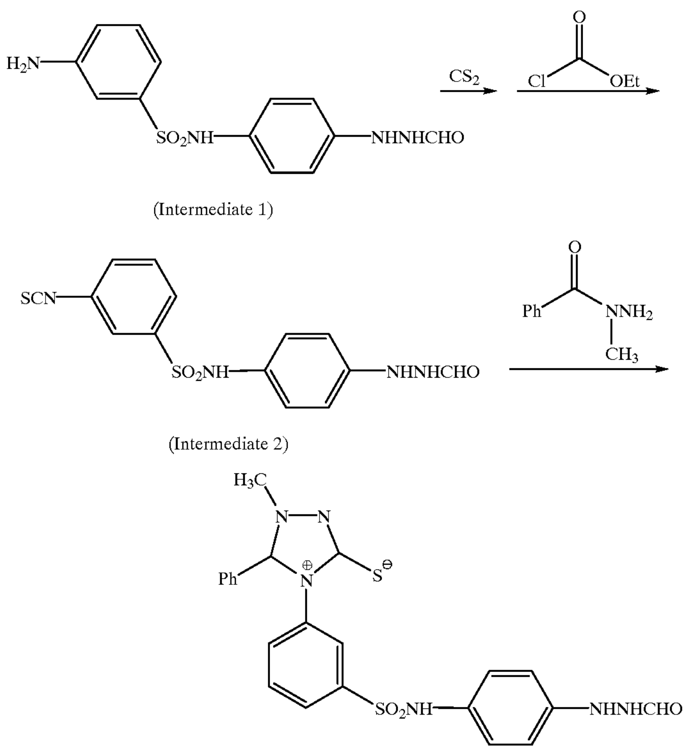

(Intermediate 1)

(Intermediate 2)

(Compound 4a)

Synthesis of Intermediate 1

N-p-aminophenyl-N'-formylhydrazine and m-nitrobenzenesulfonyl chloride were reacted and the N-m-nitrobenzenesulfonamidophenyl-N'-formylhydrazine obtained was iron reduced to prepare Intermediate 1.

Synthesis of Intermediate 2

To an acetonitrile 100 ml solution containing 18.4 g of Intermediate 1, 8.4 ml of triethylamine was added and then 5.4 ml of carbon disulfide was added dropwise, followed by stirring at 50° C. for 5 hours. The reaction solution was cooled to 10° C. or lower, 5.7 ml of ethyl chloroformate was added thereto, and the mixture was stirred at room temperature for 2 hours. The product material was extracted by adding diluted hydrochloric acid and ethyl acetate, then dried and concentrated to obtain 2.3 g of Intermediate 2 by color chromatography.

Synthesis of Compound 4b

Compound 4b was synthesized thoroughly in the same manner as Compound 4a except for using N-p-aminophenyl-N'-trifluoroacetylhydrazine in place of N-p-aminophenyl-N'-formylhydrazine in the synthesis of Compound 4a.

Synthesis of Compound 4d

Compound 4d was synthesized according to Scheme 2.

Scheme 2

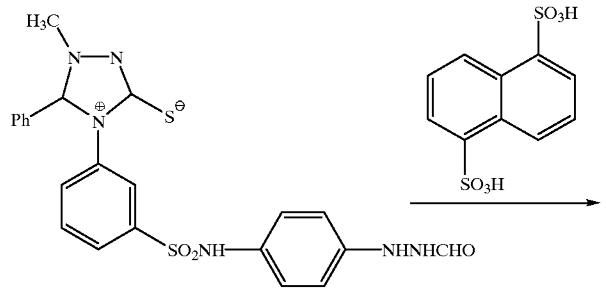

(Compound 4a)

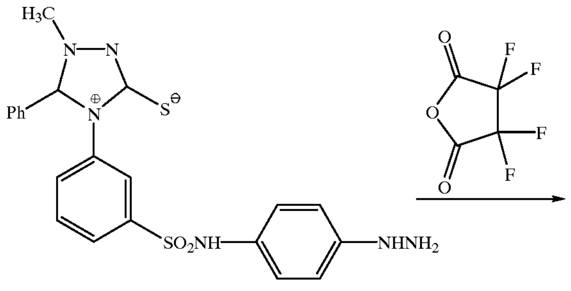

(Intermediate 3)

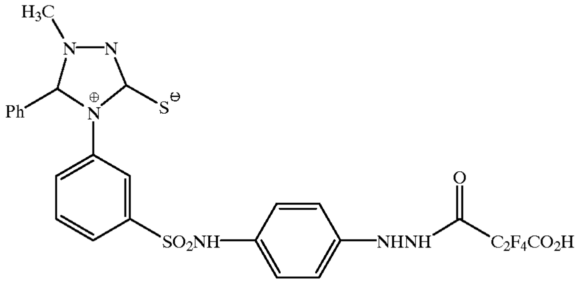

(Compound 4d)

Synthesis of Intermediate 3

7.5 g of Compound 4a and 300 ml of a methanol suspension containing 3 g of 1,5-naphthalenedisulfonic acid were heated in a nitrogen atmosphere and stirred at 50° C. for 3 hours. The product material was extracted by adding ethyl acetate and an aqueous solution of sodium hydrogencarbonate, then dried and concentrated to obtain 4.2 g of Intermediate 3.

Synthesis of Compound 4d 4.2 g of Intermediate 3 was formed into a mixed solution (100 ml) with dimethylimidazolidinone and acetonitrile, and thereto 20 ml of an acetonitrile solution containing 1.3 ml of tetrafluorosuccinic anhydride was added dropwise under cooling. After passing through the post processing operation, the solution was purified by column chromatography to obtain 3.8 g of Compound 4d (mp: 195 to 200° C.).

Synthesis of Compound 4h

After ice-cooling 100 ml of an acetonitrile solution containing 4.4 g of imidazole, 2.1 g of oxalyl chloride was added dropwise thereto. After stirring the mixture at room temperature for 1 hour, insoluble matters were separated by filtration and 1 g of 4-amino-2,2,6,6-tetramethylpiperidine was added dropwise to the filtrate at room temperature. To the resulting solution, 50 ml of an acetonitrile solution containing 8.1 g of Intermediate 3 was added dropwise and the mixture was stirred for 1 hour. The product material was extracted by adding ethyl acetate and diluted hydrochloric acid, then dried and concentrated to obtain 5.5 g of Compound 4h by silica gel column chromatography.

Synthesis of Compound 21a

Compound 21a was synthesized according to Scheme 3.

Scheme 3

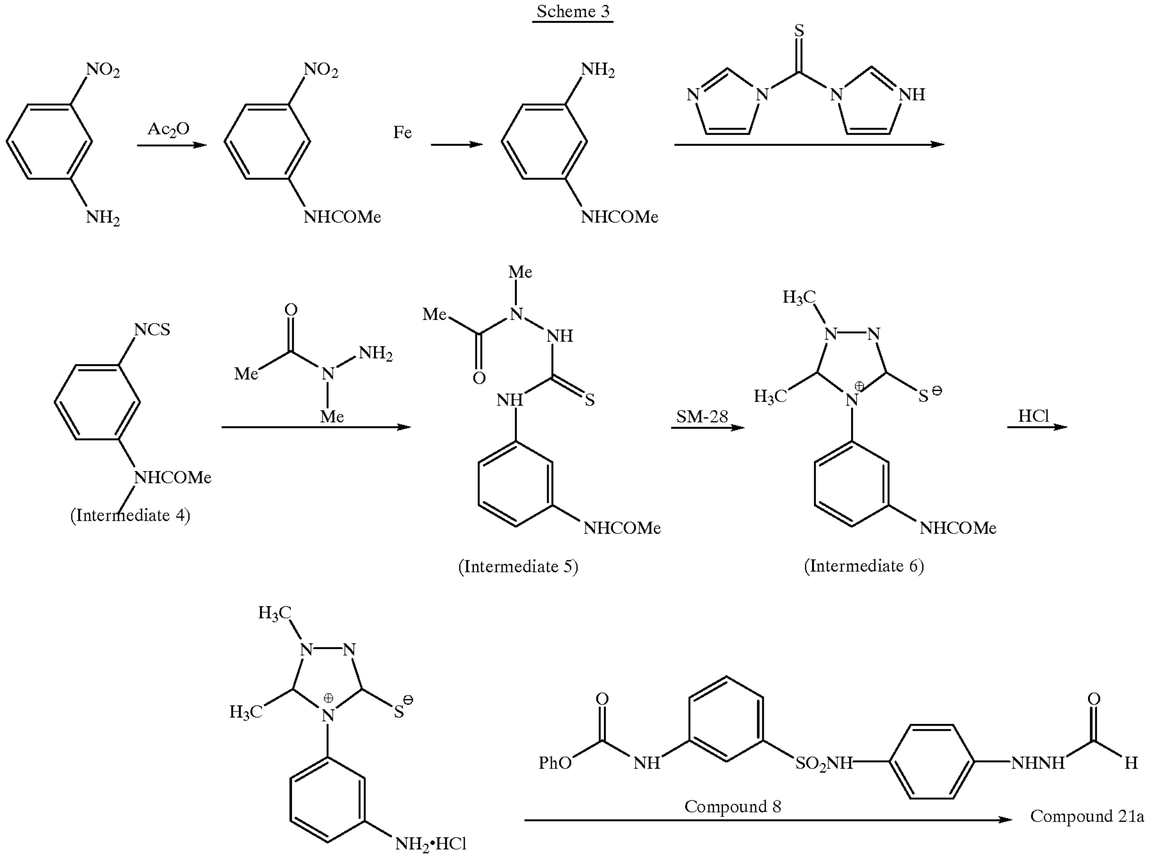

(Intermediate 4)

(Intermediate 5)

(Intermediate 6)

(Intermediate 7)

Synthesis of Intermediate 4

To a methanol 100 ml solution containing 6.5 g of m-aminoacetoanilide which was obtained by reacting acetic anhydride with m-aminonitrobenzene and iron-reducing the reaction product, 20 g of thiocarbonyldiimidazole was added at room temperature, and the mixture was stirred for 1 hour. The solids precipitated were separated by filtration to obtain 15.1 g of Intermediate 4.

Synthesis of Intermediate 5

To an acetonitrile 50 ml solution containing 8 g of Intermediate 4, an acetonitrile 10 ml solution containing 3.5 g of N-acetyl-N-methylhydrazine was added dropwise at room temperature. After stirring the mixed solution for 1 hour, the solids precipitated were separated by filtration and the filtrate was concentrated to obtain 11 g of Intermediate 5.

Synthesis of Intermediate 6

To a methanol 50 ml solution containing 10 g of Intermediate 5, 1 ml of SM-28 was added, and the mixed solution was stirred at 50° C. for 2 hours. The precipitate produced was separated by filtration and the filtrate was concentrated to obtain 7.5 g of Intermediate 6.

Synthesis of Intermediate 7

To 5 g of Intermediate 6, 70 ml of water and 70 ml of hydrochloric acid were added, and the mixed solution was stirred under heating at 90° C. for 2 hours. After distilling off the solvent, the residue was recrystallized from a mixed solvent of methanol and ethyl acetate to obtain 4 g of Intermediate 7.

Synthesis of Intermediate 21a

To 3.5 g of Intermediate 7, 5.4 g of Compound 8 and 4 g of imidazole, 20 ml of dimethylacetamide was added, and the mixed solution was stirred under heating at 60° C. for 2 hours. The product material was extracted by adding diluted hydrochloric acid and ethyl acetate, then dried and concentrated to obtain 4.4 g of Compound 21a by column chromatography.

Synthesis of Compound 21d

Compound 21d was synthesized thoroughly in the same manner as Compound 4d except for using Compound 21a in place of Compound 4a in the synthesis of Compound 4d.

Synthesis of Compound 21b

Compound 21b (amorphous) was synthesized thoroughly in the same manner as Compound 21d except for using trifluoroacetic anhydride in place of tetrafluorosuccinic anhydride in the synthesis of Compound 21d.

Synthesis of Compound 21c

Compound 21c was synthesized thoroughly in the same manner as Compound 21d except for using difluoroacetic anhydride in place of tetrafluorosuccinic anhydride in the synthesis of Compound 21d.

The hydrazine compound of the present invention is useful as a nucleating agent or a fogging agent of silver halide photographic light-sensitive materials.

The hydrazine compound of the present invention may be dissolved in an appropriate water-miscible organic solvent before use and examples of the solvent include alcohols (e.g., methanol, ethanol, propanol, fluorinated alcohol), ketones (e.g., acetone, methyl ethyl ketone), dimethylformamide, dimethylsulfoxide and methyl cellosolve.

Alternatively, the compound may be used as an emulsion dispersion product obtained by dissolving the compound according to an already well-known emulsion dispersion method using an oil such as dibutyl phthalate, tricresyl phosphate, glyceryl triacetate or diethyl phthalate, or an auxiliary solvent such as ethyl acetate or cyclohexanone, and mechanically forming it into an emulsion dispersion product. Further, powder of a hydrazine derivative may be used by dispersing it in water according to a method known as a solid dispersion method using a ball mill, a colloid mill or ultrasonic waves.

The hydrazine compound of the present invention may be added to any of silver halide emulsion layers and other hydrophilic colloid layers on the silver halide emulsion layer side of the support, however, it is preferably added to the silver halide emulsion layer or a hydrophilic colloid layer adjacent thereto.

The hydrazine compound of the present invention is preferably added in an amount of from $1\times10^{-6}$ to $1\times10^{-2}$ mol, more preferably from $1\times10^{-5}$ to $5\times10^{-3}$ mol, most preferably from $5\times10^{-5}$ to $5\times10^{-3}$ mol, per mol of silver halide.

In addition to the compounds described above, the hydrazine compound for use in the present invention include those described in *Research Disclosure*, Item 23516, p. 346 (November, 1983) and literatures cited therein, U.S. Pat. Nos. 4,080,207, 4,269,929, 4,276,364, 4,278,748, 4,385,108, 4,459,347, 4,478,928, 4,560,638, 4,686,167, 4,912,016, 4,988,604, 4,994,365, 5,041,355 and 4,104,769, British Patent 2,011,391B, European Patents 217,310, 301,799 and 356,898, JP-A-60-179734, JP-A-61-170733, JP-A-61-270744, JP-A-62-178246, JP-A-62-270948, JP-A-63-29751, JP-A-63-32538, JP-A-63-104047, JP-A-63-121838, JP-A-63-129337, JP-A-63-223744, JP-A-63-234244, JP-A-63-234245, JP-A-63-234246, JP-A-63-294552, JP-A-63-306438, JP-A-64-10233, JP-A-1-90439, JP-A-1-100530, JP-A-1-105941, JP-A-1-105943, JP-A-1-276128, JP-A-1-280747, JP-A-1-283548, JP-A-1-283549, JP-A-1-285940, JP-A-2-2541, JP-A-2-77057, JP-A-2-139538, JP-A-2-196234, JP-A-2-196235, JP-A-2-198440, JP-A-2-198441, JP-A-2-198442, JP-A-2-220042, JP-A-2-221953, JP-A-2-221954, JP-A-2-285342, JP-A-2-285343, JP-A-2-289843, JP-A-2-302750, JP-A-2-304550, JP-A-3-37642, JP-A-3-54549, JP-A-3-125134, JP-A-3-184039, JP-A-3-240036, JP-A-3-240037, JP-A-3-259240, JP-A-3-280038, JP-A-3-282536, JP-A-4-51143, JP-A-4-56842, JP-A-4-84134, JP-A-2-230233, JP-A-4-96053, JP-A-4-216544, JP-A-5-45761, JP-A-5- 45762, JP-A-5-45763, JP-A-5-45764, JP-A-5-45764 and Japanese Patent Application No. 5-94925.

The silver halide photographic light-sensitive material of the present invention may further contains a nucleation accelerator in at least one of emulsion layers and other hydrophilic colloid layers.

The nucleation accelerator for use in the present invention includes amine derivatives, onium salts, disulfide derivatives and hydroxymethyl derivatives. Examples thereof include: compounds described in JP-A-7-77783, page 48, lines 2 to 37, specifically, Compounds A-1) to A-73) described at pages 49 to 58; compounds represented by (Chem. 21), (Chem. 22) and (Chem. 23) of JP-A-7-84331, specifically, compounds described at pages 6 to 8; compounds represented by formulae [Na] and [Nb] of JP-A-7-104426, specifically, Compounds Na-1 to Na-22 and Compounds Nb-1 to Nb-12 described at pages 16 to 20; compounds represented by formulae (1), (2), (3), (4), (5), (6) and (7) of JP-A-8-272023, specifically, Compounds 1-1 to 1-19, Compounds 2-1 to 2-22, Compounds 3-1 to 3-36, Compounds 4-1 to 4-5, Compounds 5-1 to 5-41, Compounds 6-1 to 6-58 and Compounds 7-1 to 7-38.

Preferred nucleation accelerators for use in the present invention are those represented by the following formulae (IV), (V), (VI) and (VII):

(IV)

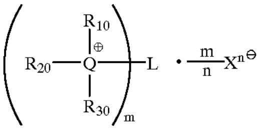

wherein $R_{10}$, $R_{20}$ and $R_{30}$ each represents an alkyl group, a cycloalkyl group, an aralkyl group, an aryl group, an alkenyl group, a cycloalkenyl group, an alkynyl group or a heterocyclic group, Q represents a nitrogen atom or a phosphorus atom, L represents an m-valent organic group bonded to $Q^+$ through the carbon atom (wherein m represents an integer of from 1 to 4), and $X^{n-}$ represents an n-valent counter anion (wherein n represents an integer of from 1 to 3), provided that when $R_{10}$, $R_{20}$, $R_{30}$ or L has an anion group on the substituent thereof and forms an inner salt with $Q^+$, $X^{n-}$ can be omitted;

(V)

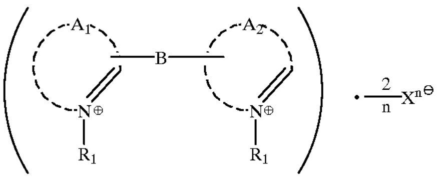

(VI)

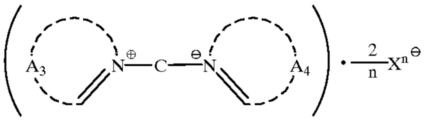

wherein $A_1$, $A_2$, $A_3$ and $A_4$ each represents an organic residue for completing a substituted or unsubstituted unsaturated heterocyclic ring containing a quaternized nitrogen atom, B and C each represents a divalent linking group formed of alkylene, arylene, alkenylene, alkynylene, —$SO_2$—, —SO—, —O—, —S—, —N($R'_N$)— (wherein $R'_N$ represents a hydrogen atom, an alkyl group, an aryl group or an aralkyl group), —C═O— or —P═O— individually or in combination, $R_1$ and $R_2$ each represents an alkyl group or an aralkyl group, and $X^{n-}$ represents an n-valent counter anion (wherein n represents an integer of from 1 to 3), provided that when an inner salt can be formed, $X^{n-}$ can be omitted;

(VII)

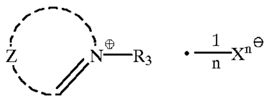

wherein Z represents an organic residue for completing a substituted or unsubstituted unsaturated heterocyclic ring containing a quaternized nitrogen atom, $R_3$ represents an alkyl group or an aralkyl group, and $X^{n-}$ represents an n-valent counter anion (wherein n represents an integer of from 1 to 3), provided that when an inner salt can be formed, $X^{n-}$ can be omitted.

The onium salt compounds represented by the formulae (IV), (V), (VI) and (VII) for use in the present invention are described in detail below.

Formula (IV) is first described in detail.

(IV)

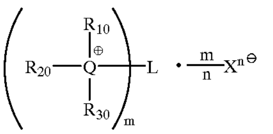

In the formula, $R_{10}$, $R_{20}$ and $R_{30}$ each represents an alkyl group, a cycloalkyl group, an aralkyl group, an aryl group, an alkenyl group, a cycloalkenyl group, an alkynyl group or a heterocyclic group, and these groups each may have further a substituent. Q represents a phosphorus atom or a nitrogen atom.

L represents an m-valent organic group bonded to $Q^+$ through the carbon atom, and m represents an integer of from 1 to 4. $X^{n-}$ represents an n-valent counter anion, and n represents an integer of from 1 to 3. However, when $R_{10}$, $R_{20}$, $R_{30}$ or L has an anion group on the substituent thereof and forms an inner salt with $Q^+$, $X^{n-}$ can be omitted.

Examples of the group represented by $R_{10}$, $R_{20}$ or $R_{30}$ include a linear or branched alkyl group such as methyl, ethyl, propyl, isopropyl, butyl, isobutyl, sec-butyl, tertbutyl, octyl, 2-ethylhexyl, dodecyl, hexadecyl and octadecyl; an aralkyl group such as substituted or unsubstituted benzyl; a cycloalkyl group such as cyclopropyl, cyclopentyl and cyclohexyl; an aryl group such as phenyl, naphthyl and phenanthryl; an alkenyl group such as allyl, vinyl and 5-hexenyl; a cycloalkenyl group such as cyclopentenyl and cyclohexenyl; an alkynyl group such as phenylethynyl; and a heterocyclic group such as pyridyl, quinolyl, furyl, imidazolyl, thiazolyl, thiadiazolyl, benzotriazolyl, benzothiazolyl, morpholyl, pyrimidyl and pyrrolidyl.

Examples of the substituent substituted on these groups include the groups represented by $R_{10}$, $R_{20}$ and $R_{30}$ a halogen atom such as fluorine, chlorine, bromine and iodine, a nitro group, an alkylamino group, an arylamino group, an alkoxy group, an aryloxy group, an alkylthio group, an arylthio group, a carbonamido group, a carbamoyl group, a sulfonamido group, sulfamoyl group, a hydroxyl group, a sulfoxy group, a sulfonyl group, a carboxyl group (including carboxylate), a sulfonic acid group (including sulfonate), a cyano group, an oxycarbonyl group and an acyl group.

Examples of the group represented by L, when m represents 1, include those exemplified for $R_{10}$, $R_{20}$ and $R_{30}$, and when m represents an integer of 2 or greater, include a polymethylene group such as trimethylene, tetramethylene, hexamethylene, pentamethylene, octamethylene and dodecamethylene, an arylene group such as phenylene, biphenylene and naphthylene, a polyvalent alkylene group such as trimethylenemethyl and tetramethylenemethyl, and a polyvalent arylene group such as phenylene-1,3,5-toluyl and phenylene-1,2,4,5-tetraryl.

Examples of the counter anion represented by $X^{n-}$ include a halogen ion such as chlorine ion, bromine ion and iodine ion, a carboxylate ion such as acetate ion, oxalate ion, fumarate ion and benzoate ion, a sulfonate ion such as p-toluene sulfonate, methane sulfonate, butane sulfonate and benzene sulfonate, a sulfate ion, a perchlorate ion, a carbonate ion and a nitrate ion.

In formula (IV), $R_{10}$, $R_{20}$ and $R_{30}$ each is preferably a group having 20 or less carbon atoms, more preferably an aryl group having 15 or less carbon atoms when Q represents a phosphorus atom, and an alkyl, aralkyl or aryl group having 15 or less carbon atoms when Q represents a nitrogen atom. m is preferably 1 or 2. When m represents 1, L is preferably a group having 20 or less carbon atoms, more preferably an alkyl, aralkyl or aryl group having a total carbon atom number of 15 or less. When m represents 2, the divalent organic group represented by L is preferably an alkylene group, an arylene group, an aralkylene group or a divalent group formed of a combination of one of these groups with —CO—, —O—, —N($R''_N$)— (wherein $R''_N$ represents a hydrogen atom or the group described for $R_{10}$, $R_{20}$ and $R_{30}$, and when a plurality of $R''_N$ groups are present within the molecule, they may be the same or different or may be combined to each other), —S—, —SO— or —$SO_2$—. When m represents 2, L is preferably a divalent group bonding to $Q^+$ through the carbon atom thereof and having a total carbon atom number of 20 or less. When m represents an integer of 2 or greater, $R_{10}$, $R_{20}$ or $R_{30}$ groups in plurality are present within the molecule and the plurality of $R_{10}$, $R_{20}$ or $R_{30}$ groups may be the same or different.

The counter anion represented by $X^{n-}$ is preferably a halogen ion, a carboxylate ion, a sulfonate ion or a sulfate ion, and n is preferably 1 or 2.

Most of the compounds represented by formula (IV) of the present invention are known and commercially available as a reagent. Examples of the general synthesis method include: when Q is a phosphorus atom, a method of reacting a phosphinic acid with an alkylating agent such as an alkyl halide or a sulfonic ester and a method of exchanging the counter anion of a phosphonium salt by a usual method; and when Q is a nitrogen atom, a method of alkylating a primary, secondary or tertiary amino compound with an alkylating agent such as an alkyl halide or a sulfonic ester.

Specific examples of the compound represented by formula (IV) are set forth below, however, the present invention is by no means limited to the following compounds.

A-1
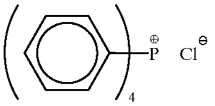
A-2
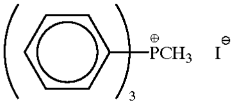
A-3
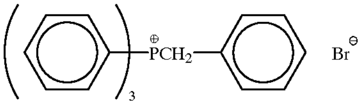
A-4
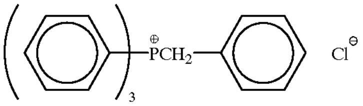
A-5
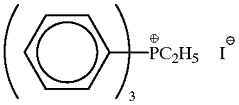
A-6
$(n\text{-}C_4H_8)_4\overset{\oplus}{P}\quad Br^{\ominus}$
A-7
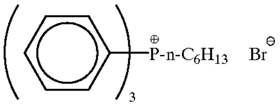
A-8
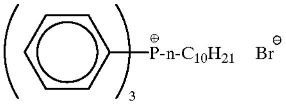
A-9
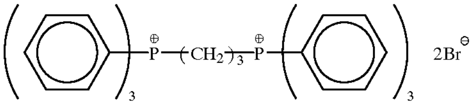
A-10
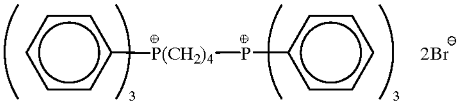
A-11
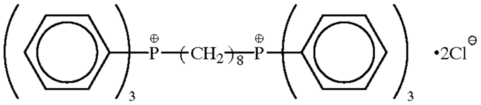
A-12
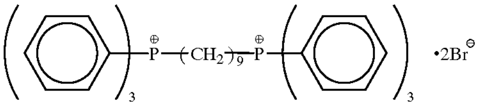
A-13
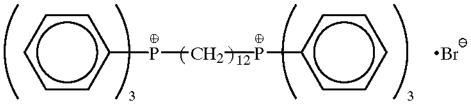

-continued
A-14
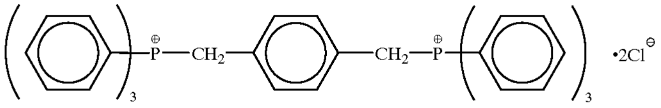
A-15
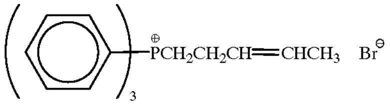
A-16
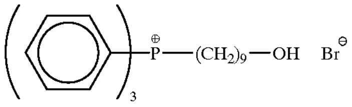
A-17
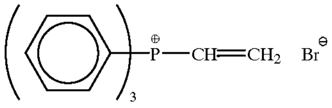
A-18
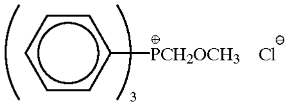
A-19
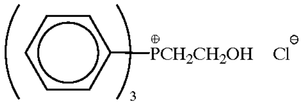
A-20
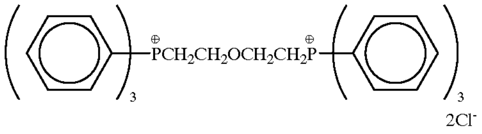
A-21
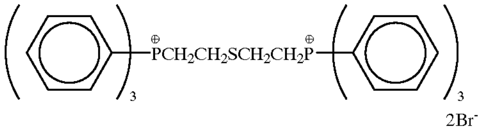
A-22
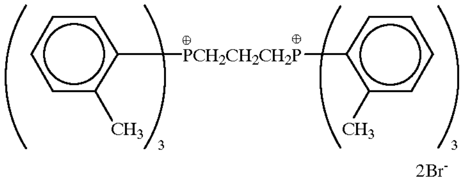
A-23
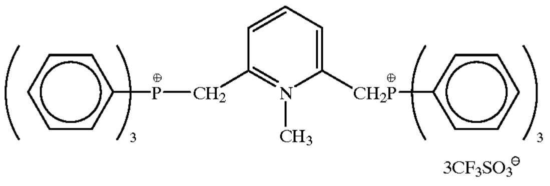
A-24
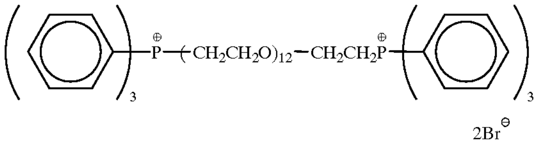

-continued
A-25
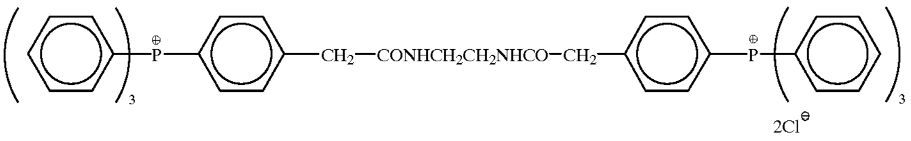
A-26
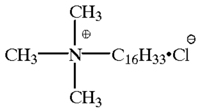
A-27
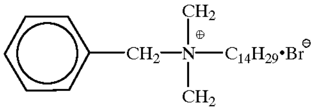
A-28
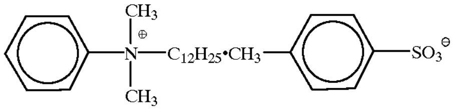
A-29
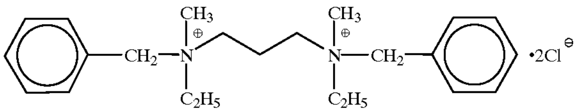
A-30
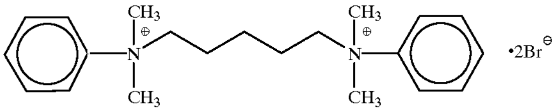
A-31
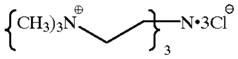
A-32
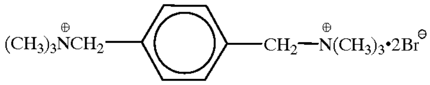
A-33
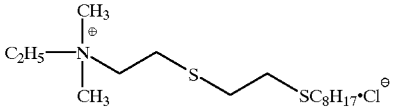
A-34
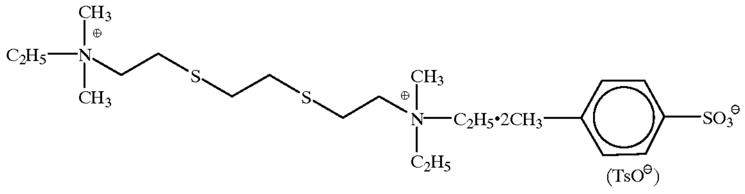
A-35
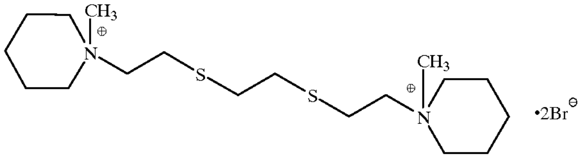

-continued

A-36

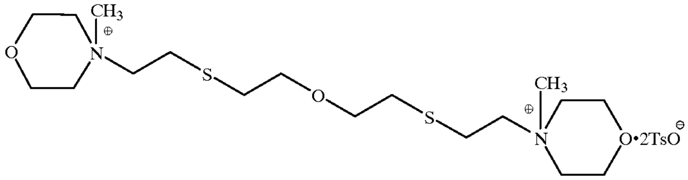

A-37

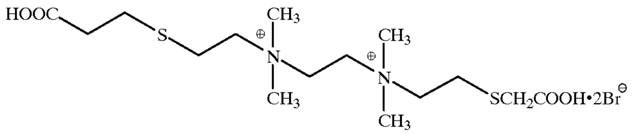

A-38

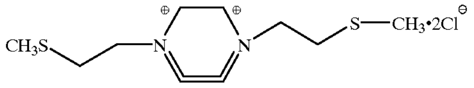

A-39

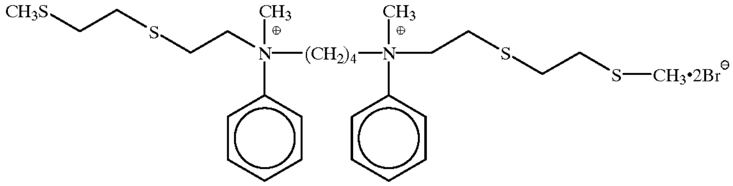

A-40

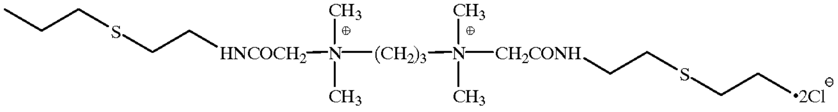

A-41

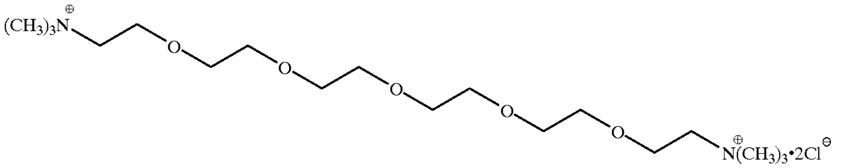

A-42

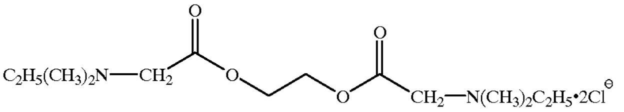

Formulae (V) and (VI) are described in more detail below.

(V)

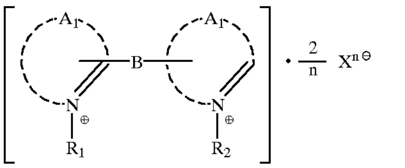

(VI)

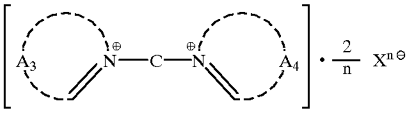

In the formulae, $A_1$, $A_2$, $A_3$ and $A_4$ each represents an organic residue for completing a substituted or unsubstituted unsaturated heterocyclic ring containing a quaternized nitrogen atom, and the ring may contain a carbon atom, a hydrogen atom, an oxygen atom, a nitrogen atom or a sulfur atom or may be condensed with a benzene ring. Examples of the unsaturated heterocyclic ring formed by $A_1$, $A_2$, $A_3$ or $A_4$ include a pyridine ring, a quinoline ring, an isoquinoline ring, an imidazole ring, a thiazole ring, a thiadiazole ring, a benzotriazole ring, a benzothiazole ring, a pyrimidine ring and a pyrazole ring, with a pyridine ring, a quinoline ring and an isoquinoline ring being preferred.

The divalent group represented by B or C is preferably a group formed of alkylene, arylene, alkenylene, alkynylene, $—SO_2—$, —SO—, —O—, —S—, $—N(R'_N)—$ (wherein $R'_N$ represents an alkyl group, an aralkyl group, an aryl group or a hydrogen atom), —C═O— or —P═O— individually or in combination, more preferably a group formed of alkylene, arylene, —C═O—, —O—, —S— and $—N(R_N)—$ individually or in combination.

$R_1$ and $R_2$, which may be the same or different, each is preferably an alkyl or aralkyl group having from 1 to 20 carbon atoms. Examples thereof includes linear or branched alkyl groups such as methyl, ethyl, propyl, isopropyl, butyl, isobutyl, sec-butyl, tert-butyl, octyl, 2-ethylhexyl, dodecyl, hexadecyl and octadecyl, and aralkyl groups such as benzyl. The alkyl and aralkyl groups may be substituted by a substituent, and examples of the substituent include a halogen atom (e.g., chlorine, bromine), a substituted or unsubstituted alkyl group (e.g., methyl, hydroxyethyl), a substituted or unsubstituted aryl group (e.g., phenyl, tolyl, p-chlorophenyl), a substituted or unsubstituted acyl group (e.g., benzoyl, p-bromobenzoyl, acetyl), an alkyloxycarbonyl group, an aryloxycarbonyl group, a sulfo group (including sulfonate), a carboxy group (including carboxylate), a mercapto group, a hydroxy group, an alkoxy group (e.g., methoxy, ethoxy), an aryloxy group, a carbonamido group, a sulfonamido group, a sulfamoyl group, a carbamoyl group, a ureido group, a thioureido group, an alkylamino group, an arylamino group, a cyano group, a nitro group, an alkylthio group and an arylthio group.

$R_1$ and $R_2$ each is more preferably an alkyl or aralkyl group having from 1 to 10 carbon atoms. Examples of preferred substituents include a carbamoyl group, an oxycarbonyl group, an acyl group, an aryl group, a sulfo group (including sulfonate), a carboxy group (including carboxylate) and a hydroxy group.

The unsaturated heterocyclic ring formed by $A_1$, $A_2$, $A_3$ or $A_4$ together with the quaternized nitrogen atom may have a substituent, and examples of the substituent include the substituents described above as the substituent of the alkyl group represented by $R_1$ or $R_2$. Preferred substituents are an aryl group having from 0 to 10 carbon atoms, an alkyl group, a carbamoyl group, an alkylamino group, an arylamino group, an oxycarbonyl group, an alkoxy group, an aryloxy group, an alkylthio group, an arylthio group, a hydroxy group, a carbonamido group, a sulfonamido group, a sulfo group (including sulfonate) and a carboxy group (including carboxylate).

The counter anion represented by $X^{n-}$ is the same as that in formula (IV) and the preferred range is also the same.

The compounds of the present invention can be easily synthesized by generally well-known methods, however, *Quart. Rev.*, 16, 163 (1962) may be referred to.

Specific examples of the compounds represented by formulae (V) and (VI) are set forth below, however, the present invention is by no means limited thereto.

B-1

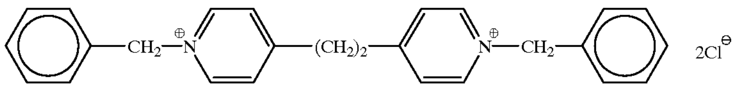

B-2

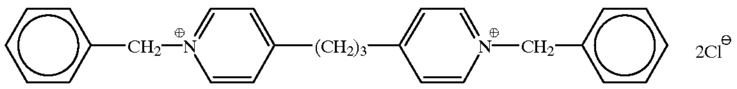

B-3

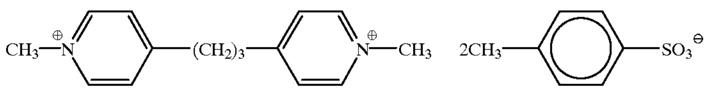

B-4

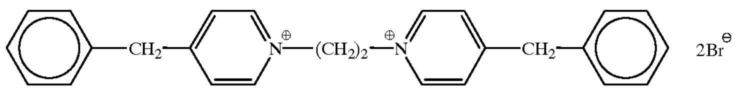

B-5

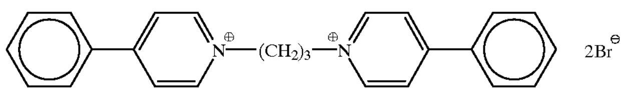

B-6

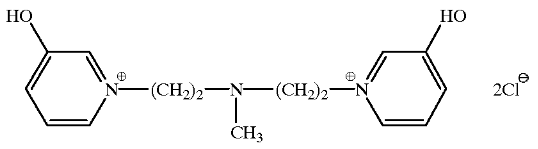

B-7

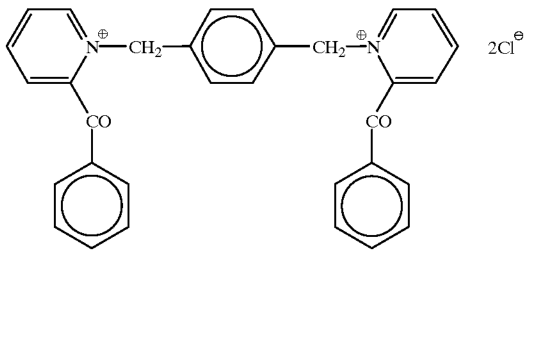

-continued
B-8
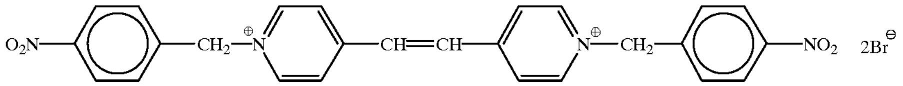
B-9
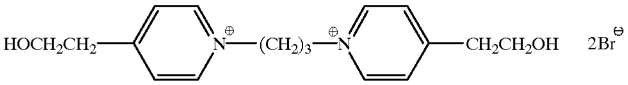
B-10
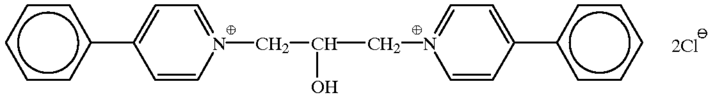
B-11
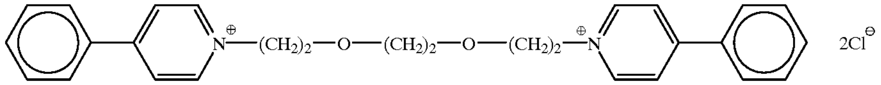
B-12
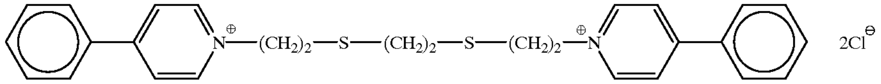
B-13
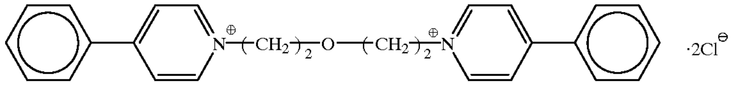
B-14
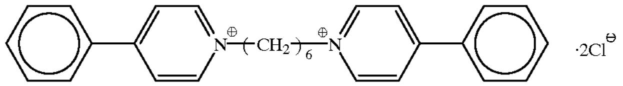
B-15
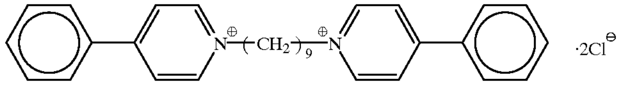
B-16
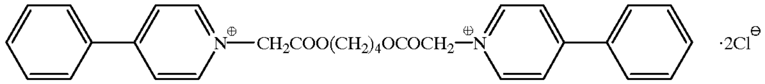
B-17
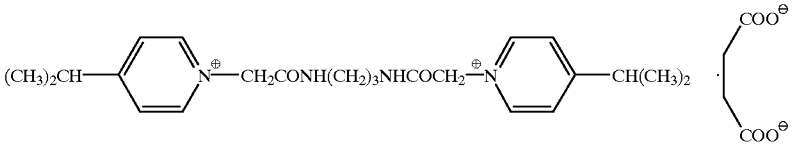
B-18
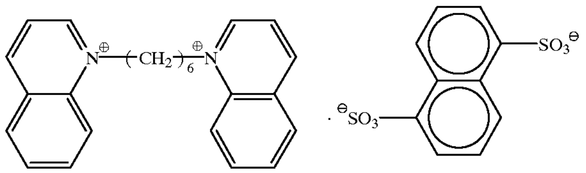
B-19
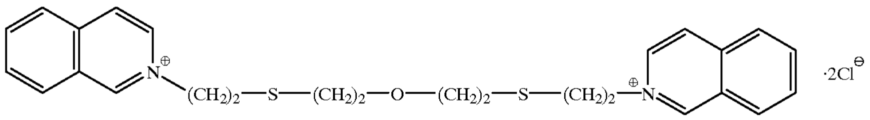

-continued

B-20

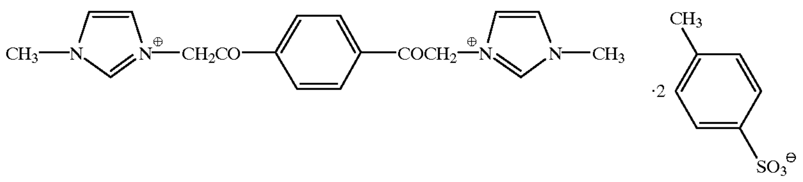

B-21

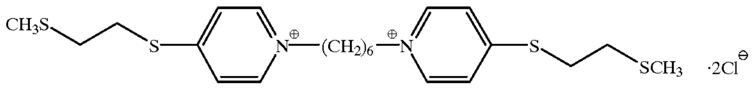

B-22

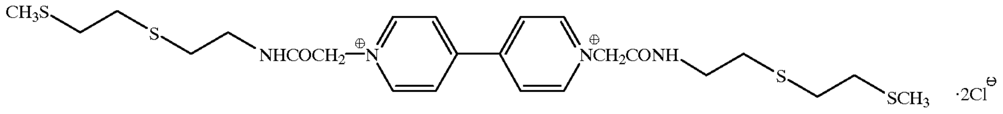

B-23

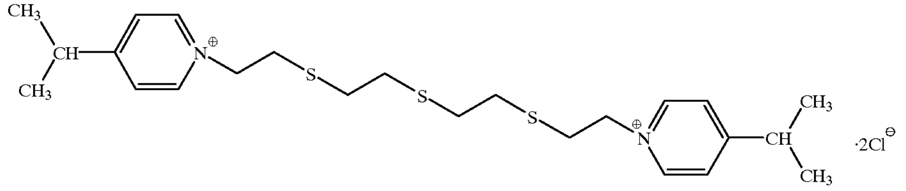

B-24

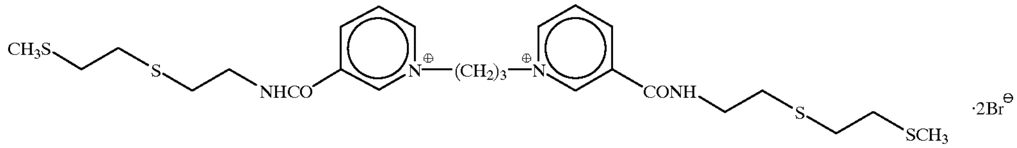

B-25

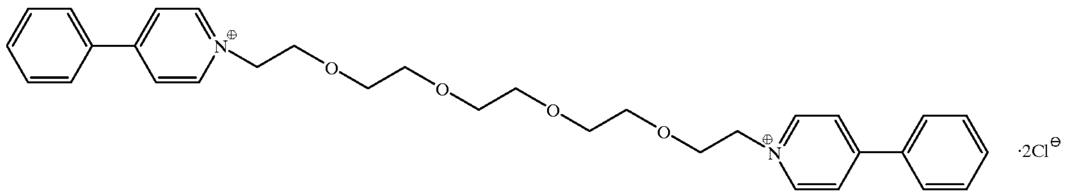

B-26

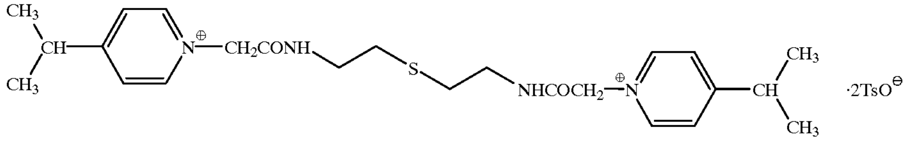

B-27

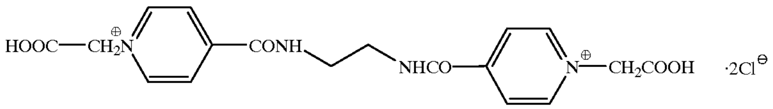

Formula (VII) is described in more detail below.

(VII)

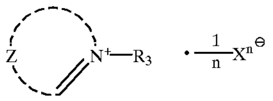

The nitrogen-containing unsaturated heterocyclic ring containing Z may contain, in addition to the nitrogen atom, a carbon atom, a hydrogen atom, an oxygen atom or a sulfur atom, may be condensed with a benzene ring, or may have a substituent. Examples of the heterocyclic ring formed include those described above as the nitrogen-containing unsaturated heterocyclic ring formed by $A_1$, $A_2$, $A_3$ or $A_4$ in formula (VI). The preferred range is also the same and a pyridine ring, a quinoline ring and an isoquinoline ring are preferred.

When the nitrogen-containing unsaturated heterocyclic ring containing Z has a substituent, examples of the substituent include those described above as the substituent of the nitrogen-containing unsaturated heterocyclic ring formed by $A_1$, $A_2$, $A_3$ or $A_4$ in formula (VI), and the preferred range is also the same.

$R_3$ represents an alkyl group or an aralkyl group, and the alkyl or aralkyl group may be a substituted or unsubstituted, linear, branched or cyclic alkyl or aralkyl group having from 1 to 20 carbon atoms. Examples of the substituent are the same as those described above as the substituent of the alkyl group represented by $R_1$ or $R_2$ in formula (V), and the preferred range is also the same.

The counter anion represented by $X^{n-}$ is the same as that in formula (IV) and the preferred range is also the same.

The compound represented by formula (VII) of the present invention can be easily synthesized by generally well-known methods, however, *Quart. Rev.*, 16, 163 (1962) may be referred to.

Specific examples of the compound represented by formula (VII) of the present invention are set forth below, however, the present invention is by no means limited thereto.

C-1

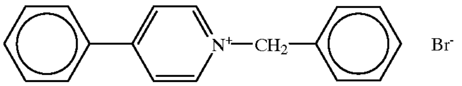

C-2

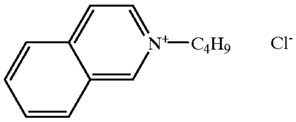

C-3

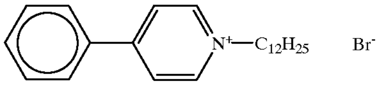

C-4

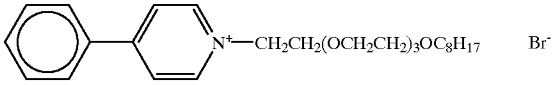

C-5

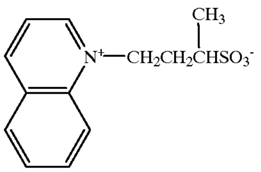

C-6

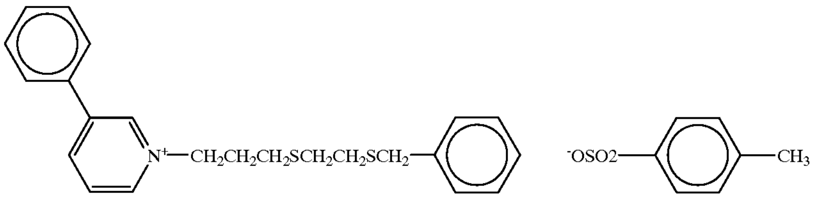

C-7

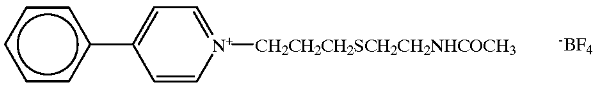

C-8

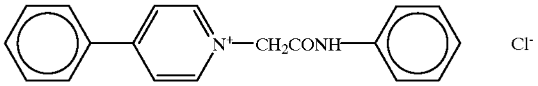

C-9

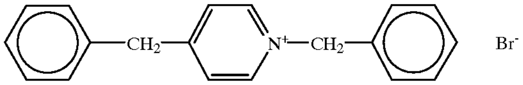

-continued

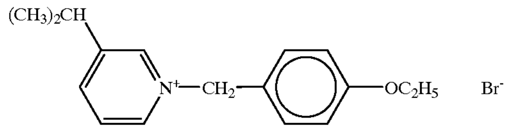

C-10

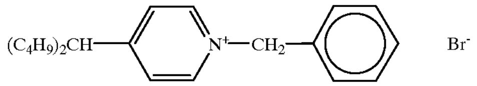

C-11

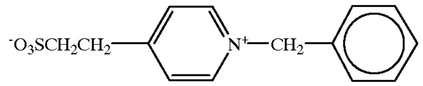

C-12

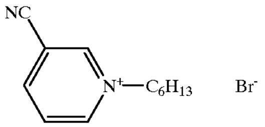

C-13

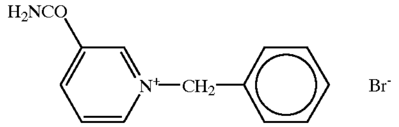

C-14

Examples of the amino compound which is preferably used as the nucleation accelerator in the present invention include: compounds represented by (Chem. 21), (Chem. 22) and (Chem. 23) of JP-A-7-84331, specifically, compounds described in pages 6 to 8; compounds represented by formula [Na] of JP-A-7-104426, specifically, Compounds Na-1 to Na-22 described at pages 16 to 20; compounds represented by formulae (1), (2), (3), (4), (5), (6) and (7) of JP-A-8-272023, specifically, Compounds 1-1 to 1-19, Compounds 2-1 to 2-22, Compounds 3-1 to 3-36, Compounds 4-1 to 4-5, Compounds 5-1 to 5-41, Compounds 6-1 to 6-58 and Compounds 7-1 to 7-38.

The nucleation accelerator for use in the present invention may be dissolved in an appropriate water-miscible organic solvent before use and examples of the solvent include alcohols (e.g., methanol, ethanol, propanol, fluorinated alcohol), ketones (e.g., acetone, methyl ethyl ketone), dimethylformamide, dimethylsulfoxide and methyl cellosolve.

Alternatively, the nucleation accelerator may be used as an emulsion dispersion product obtained by dissolving the compound according to an already well-known emulsion dispersion method using an oil such as dibutyl phthalate, tricresyl phosphate, glyceryl triacetate or diethyl phthalate, or an auxiliary solvent such as ethyl acetate or cyclohexanone, and mechanically forming it into an emulsion dispersion product. Further, powder of a nucleation accelerator may be used by dispersing it in water according to a method known as a solid dispersion method using a ball mill, a colloid mill or ultrasonic waves.

The nucleation accelerator for use in the present invention may be added to any of silver halide emulsion layers and other hydrophilic colloid layers on the silver halide emulsion layer side of the support, however, it is preferably added to the silver halide emulsion layer or a hydrophilic colloid layer adjacent thereto.

The nucleation accelerator for use in the present invention is preferably added in an amount of from $1\times10^{-6}$ to $2\times10^{-2}$ mol, more preferably from $1\times10^{-5}$ to $2\times10^{-2}$ mol, most preferably from $2\times10^{-5}$ to $1\times10^{2}$ mol, per mol of silver halide.

The silver halide of the silver halide emulsion for use in the present invention may be any of silver chloride, silver bromide, silver chlorobromide, silver chloroiodobromide and silver iodobromide, however, silver halide having a silver chloride content of 30 mol % or more, preferably 50 mol % or more is preferred. The silver iodide content is preferably 5 mol % or less, more preferably 2 mol % or less.

The silver halide grain may have any shape of cubic, tetradecahedral, octahedral, amorphous and platy forms, however, cubic or platy grains are preferred.

The photographic emulsion for use in the present invention can be prepared using a method described in P. Glafkides, *Chimie et Physique Photographique*, Paul Montel (1967), G. F. Duffin, *Photographic Emulsion Chemistry*, The Focal Press (1966), and V. L. Zelikman et al, *Making and Coating Photographic Emulsion*, The Focal Press (1964).

More specifically, either an acid process or a neutral process may be used, however, the emulsion is preferably prepared under acidic conditions. Further, a soluble silver salt may be reacted with a soluble halogen salt by any of a single jet method, a double jet method and a combination thereof.

A method of forming grains in the presence of excessive silver ion (so-called reverse mixing method) may also be used. As one form of the double jet method, a method of maintaining constant the pAg in the liquid phase where silver halide is produced, namely, a so-called controlled double jet method may be used. Further, it is preferred to form grains using a so-called silver halide solvent such as ammonia, thioether or tetra-substituted thiourea, more preferably using a tetra-substituted thiourea compound, and this is described in JP-A-53-82408 and JP-A-55-77737. Preferred examples of the thiourea compound include tetramethyl thiourea and 1,3-dimethyl-2-imidazolidinethione. The amount of silver halide solvent added varies depending on the kind of the compound used or the-grain size and halogen composition expected, however, it is preferably from $10^{-5}$ to $10^{-2}$ mol per mol of silver halide.

According to the controlled double jet method or the method of forming grains using a silver halide solvent, a silver halide emulsion comprising grains having a regular crystal form and a narrow grain size distribution can be easily prepared, and these methods are a useful means for preparing the silver halide emulsion for use in the present invention.

In order to render the grain size uniform, it is preferred to rapidly grow grains within the range of not exceeding the critical saturation degree, using a method of changing the addition rate of silver nitrate or alkali halide according to the grain growth rate as described in British Patent 1,535,016, JP-B-48-36890 and JP-B-52-16364, or a method of changing the concentration of the aqueous solution as described in British Patent 4,242,445 and JP-A-55-158124.

The emulsion for use in the present invention is preferably a monodisperse emulsion having a coefficient of variation obtained by the formula: {(standard deviation of grain size)/(average grain size}×100, of 20% or less, more preferably 15% or less.

The silver halide grains preferably have an average grain size of 0.5 μm or less, more preferably from 0.08 to 0.4 μm.

The silver halide emulsion for use in the present invention may contain a metal belonging to Group VIII. In order to achieve high contrast and low fogging, the silver halide emulsion preferably contains a rhodium compound, a ruthenium compound, a rhenium compound or a chromium compound. These heavy metals are preferably in the form of a metal coordination complex, and the hexa-coordination complex represented by the following formula is preferred:

$$[M(NY)_mL_{6-m}]^n$$

wherein M is a heavy metal selected from Ir, Ru, Rh, Re and Cr, L is a cross-linking ligand, Y is oxygen or sulfur, m is 0, 1 or 2, and n is 0, −1, −2 or −3.

Specific preferred examples of L include a halide ligand (e.g., fluoride, chloride, bromide, iodide), a cyanide ligand, a cyanate ligand, a thiocyanate ligand, a selenocyanate ligand, a tellurocyanate ligand, an acid ligand and an aquo ligand. When an aquo ligand is present, it preferably occupies one or more of the ligands.

In order to achieve high sensitivity, the silver halide emulsion for use in the present invention preferably contains an iron compound, more preferably a metal coordination complex having a cyan ligand as the ligand.

The above-described compound is dissolved in water or an appropriate solvent before use and a method commonly used for stabilizing the compound solution, namely, a method of adding an aqueous solution of hydrogen halogenide (e.g., hydrochloric acid, bromic acid, hydrofluoric acid) or an alkali halide (e.g., KCl, NaCl, KBr, NaBr), may be used. It is also possible to add and dissolve separately prepared silver halide grains which are previously doped with such a compound.

Specific examples of the metal coordination complex are set forth below.

1. $[Rh(H_2O)Cl_5]^{-2}$
2. $[RuCl_6]^{-3}$
3. $[Ru(NO)Cl_5]^{-2}$
4. $[RhCl_6]^{-3}$
5. $[Ru(H_2O)Cl_5]^{-2}$
6. $[Ru(NO)(H_2O)Cl_4]^{-1}$
7. $[Ru_2Cl_{10}O]^{-2}$
8. $[Re(NO)Cl_5]^{-2}$
9. $[Ir(NO)Cl_5]^{-2}$
10. $[Ir(H_2O)Cl_5]^{-2}$
11. $[Re(H_2O)Cl_5]^{-2}$
12. $[RhBr_6]^{-3}$
13. $[ReCl_6]^{-3}$
14. $[IrCl_6]^{-3}$
15. $[Re(NS)Cl_4(SeCN)]^{-2}$
16. $[Cr(CN)_6]^{-3}$
17. $[Fe(CN)_6]^{-3}$

The addition amount of the compound is from $1\times10^{-8}$ to $1\times10^{-2}$, preferably from $5\times10^{-8}$ to $2\times10^{-4}$ mol, per mol of silver in the silver halide emulsion.

The above-described compound may be added appropriately at the preparation of silver halide emulsion grains or at each stage before coating of the emulsion, however, it is preferably added at the formation of emulsion to integrate the compound into the silver halide grain.

The silver halide emulsion for use in the present invention is preferably subjected to chemical sensitization. The chemical sensitization may be performed using a known method such as sulfur sensitization, selenium sensitization, tellurium sensitization or noble metal sensitization, and these sensitization methods may be used individually or in combination. When these sensitization methods are used in combination, a combination of sulfur sensitization and gold sensitization, a combination of sulfur sensitization, selenium sensitization and gold sensitization, and a combination of sulfur sensitization, tellurium sensitization and gold sensitization are preferred.

The sulfur sensitization for use in the present invention is usually performed by adding a sulfur sensitizer and stirring the emulsion at a high temperature of 40° C. or higher for a predetermined time. The sulfur sensitizer may be a known compound and examples thereof include, in addition to the sulfur compound contained in gelatin, various sulfur compounds such as thiosulfates, thioureas, thiazoles and rhodanines. Also, sulfur sensitizers described in U.S. Pat. Nos. 1,574,944, 2,410,689, 2,278,947, 2,728,668, 3,501,313 and 3,656,955, German Patent 1,422,869, JP-B-56-24937 and JP-A-55-45016 can be used. Preferred sulfur compounds are a thiosulfate and a thiourea compound. The addition amount of the sulfur sensitizer varies depending upon various conditions such as the pH and the temperature at the time of chemical ripening and the size of silver halide grains, however, it is preferably from $10^{-7}$ to $10^{-2}$ mol, more preferably from $10^{-5}$ to $10^{-4}$ mol, per mol of silver halide.

The selenium sensitizer for use in the present invention may be a known selenium compound. The selenium sensitization is usually performed by adding a labile and/or non-labile selenium compound and stirring the emulsion at a high temperature of 40° C. or higher for a predetermined time. Examples of the labile selenium compound include the compounds described in JP-B-44-15748, JP-B-43-13489 and JP-A-4-25832, JP-A-4-109240 and JP-A-4-324855, and among these, particularly preferred are the compounds represented by formulae (VIII) and (IX) of JP-A-4-324855.

A low decomposition activity selenium compound can be also preferably used. The low decomposition activity selenium compound is a selenium compound such that when a water/1,4-dioxane (1/1 by volume) mixed solution (pH: 6.3) containing 10 mmol of $AgNO_3$, 0.5 mmol of the selenium compound and 40 mmol of 2-(N-morpholino)ethanesulfonic acid buffer was reacted at 40° C., the half life of the selenium compound is 6 hours or more.

The tellurium sensitizer for use in the present invention is a compound of forming silver telluride presumed to become a sensitization nucleus, on the surface or in the inside of a silver halide grain. The formation rate of silver telluride in a silver halide emulsion can be examined according to a method described in JP-A-5-313284.

Specific examples of the tellurium sensitizer include the compounds described in U.S. Pat. Nos. 1,623,499, 3,320,069 and 3,772,031, British Patents 235,211, 1,121,496, 1,295,462 and 1,396,696, Canadian Patent 800,958, JP-A-4-204640, JP-A-4-271341, JP-A-4-333043 and JP-A-5-303157, *J. Chem. Soc. Chem. Commun.*, 635 (1980), *ibid.*, 1102 (1979), *ibid.*, 645 (1979), *J. Chem. Soc. Perkin. Trans.*, 1, 2191 (1980), S. Patai (compiler), *The Chemistry of Organic Selenium and Tellurium Compounds*, Vol. 1 (1986), and *ibid.*, Vol. 2 (1987). The compounds represented by formulae (II), (III) and (IV) of JP-A-5-313284 are particularly preferred.

The use amount of the selenium sensitizer or the tellurium sensitizer for use in the present invention varies depending upon silver halide grains used or chemical ripening conditions, however, it is usually from $10^{-8}$ to $10^{-2}$ mol, preferably approximately from $10^{-7}$ to $5\times10^{-4}$ mol, per mol of silver halide. The conditions of chemical sensitization in the present invention are not particularly restricted, however, the pH is from 5 to 8, the pAg is from 6 to 11, preferably from 7 to 10, and the temperature is from 40 to 95° C., preferably from 45 to 85° C.

Examples of the noble metal sensitizer for use in the present invention include gold, platinum, palladium and iridium, and gold sensitization is particularly preferred. The gold sensitizer for use in the present invention may have a gold oxidation number of either +1 valence or +3 valence and specific examples thereof include chloroaurate, potassium chloroaurate, auric trichloride, potassium auric thiocyanate, potassium iodoaurate, tetracyanoauric acid, ammonium aurothiocyanate, pyridyltrichlorogold and gold sulfide. The gold sensitizer can be used in an amount of approximately from $10^{-7}$ to $10^{-2}$ mol per mol of silver halide.

In the silver halide emulsion for use in the present invention, a cadmium salt, a sulfite, a lead salt or a thallium salt may be present together during formation or physical ripening of silver halide grains.

In the present invention, reduction sensitization may be used. Examples of the reduction sensitizer which can be used include stannous salt, amines, formamidinesulfinic acid and silane compounds.

To the silver halide emulsion for use in the present invention, a thiosulfonic acid compound may be added according to the method described in European Unexamined Patent Publication (EP) 293917. The amount of thiosulfonic acid compound added varies over a fairly broad range depending on various conditions such as the pH, the temperature and the size of silver halide grains, however, it is preferably from $1\times10^{-7}$ to $5\times10^{-2}$ mol per mol of silver halide.

In the light-sensitive material of the present invention, a sole kind of silver halide emulsion may be used or two or more kinds of silver halide emulsions (for example, different in the average grain size, different in the halogen composition, different in the crystal habit or different in the conditions of chemical sensitization) may be used in combination.

The light-sensitive silver halide emulsion for use in the present invention may be spectrally sensitized to blue light, green light, red light or infrared light having a relatively long wavelength by a sensitizing dye. Examples of the sensitizing dye which can be used include a cyanine dye, a merocyanine dye, a complex cyanine dye, a complex merocyanine dye, a holopolar cyanine dye, a styryl dye, a hemicyanine dye, an oxonol dye and a hemioxonol dye.

Useful sensitizing dyes for use in the present invention are described, for example, in *Research Disclosure*, Item 17643, IV-A, page 23 (December, 1978), *ibid.*, Item 1831X, page 437 (August, 1979), and publications cited therein.

In particular, sensitizing dyes having spectral sensitivity suitable for spectral characteristics of various light sources in a scanner, an image setter or a photomechanical camera can be advantageously selected.

For example, A) for an argon laser light source, Compounds (1)-1 to (1)-8 described in JP-A-60-162247, Compounds I-1 to I-28 described in JP-A-2-48653, Compounds I-1 to I-13 described in JP-A-4-330434, Compound Examples 1 to 14 described in U.S. Pat. No. 2,161,331, and Compounds 1 to 7 described in West German Patent 936,071, B) for a helium-neon laser light source, Compounds I-1 to I-38 described in JP-A-54-18726, Compounds I-1 to I-35 described in JP-A-6-75322, and Compounds I-1 to I-34 described in JP-A-7-287338, C) for an LED light source, Dyes 1 to 20 described in JP-B-55-39818, Compounds I-1 to I-37 described in JP-A-62-284343 and Compounds I-1 to I-34 described in JP-A-7-287338, D) for a semiconductor laser light source, Compounds I-1 to I-12 described in JP-A-59-191032, Compounds I-1 to I-22 described in JP-A-60-80841, Compounds I-1 to I-29 described in JP-A-4-335342, and Compounds I-1 to I-18 described in JP-A-59-192242, and E) for a tungsten or xenon light source of a photomechanical camera, Compounds (1) to (19) represented by formula [I] of JP-A-55-45015, and Compounds 4-A to 4-S, Compounds 5-A to 5-Q and Compounds 6-A to 6-T described in JP-A-6-242547 may be advantageously selected.

These sensitizing dyes may be used individually or in combination, and the combination of sensitizing dyes is often used for the purpose of supersensitization. In combination with the sensitizing dye, a dye which itself has no spectral sensitization effect or a material which absorbs substantially no visible light, but which exhibits supersensitization may be incorporated into the emulsion.

Useful sensitizing dyes, combinations of dyes which exhibit supersensitization, and materials which show supersensitization are described in *Research Disclosure*, Vol. 176, 17643, page 23, Item IV-J (December, 1978), JP-B-49-25500, JP-B-43-4933, JP-A-59-19032 and JP-A-59-192242.

The sensitizing dyes for use in the present invention may be used in combination of two or more thereof. The sensitizing dye may be added to a silver halide emulsion by dispersing it directly in the emulsion or by dissolving it in a sole or mixed solvent of water, methanol, ethanol, propanol, acetone, methyl cellosolve, 2,2,3,3-tetrafluoropropanol, 2,2,2-trifluoroethanol, 3-methoxy-1-propanol, 3-methoxy-1-butanol, 1-methoxy-2-propanol or N,N-dimethylformamide, and then adding the solution to the emulsion.

Alternatively, the sensitizing dye may be added to the emulsion by a method described in U.S. Pat. No. 3,469,978 where a dye is dissolved in a volatile organic solvent, the solution is dispersed in water or a hydrophilic colloid and the dispersion is added to the emulsion, a method described in JP-B-44-23389, JP-B-44-27555 and JP-B-57-22091 where a dye is dissolved in an acid and the solution is added to the emulsion or formed into an aqueous solution in the presence of an acid or a base together and then added to the emulsion, a method described in U.S. Pat. Nos. 3,822,135 and 4,006,025 where a dye is formed into an aqueous solution or a colloid dispersion in the presence of a surface active agent together and the aqueous solution or dispersion is added to the emulsion, a method described in JP-A-53-102733 and JP-A- 58-105141 where a dye is directly dispersed in a hydrophilic colloid and the dispersion is added to the emulsion, or a method described in JP-A-51-74624 where a dye is dissolved using a compound capable of red-shift and the solution is added to the emulsion. Ultrasonic waves may also be used in the solution.

The sensitizing dye for use in the present invention may be added to a silver halide emulsion of the present invention at any step known to be useful during the preparation of emulsion. For example, the dye may be added at a step of formation of silver halide grains and/or in a period before desalting or at a step of desalting and/or in a period between after desalting and before initiation of chemical ripening as disclosed in U.S. Pat. Nos. 2,735,766, 3,628,960, 4,183,756 and 4,225,666, JP-A-58-184142 and JP-A-60-196749, or the dye may be added in any period or at any step before coating of the emulsion such as immediately before or during chemical ripening or in a period after chemical ripening but before coating as described in JP-A-58-113920. Also, a sole kind of compound alone or compounds different in the structure in combination may be added in installments, for example, a part during grain formation and the remaining during chemical ripening or after completion of the chemical ripening, or a part before or during chemical ripening and the remaining after completion of the chemical ripening as disclosed in U.S. Pat. No. 4,225,666 and JP-A-58-7629. The kind of compounds added in installments or the kind of the combination of compounds may be changed.

The addition amount of the sensitizing dye for use in the present invention varies depending upon the shape, size, halogen composition of silver halide grains, the method and degree of chemical sensitization and the kind of antifoggant, however, the addition amount can be from $4\times10^{-6}$ to $8\times10^{-3}$ mol per mol of silver halide. For example, in the case where the silver halide grain size is from 0.2 to 1.3 $\mu$m, the addition amount is preferably from $2\times10^{-7}$ to $3.5\times10^{-6}$, more preferably from $6.5\times10^{-7}$ to $2.0\times10^{-6}$ mol, per $m^2$ of the surface area of a silver halide grain.

Various additives for use in the light-sensitive material of the present invention are not particularly limited and, for example, those described in the portion shown below can be preferably used:

polyhydroxybenzene compounds described in JP-A-3-39948, from page 10, right lower column, line 11 to page 12, left lower column, line 5, specifically, compounds (III)-1 to (III)-25;

compounds having substantially no absorption maximum in the visible region, represented by formula (I) of JP-A-118832, specifically, Compounds I-1 to I-26;

antifoggants described in JP-A-2-103536, from page 17, right lower column, line 19 to page 18, right upper column, line 4;

polymer latexes described in JP-A-2-103536, page 18, left lower column, lines 12 to 20;

matting agents, slipping agents and plasticizers described in JP-A-2-103536, page 19, from left upper column, line 15 to right upper column, line 15;

hardening agents described in JP-A-2-103536, page 18, right upper column, lines 5 to 17;

compounds having an acid group described in JP-A-2-103536, from page 18, right lower column, line 6 to page 19, left upper column, line 1;

electrically conductive substances described in JP-A-2-18542, from page 2, left lower column, line 13 to page 3, right upper column, line 7, specifically metal oxides described at page 2, right lower column, lines 2 to 10 and Compounds P-1 to P-7 as an electrically conductive polymer compound;

water-soluble dyes described in JP-A-2-103536, page 17, right lower column, line 1 to right upper column, line 18;

solid disperse dyes described in JP-A-7-152112, specifically, Compounds (II-2) to (II-24), Compounds (III-5) to (III-18) and Compounds (IV-2) to (IV-7);

solid disperse dyes described in JP-A-2-294638 and JP-A-5-11382;

surface active agents described in JP-A-2-12236, page 9, from right upper column, line 7 to right lower column, line 3; PEG-base surface active agents described in JP-A-2-103536, page 18, left lower column, lines 4 to 7; fluorine-containing surface active agents described in JP-A-3-39948, from page 12, left lower column, line 6 to page 13, right lower column, line 5, specifically, Compounds VI-1 to VI-15;

a hydrazine derivative which may be used in combination, including: compounds represented by formula (I) of JP-A-7-287355, specifically, Compounds I-1 to I-53; compounds represented by (Chem. 1) of JP-B-6-77138, specifically, compounds described at pages 3 and 4; compounds represented by formula (I) of JP-B-6-93082, specifically, Compounds 1 to 38 described at pages 8 to 18; compounds represented by formulae (4), (5) and (6) of JP-A-6-230497, specifically, Compounds 4-1 to 4-10 described at pages 25 and 26, Compounds 5-1 to 5-42 described at pages 28 to 36, and Compounds 6-1 to 6-7 described at pages 39 to 40; compounds represented by formulae (1) and (2) of JP-A-6-289520, specifically, Compounds 1-1) to 1-17) and 2-1) described at pages 5 to 7; compounds represented by (Chem. 2) and (Chem. 3) of JP-A-6-313936, specifically, compounds described at pages 6 to 19; compounds represented by (Chem. 1) of JP-A-6-313951, specifically, compounds described at pages 3 to 5; compounds represented by formula (1) of JP-A-7-5610, specifically, Compounds I-1 to I-38 described at pages 5 to 10; compounds represented by formula (II) of JP-A-7-77783, specifically, Compounds II-1 to II-102 described at pages 10 to 27; compounds represented by formulae (H) and (Ha) of JP-A-7-104426, specifically, Compounds H-1 to H-44 described at pages 8 to 15; compounds characterized by having, in the vicinity of a hydrazine group, an anionic group or a nonionic group of forming an intramolecular hydrogen bond with the hydrogen atom of hydrazine described in JP-A-9-22082, particularly, compounds represented by formulae (A), (B), (C), (D), (E) and (F), specifically, Compounds N-1 to N-30; compounds represented by formula (1) of JP-A-9-22082, specifically, Compounds D-1 to D-55;

redox compounds capable of releasing a development inhibitor upon oxidation described in JP-A-5-274816, preferably, redox compounds represented by formulae (R-1), (R-2) and (R-3), specifically, Compounds R-1 to R-68; and binders described in JP-A-2-18542, page 3, right lower column, lines 1 to 20.

The processing agent such as developer and fixing solution and the processing method for use in the present invention are described below, however, of course, the present invention is by no means limited to the following description and specific examples.

The development for use in the present invention may be performed by any known method, and a known development processing solution may be used.

The developing agent for use in the developer (the development initiating solution and the development replenisher are collectively called a developer, hereinafter the same) used in the present invention is not particularly restricted, however, it preferably contains a dihydroxybenzene, an ascorbic acid derivative or a hydroquinone monosulfonate individually or in combination. In view of the developing capability, a combination of a dihydroxybenzene or an ascorbic acid derivative with a 1-phenyl-3-pyrazolidone and a combination of a dihydroxybenzene or an ascorbic acid derivative with a p-aminophenol are preferred.

Examples of the dihydroxybenzene developing agent for use in the present invention include hydroquinone, chlorohydroquinone, isopropylhydroquinone and methylhydroquinone, with hydroquinone being particularly preferred. Examples of the ascorbic acid derivative developing agent include an ascorbic acid, an isoascorbic acid and a salt thereof, with sodium erythorbate being particularly preferred in view of the cost for materials.

Examples of the 1-phenyl-3-pyrazolidone or a derivative thereof as the developing agent for use in the present invention include 1-phenyl-3-pyrazolidone, 1-phenyl-4,4-dimethyl-3-pyrazolidone and 1-phenyl-4-methyl-4-hydroxymethyl-3-pyrazolidone.

Examples of the p-aminophenol-base developing agent for use in the present invention include N-methyl-p-aminophenol, p-aminophenol, N-(β-hydroxyethyl)-p-aminophenol and N-(4-hydroxyphenyl)glycine, with N-methyl-p-aminophenol being particularly preferred.

The dihydroxybenzene-base developing agent in usual is preferably used in an amount of from 0.05 to 0.8 mol/l. In the case when a dihydroxybenzene and a 1-phenyl-3-pyrazolidone or a p-aminophenol are used in combination, the former is preferably used in an amount of from 0.05 to 0.6 mol/l, more preferably from 0.23 to 0.5 mol/l, and the latter is preferably used in an amount of 0.06 mol/l or less, more preferably from 0.003 to 0.03 mol/l.

The ascorbic acid derivative developing agent in usual is preferably used in an amount of from 0.01 to 0.5 mol/l, more preferably from 0.05 to 0.3 mol/l. In the case when an ascorbic acid derivative and a 1-phenyl-3-pyrazolidone or a p-aminophenol are used in combination, the ascorbic acid derivative is preferably used in an amount of from 0.01 to 0.5 mol/l, and the 1-phenyl-3-pyrazolidone or p-aminophenol is preferably used in an amount of from 0.005 to 0.2 mol/l.

The developer used in processing the light-sensitive material of the present invention may contain additives (e.g., developing agent, alkali agent, pH buffer, preservative, chelating agent) which are commonly used. Specific examples thereof are described below, however, the present invention is by no means limited thereto.

Examples of the buffer for use in the developer used in development processing the light-sensitive material of the present invention include carbonates, boric acids described in JP-A-62-186259, saccharides (e.g., saccharose) described in JP-A-60-93433, oximes (e.g., acetoxime), phenols (e.g., 5-sulfosalicylic acid) and tertiary phosphates (e.g., sodium salt, potassium salt), with carbonates and boric acids being preferred. The buffer, particularly the carbonate, is preferably used in an amount of 0.1 mol/l or more, more preferably from 0.2 to 1.5 mol/l.

Examples of the preservative for use in the present invention include sodium sulfite, potassium sulfite, lithium sulfite, ammonium sulfite, sodium bisulfite, sodium metabisulfite, and formaldehyde-sodium bisulfite. The sulfite is used in an amount of 0.2 mol/l or more, preferably 0.3 mol/l or more, but if it is added too excessively, silver staining in the developer is caused. Accordingly, the upper limit is preferably 1.2 mol/l. The amount is more preferably from 0.35 to 0.7 mol/l.

In combination with the sulfite, a small amount of an ascorbic acid derivative which is described above, may be added as a preservative for the dihydroxybenzene developing agent. In particular, sodium erythorbate is preferably used in view of the cost for materials. The addition amount in mol thereof is, based on the dihydroxybenzene developing agent, preferably from 0.03 to 0.12, more preferably from 0.05 to 0.10. In the case of using the ascorbic derivative as a preservative, the developer preferably contains no boron compound.

Examples of additives other than those described above include a development inhibitor such as sodium bromide and potassium bromide, an organic solvent such as ethylene glycol, diethylene glycol, triethylene glycol and dimethylformamide, an alkanolamine such as diethanolamine and triethanolamine, a development accelerator such as imidazole and derivatives thereof, and a physical development unevenness inhibitor such as a heterocyclic mercapto compound (e.g., sodium 3-(5-mercaptotetrazol-1-yl) benzenesulfonate, 1-phenyl-5-mercaptotetrazole) and the compounds described in JP-A-62-212651.

Further, a mercapto-base compound, an indazole-base compound, a benzotriazole-base compound or a benzimidazole compound may be added as an antifoggant or a black spot (black pepper) inhibitor. Specific examples thereof include 5-nitroindazole, 5-p-nitrobenzoylaminoindazole, 1-methyl-5-nitroindazole, 6-nitroindazole, 3-methyl-5-nitroindazole, 5-nitrobenzimidazole, 2-isopropyl-5-nitrobenzimidazole, 5-nitrobenzotriazole, sodium 4-((2-mercapto-1,3,4-thiadiazol-2-yl)thio)butanesulfonate, 5-amino-1,3,4-thiadiazole-2-thiol, methylbenzotriazole, 5-methylbenzotriazole and 2-mercaptobenzotriazole. The addition amount thereof is usually from 0.01 to 10 mmol, preferably from 0.1 to 2 mmol, per liter of the developer.

Further, various kinds of organic and inorganic chelating agents can be used individually or in combination in the developer for use in the present invention.

Examples of the inorganic chelating agent include sodium tetrapolyphosphate and sodium hexametaphosphate.

Examples of the organic chelating agent include organic carboxylic acid, aminopolycarboxylic acid, organic phosphonic acid, aminophosphonic acid and organic phosphonocarboxylic acid.

Examples of the organic carboxylic acid include acrylic acid, oxalic acid, malonic acid, succinic acid, glutaric acid, gluconic acid, adipic acid, pimelic acid, azelaic acid, sebacic acid, nonanedicarboxylic acid, decanedicarboxylic acid, undecanedicarboxylic acid, maleic acid, itaconic acid, malic acid, citric acid and tartaric acid.

Examples of the aminopolycarboxylic acid include iminodiacetic acid, nitrilotriacetic acid, nitrilotripropionic acid, ethylenediaminomonohydroxyethyltriacetic acid, ethylenediaminetetraacetic acid, glycol ether tetraacetic acid, 1,2-diaminopropanetetraacetic acid, diethylenetriaminepentaacetic acid, triethylenetetraminehexaacetic acid, 1,3-diamino-2-propanoltetraacetic acid, glycol ether aminetetraacetic acid and compounds described in JP-A-52-25632, JP-A-55-67747, JP-A-57-102624 and JP-B-53-40900.

Examples of the organic phosphonic acid include hydroxyalkylidene-diphosphonic acid described in U.S. Pat.

Nos. 3,214,454 and 3,794,591 and German Patent Publication (OLS) No. 2,227,639, and the compounds described in *Research Disclosure*, Vol. 181, Item 18170 (May, 1979).

Examples of the aminophosphonic acid include aminotris (methylenephosphonic acid), ethylenediaminetetramethylenephosphonic acid, aminotrimethylenephosphonic acid, and the compounds described in *Research Disclosure*, No. 18170 (supra), JP-A-57-208554, JP-A-54-61125 and JP-A-55-29883.

Examples of the organic phosphonocarboxylic acid include the compounds described in JP-A-52-102726, JP-A-53-42730, JP-A-54-121127, JP-A-55-4024, JP-A-55-4025, JP-A-55-126241, JP-A-55-65955, JP-A-55-56956 and *Research Disclosure*, No. 18170 (supra).

The organic and/or inorganic chelating agents are not limited to those described above. The organic and/or inorganic chelating agents may be used in the form of an alkali metal salt or an ammonium salt. The amount of the chelating agent added is preferably from $1\times10^{-4}$ to $1\times10^{-1}$ mol, more preferably from $1\times10^{-3}$ to $1\times10^{-2}$ mol, per liter of the developer.

Examples of the silver staining inhibitor added to the developer include the compounds described in JP-A-56-24347, JP-B-56-46585, JP-B-62-2849, JP-A-4-362972 and JP-A-8-6215, triazine having one or more mercapto groups (for example, the compounds described in JP-B-6-23830, JP-A-3-282457 and JP-A-7-175178), pyrimidine having one or more mercapto groups (e.g., 2-mercaptopyrimidine, 2,6-dimercaptopyrimidine, 2,4-dimercaptopyrimidine, 5,6-diamino-2,4-dimercaptopyrimidine, 2,4,6-trimercaptopyrimidine), pyridine having one or more mercapto groups (e.g., 2-mercaptopyridine, 2,6-dimercaptopyridine, 3,5-dimercaptopyridine, 2,4,6-trimercaptopyridine, compounds described in JP-A-7-248587), pyrazine having one or more mercapto groups (e.g., 2-mercaptopyrazine, 2,6-dimercaptopyrazine, 2,3-dimercaptopyrazine, 2,3,5-trimercaptopyrazine), pyridazine (e.g., 3-mercaptopyridazine, 3,4-dimercaptopyridazine, 3,5-dimercaptopyridazine, 3,4,6-trimercaptopyridazine), the compounds described in JP-A-7-175177 and polyoxyalkylphosphonic esters described in U.S. Pat. No. 5,457,011. These silver staining inhibitors may be used individually or in combination of a plurality of the compounds. The addition amount thereof is preferably from 0.05 to 10 mmol, more preferably from 0.1 to 5 mmol, per l of the developer.

The developer may contain the compounds described in JP-A-61-267759 as a dissolution aid.

Further, the developer may contain a color toner, a surface active agent, a defoaming agent or a hardening agent, if desired.

The developer preferably has a pH of from 9.0 to 12.0, more preferably from 9.5 to 11.0. The alkali agent used for adjusting the pH may be a normal water-soluble inorganic alkali metal salt (e.g., sodium hydroxide, potassium hydroxide, sodium carbonate, potassium carbonate).

With respect to the cation of the developer, potassium ion does not inhibit development and causes small indentations called a fringe on the periphery of the blacked portion as compared with sodium ion. When the developer is stored as a concentrated solution, potassium ion is generally preferred because of its higher solubility. However, since in the fixing solution, potassium ion causes fixing inhibition on the same level as caused by silver ion, if the developer has a high potassium ion concentration, the developer is carried over by the light-sensitive material to disadvantageously increase the potassium ion concentration in the fixing solution. Accordingly, the molar ratio of potassium ion to sodium ion in the developer is preferably between 20:80 and 80:20. The ratio of potassium ion to sodium ion can be freely controlled within the above-described range by the counter cation such as a pH buffer, a pH adjusting agent, a preservative or a chelating agent.

The replenishing amount of the developer replenisher is preferably 390 ml or less, more preferably from 30 to 325 ml, most preferably from 50 to 180 ml, per $m^2$ of the light-sensitive material. The developer replenisher may have the same composition and/or concentration as the development initiating solution or may have a different composition and/or concentration from the initiating solution.

Examples of the fixing agent in the fixing processing agent for use in the present invention include ammonium thiosulfate, sodium thiosulfate and ammonium sodium thiosulfate. The use amount of the fixing agent may be varied appropriately, however, it is generally from about 0.7 to about 3.0 mol/l.

The fixing solution for use in the present invention may contain a water-soluble aluminum salt or a water-soluble chromium salt which acts as a hardening agent, and of these, a water-soluble aluminum salt is preferred. Examples thereof include aluminum chloride, aluminum sulfate, potassium alum, ammonium aluminum sulfate, aluminum nitrate and aluminum lactate. These are each preferably contained, in terms of an aluminum ion concentration in the use solution, in an amount of from 0.01 to 0.15 mol/l.

When the fixing solution is stored as a concentrated solution or a solid agent, it may be constituted by a plurality of parts preparing a hardening agent or the like as a separate part or may be constituted as a one-part agent containing all components.

The fixing processing agent may contain, if desired, a preservative (e.g., sulfite, bisulfite, metabisulfite, in an amount of 0.015 mol/l or more, preferably from 0.02 to 0.3 mol/l), a pH buffer (e.g., acetic acid, sodium acetate, sodium carbonate, sodium hydrogencarbonate, phosphoric acid, succinic acid, adipic acid, in an amount of from 0.1 to 1 mol/l, preferably from 0.2 to 0.7 mol/l) or a compound having aluminum stabilizing ability or hard water softening ability (e.g., gluconic acid, iminodiacetic acid, 5-sulfosalicylic acid, glucoheptanoic acid, malic acid, tartaric acid, citric acid, oxalic acid, maleic acid, glycolic acid, benzoic acid, salicylic acid, Tiron, ascorbic acid, glutaric acid, aspartic acid, glycine, cysteine, ethylenediaminetetraacetic acid, nitrilotriacetic acid, a derivative and a salt thereof, saccharides, boric acid, in an amount of from 0.001 to 0.5 mol/l, preferably from 0.005 to 0.3 mol/l).

In addition, the fixing processing agent may contain a compound described in JP-A-62-78551, a pH adjusting agent (e.g., sodium hydroxide, ammonia, sulfuric acid), a surface active agent, a wetting agent or a fixing accelerator. Examples of the surface active agent include anionic surface active agents such as sulfated product and sulfonated product, polyethylene-base surface active agents, and amphoteric surface active agents described in JP-A-57-6840. A known defoaming agent may also be used. Examples of the wetting agent include alkanolamine and alkylene glycol. Examples of the fixing accelerator include alkyl- or aryl-substituted thiosulfonic acids and salts thereof described in JP-A-6-308681, thiourea derivatives described in JP-B-45-35754, JP-B-58-122535 and JP-B-58-122536, alcohols having a triple bond within the molecule, thioether compounds described in U.S. Pat. No. 4,126,459, mercapto compounds described in JP-A-64-4739, JP-A-1-4739, JP-A-1-159645 and JP-A-3-101728, meso-ionic compounds described in JP-A-4-170539 and thiocyanates.

The fixing solution for use in the present invention has a pH of 4.0 or more, preferably from 4.5 to 6.0. The pH of the fixing solution increases due to mingling of the developer upon processing and in this case, the hardening fixing solution has a pH of 6.0 or less, preferably 5.7 or less, and the non-hardening fixing solution has a pH of 7.0 or less, preferably 6.7 or less.

The replenishing amount of the fixing solution is 500 ml or less, preferably 390 ml or less, more preferably from 80 to 320 ml, per 1 $m^2$ of the light-sensitive material. The replenisher may have the same composition and/or concentration as the initiating solution or may have a composition and/or a concentration different from the initiating solution.

The fixing solution may be reused using a known fixing solution regeneration method such as electrolytic silver recovery. Examples of the regeneration apparatus include Reclaim R-60 manufactured by Fuji Hunt KK.

It is also preferred to remove dyes or the like through an adsorption filter such as activated carbon.

The light-sensitive material processed through development and fixing is then subjected to water washing or stabilization (hereinafter, unless otherwise specified, water washing includes stabilization and the solution for use therein is called water or washing water). The water for use in water washing may be tap water, ion exchanged water, distilled water or a stabilizing solution. The replenishing amount of the washing water is generally from about 8 to about 17 l per $m^2$ of the light-sensitive material, however, a replenishing amount lower than the above-described range may also be used. In particular, when the replenishing amount is 3 l or less (including 0, namely, standing water washing), not only the processing can achieve water savings but also the processing can dispense with piping for installation of an automatic developing machine. When water washing is performed with a small replenishing amount of water, a rinsing tank of squeeze roller or cross-over roller described in JP-A-63-18350 and JP-A-62-287252 is preferably provided. Or, addition of various oxidizing agents (e.g., ozone, hydrogen peroxide, sodium hypochlorite, active halogen, chlorine dioxide, sodium carbonate hydrogen peroxide salt) or filter filtration may be combined so as to reduce the pollution load which is a problem incurred in the case of water washing with a small amount of water or for preventing water scale.

As the method for reducing the replenishing amount of washing water, a multi-stage countercurrent system (for example, two stages or three stages) has been known for a long time, and the replenishing amount of washing water is preferably from 50 to 200 ml per $m^2$ of the light-sensitive material. This effect can also be obtained similarly in the case of an independent multi-stage system (a method of not using a countercurrent system but supplying a new solution individually to the multi-stage water washing tanks).

In the method in the present invention, a means for preventing water scale may be provided in the water washing step. The water scale preventing means is not particularly restricted and a known means may be used. Examples thereof include a method of adding a fungicide (so-called water scale inhibitor), a method of passing electricity, a method of irradiating ultraviolet rays, infrared rays or far infrared rays, a method of applying magnetic field, a method of treating with ultrasonic wave, a method of applying heat and a method of evacuating the tank on standing. The water scale preventing means may be applied according to the processing of the light-sensitive material, may be applied at a predetermined interval irrespective of the use state, or may be applied only in the period of non-processing time such as night time. Further, the washing water may be previously treated with a water scale preventing means and then replenished. Furthermore, in view of preventing generation of resistance microbes, it is preferred to perform different water scale preventing means every a predetermined period.

The fungicide is not particularly restricted and a known fungicide may be used. Examples thereof include, in addition to the above-described oxidizing agents, a glutaraldehyde, a chelating agent such as aminopolycarboxylic acid, a cationic surface active agent and a mercaptopyridine oxide (e.g., 2-mercaptopyridine-N-oxide), and a sole fungicide may be used or a plurality of fungicides may be used in combination.

The electricity may be passed according to the method described in JP-A-3-224685, JP-A-3-224687, JP-A-4-16280 or JP-A-4-18980.

In addition, a known water-soluble surface active agent or defoaming agent may be added so as to prevent uneven processing due to bubbling or to prevent transfer of stains. Further, a dye adsorbent described in JP-A-63-163456 may be provided in the water washing system so as to prevent stains due to a dye dissolved out from the light-sensitive material.

The overflow solution from the water washing step may be partly or wholly used by mixing it with the processing solution having fixing ability as described in JP-A-60-235133. It is also preferred in view of conservation of natural environment to reduce the biochemical oxygen demand (BOD), chemical oxygen demand (COD) or iodine consumption before discharge by subjecting the solution to microorganism treatment (for example, sulfur oxidation bacteria or activated sludge treatment or treatment with a filter comprising a porous carrier such as activated carbon or ceramic, having carried thereon microorganisms) or oxidation treatment by electrification or with an oxidizing agent, or to reduce silver concentration in waste water by passing the solution through a filter using a polymer having affinity for silver or by adding a compound which forms a difficultly soluble silver complex, such as trimercaptotriazine, to precipitate silver and then passing the solution through a filter.

In some cases, stabilization may be performed subsequent to the water washing and as one example, a bath containing the compound described in JP-A-2-201357, JP-A-2-132435, JP-A-1-102553 and JP-A-46-44446 may be used as a final bath of the light-sensitive material. This stabilization bath may also contain, if desired, an ammonium compound, a metal compound such as Bi or Al, a fluorescent brightening agent, various chelating agents, a layer pH adjusting agent, a layer hardening agent, a bactericide, a fungicide, an alkanolamine or a surface active agent.

The additives such as a fungicide and the stabilizing agent added to the water washing or stabilization bath may be formed into a solid agent similarly to the above-described development and fixing processing agents.

Waste water of the developer, the fixing solution, the washing water or the stabilizing solution for use in the present invention is preferably burned for disposal. The waste water can also be formed into a concentrated solution or a solid by a concentrating apparatus as described, for example, in JP-B-7-83867 and U.S. Pat. No. 5,439,560 and then disposed.

In the case when the replenishing amount of the processing agent is reduced, it is preferred to prevent evaporation or air oxidation of the solution by reducing the contact area of the processing tank with air. A roller transportation-type automatic developing machine is described in U.S. Pat. Nos. 3,025,779 and 3,545,971, and in the present invention, it is simply referred to as a roller transportation-type automatic processor. This automatic processor comprises four steps of development, fixing, water washing and drying, and it is most preferred to follow this four-step processing also in the present invention, though other steps (e.g., stopping step) are not rejected. Further, a rinsing bath may be provided between development and fixing and/or between fixing and water washing.

In the development in the present invention, the dry-to-dry time is preferably from 25 to 160 seconds, the development time and the fixing time each is 40 seconds or less, preferably from 6 to 35 seconds, and the temperature of each solution is preferably from 25 to 50° C., more preferably from 30 to 40° C. The temperature and the time of water washing are preferably from 0 to 50° C. and 40 seconds or less, respectively. According to the method in the present invention, the light-sensitive material after development, fixing and water washing may be passed through squeeze rollers for squeezing washing water and then dried. The drying is performed at a temperature of from about 40° C. to about 100° C. The drying time may be appropriately varied depending upon the ambient state. The drying method is not particularly restricted and any known method may be used, however, hot air drying, drying by a heat roller as disclosed in JP-A-4-15534, JP-A-5-2256 and JP-A-5-289294, and drying by far infrared rays may be used, and a plurality of drying methods may also be used in combination.

When the development or fixing processing solution for use in the present invention is a liquid agent, it is preferably stored in a packaging material having a low oxygen permeability described, for example, in JP-A-61-73147. Further, when these solutions each is a concentrated solution, it is diluted with water at a ratio such that the water is from 0.2 to 3 parts per 1 part of the concentrated solution, to have a predetermined concentration on use.

Even when the development processing agent or the fixing processing agent for use in the present invention is formed into a solid, the same effects as provided by the liquid agent can be obtained. The solid processing agent is described below.

The solid processing agent for use in the present invention may have a known shape (e.g., powder, grain, granule, lump, tablet, compactor, briquette, platy, stick, paste). The solid agent may be prepared by coating respective components with a water-soluble coating agent or film so as to separate components which react with each other on contacting, or may have a plural layer structure so as to separate components which react with each other. These techniques may also be used in combination.

The coating agent or the granulating aid used may be a known compound, however, polyvinyl pyrrolidone, polyethylene glycol, sulfonated polystyrene and a vinyl-base compound are preferred. In addition, JP-A-5-45805, from column 2, line 48 to column 3, line 13, may be referred to.

In the case where the solid agent has a plural layer structure, a component which does not react on contacting may be interposed between components which react with each other and the processing agent obtained may be formed into a tablet or a briquette. Or, the components each in a known shape may also be constituted into the same layer structure as above and then packaged. These methods are described, for example, in JP-A-61-259921, JP-A-4-16841, JP-A-4-78848 and JP-A-5-93991.

The solid processing agent preferably has a bulk density of from 0.5 to 6.0 g/cm$^3$, particularly in the case of a tablet, preferably from 1.0 to 5.0 g/cm$^3$ and in the case of a granule, from 0.5 to 1.5 g/cm$^3$.

The solid processing agent for use in the present invention may be prepared by any known method. The methods described, for example, in JP-A-61-259921, JP-A-4-15641, JP-A-4-16841, JP-A-4-32837, JP-A-4-78848, JP-A-5-93991, JP-A-4-85533, JP-A-4-85534, JP-A-4-85535, JP-A-5-134362, JP-A-5-197070, JP-A-5-204098, JP-A-5-224361, JP-A-6-138604, JP-A-6-138605 and JP-A-8-286329 may be used.

More specifically, a rolling granulation method, an extrusion granulation method, a compressive granulation method, a cracking granulation method, an agitating granulation method, a spray dry method, a dissolving coagulation method, a briquetting method or a roller compacting method may be used.

The solid agent for use in the present invention may be changed in the surface state (e.g., smooth, porous) or in the thickness partly, or may have a hollow doughnut form, to control the solubility. It is also possible to impart different solubilities to a plurality of granulated products or to have a plurality of shapes so as to harmonize the solubility of materials different in the solubility. Further, a granulated product comprising a plurality of layers and different in the composition between the surface and the inside may be used.

The packaging material for the solid agent is preferably a material having low permeability to oxygen and water. The shape of the packaging material may be a known form such as a bag, a cylinder or a box. Further, a shape capable of folding as disclosed in JP-A-6-242585 to JP-A-6-242588, JP-A-6-247432, JP-A-6-247448, JP-A-6-301189, JP-A-7-5664, JP-A-7-5666 to JP-A-7-5669 is also preferred so as to save the space for storing waste packaging materials. The packaging material may be fixed with, at the takeout port for the processing agent, a screw cap, a pull-top or an aluminum seal or may be heat sealed, however, this is not particularly limited and other known means may be used. The waste packaging material is preferably recycled or reused in view of environmental conservation.

The method for dissolving or replenishing the solid processing agent for use in the present invention is not particularly restricted and known methods may be used. Examples of the method include a method of dissolving a constant amount of solid processing agent in a dissolving apparatus having an agitation function and replenishing it, a method of dissolving a solid processing agent in a dissolving apparatus having a dissolving portion and a portion for stocking the finished solution and replenishing the solution from the stock portion, a method of charging a processing agent into a circulation system of an automatic developing machine and dissolving and replenishing it in the system as described in JP-A-5-119454, JP-A-6-19102 and JP-A-7-261357, and a method of charging and dissolving a processing agent according to the processing of a light-sensitive material in an automatic developing machine self-containing a dissolution tank. Other than these, any known method may be used. The charging of the processing agent may be performed manually or using automatic unsealing and automatic charging in a dissolving apparatus or automatic developing machine having an unsealing mechanism. In view of working environment, the latter is preferred. Specifically, a method of bursting, peeling off, cutting out or pushing away the takeout port and methods described in JP-A-6-19102 and JP-A-6-95331 may be used.

A preferred embodiment when the light-sensitive material of the present invention is used as a direct positive silver halide photographic light-sensitive material, is described below.

In this case, the compound represented by formula (I) can be made to function as a fogging agent. When the compound represented by formula (I) is used as a fogging agent, the compound is hereinafter referred to as a "fogging agent of the present invention".

It may be sufficient if at least one fogging agent of the present invention is rendered to be present so as to fog an internal latent image-type silver halide emulsion which is an emulsion of giving a direct positive image, upon development after imagewise exposure. More specifically, the fogging agent of the present invention may be incorporated into a light-sensitive material comprising an internal latent image-type silver halide emulsion so that the development can be performed in the presence of the fogging agent of the present invention after exposing the photographic light-sensitive material.

In a preferred practical embodiment, at least one fogging agent of the present invention is incorporated into a silver halide emulsion layer or a layer adjacent thereto (for example, a silver halide light-sensitive layer, an interlayer, a filter layer, a protective layer or an antihalation layer).

The use amount of the fogging agent of the present invention varies over a wide range depending on the characteristics of the silver halide emulsion used, the kind of the fogging agent and the development conditions, however, it may be sufficient if the use amount is large enough to give a fogging action to form a positive image on developing an imagewise exposed photographic material comprising an internal latent image-type silver halide emulsion with a surface developer. The use amount is preferably large enough to give a satisfactory maximum density (for example, 2.0 or more) after the development.

The fogging agent of the present invention is preferably incorporated into a silver halide emulsion at an appropriate period after completion of the ripening in an amount of approximately from $10^{-5}$ to $10^{-1}$ mol per mol of silver halide.

Examples of the silver halide development agent which can be used in developing a photographic material comprising an internal latent image-type silver halide emulsion for use in the present invention, include hydroquinones, catechols, aminophenols, 3-pyrazolidones, ascorbic acids and derivatives thereof, reductones, phenylenediamines and a mixture thereof. The development agent may also be previously incorporated into an emulsion to act on the silver halide during dipping in an aqueous solution having a high pH.

The developing composition for use in developing a direct positive silver halide photographic light-sensitive material, may further comprise an antifoggant and a development inhibitor. Alternatively, the antifoggant and a development inhibitor may be freely incorporated into a layer of a silver halide photographic light-sensitive material.

In the case when the present invention is applied to a direct positive silver halide photographic light-sensitive material, the silver halide emulsion is an internal latent image-type silver halide emulsion, namely, an emulsion having a latent image formed mainly in the inside of a silver halide grain and comprising silver halide grains where a majority of sensitization specks are present inside the grain. For the silver halide for forming this emulsion, any composition can be used similarly to those described above.

The emulsion used here is more preferably such that the maximum density obtained when a part of a sample comprising a transparent support having coated thereon the above-described emulsion is exposed to a light intensity scale over a predetermined time period up to about 1 second and then developed at 20° C. for 4 minutes with the following Surface Developer A which contains substantially no silver halide solvent and develops only the surface image of the grain, is not more than 1/5, preferably not more than 1/10, of the maximum density obtained when another part of the same emulsion sample is exposed and then developed at 20° C. for 4 minutes with the following internal developer B which develops the inside of the grain.

Surface Developer A:

| | |
|---|---|
| Metol | 2.5 g |
| L-Ascorbic acid | 10 g |
| $NaBO_2 \cdot 4H_2O$ | 20 g |
| KBr | 1 g |
| Water to make | 1 l |

Internal Developer B:

| | |
|---|---|
| Metol | 2.0 g |
| Sodium sulfite | 90.0 g |
| Hydroquinone | 8.0 g |
| Sodium carbonate hydrate | 52.5 g |
| KBr | 5.0 g |
| KI | 0.5 g |
| Water to make | 1 l |

The internal latent image-type silver halide emulsion includes emulsions prepared by various methods. Examples thereof include a conversion-type silver halide emulsion described in U.S. Pat. No. 2,592,250, a silver halide emulsion comprising silver halide grains of which inside is chemically sensitized described in U.S. Pat. Nos. 3,206,316, 3,317,322 and 3,367,778 and JP-B-43-29405, a silver halide emulsion comprising silver halide emulsion having incorporated therein a polyvalent metal ion described in U.S. Pat. Nos. 3,271,157, 3,447,927 and 3,531,291, and a silver halide emulsion comprising grains having a laminate structure described in JP-A-50-8524.

The internal latent image-type silver halide emulsion may further contain a compound having an azaindene ring or a nitrogen-containing heterocyclic compound having a mercapto group in an amount of preferably from 1 mg to 10 g per mol of silver halide and this can gives a higher stability effect with a lower minimum density.

The compound having an azaindene ring is preferably 4-hydroxy-6-methyl-1,3,3a,7-tetraazaindene. Examples of the nitrogen-containing heterocyclic compound having a mercapto group include a pyrazole ring, a 1,2,4-triazole ring, a 1,2,3-triazole ring, a 1,3,4-thiadiazole ring, a 1,2,3-thiadiazole ring, a 1,2,4-thiadiazole ring, a 1,2,5-thiadiazole ring, a 1,2,3,4-tetrazole ring, a pyridazine ring, a 1,2,3-triazine ring, a 1,2,4-triazine ring, a 1,3,5-triazine ring, a ring resulting from condensation of two or three of these rings, such as triazolotriazole ring, diazaindene ring, triazaindene ring, tetrazaindene ring and pentazaindene ring, a phthalazinone ring and an indazole ring. 1-Phenyl-5-mercaptotetrazole is preferred.

The silver halide photographic light-sensitive material of the present invention, particularly when applied to a positive light-sensitive material, may be either a black-and-white photographic light-sensitive material or a monochromatic or polychromatic color photographic light-sensitive material. In the case of a full color light-sensitive material, the photographic light-sensitive material is preferably constituted to have a blue-sensitive layer, a green-sensitive layer and a red-sensitive layer. In this case, the photographic light-sensitive formed usually comprises a yellow coupler-containing blue-sensitive silver halide emulsion layer, a magenta coupler-containing green-sensitive silver halide emulsion layer and a cyan coupler-containing red-sensitive silver halide emulsion layer.

In one preferred embodiment, the layer structure is such that a blue-sensitive layer, a green-sensitive layer and a red-sensitive layer are provided in this order from the side farther from the support, and a light-insensitive layer (yellow filter layer) is provided between the blue-sensitive layer and the green-sensitive layer.

As the yellow coupler, known acylacetanilide-base couplers can be used, and benzoylacetanalide-base and pivaloylacetanilide-base compounds are particularly suitable.

As the magenta coupler, 5-pyrazolone-base couplers, pyrazoloazole-base couplers and open chain acylacetonitile-base couplers can be used.

A the cyan coupler, naphthol-base couplers and phenol-base couplers can be preferably used.

As described above, light-sensitive silver halide emulsion layers and a light-insensitive layer as a yellow filter layer are provided on a support, and in addition, a large number of various photographic constituent layers such as an interlayer, a protective layer, a subbing layer, a back subbing layer and an antihalation layer, can also be provided on the support. These layers can be coated by a dip coating method, an air doctor coating method, an extrusion coating method, a slide hopper coating method or a curtain flow coating method.

In the case of a direct positive silver halide photographic light-sensitive material, examples of the support thereof include polyethylene terephthalate film, polycarbonate film, polystyrene film, polypropylene film, cellulose acetate film, glass, baryta paper and polyethylene laminate paper, subjected, if desired, to subbing.

The support may be either opaque or transparent, and this can be selected according to the desired light-sensitive material.

The silver halide emulsion of the light-sensitive material may contain a lubricant, a layer physical property improving agent or a coating aid depending on the purpose. Further, the silver halide emulsion can contain other photographic additives such as a gelatin plasticizer, a surface active agent, an ultraviolet absorbent, a pH adjusting agent, an antioxidant, an antistatic agent, a thickening agent, a granularity improving agent, a dye, a mordant, a brightening agent, a development rate controlling agent an a matting agent.

It is useful to use an ultraviolet absorbent such as thiazolidone, benzotriazole, acrylonitrile or a benzophenone-base compound, for preventing discoloration of the dye image due to active rays of short wavelength.

The silver halide emulsion layer can use gelatin or other appropriate gelatin derivative suitable for the purpose, as a protective colloid or a binder. The silver halide emulsion layer can also contain other hydrophilic binder depending on the purpose. This can be added to the emulsion layer or photographic constituent layers such as an interlayer, a protective layer, a filter layer or a back subbing layer, of the above-described photographic light-sensitive layer. Further, the hydrophilic binder can contain an appropriate plasticizer or lubricant according to the purpose.

Each constituent layer can be hardened by any appropriate hardening agent.

The light-sensitive material can also use an antistaining agent.

The present invention is described in more detail with reference to the following Examples, but the invention should not be construed as being limited thereto.

EXAMPLE 1

Preparation of Solid Dispersion of Hydrazine Compound

A 25% aqueous solution of Demole SNB (produce by Kao Corporation) was prepared. Then, to 0.5 g of a hydrazine compound shown in Table 11, 0.6 g of the Demole SNB aqueous solution prepared above and 59 g of water were added to form a slurry. The resulting slurry was charged in a dispersing machine (1/16 gallon, Sand Grinder Mill (manufactured by Imex KK)) and dispersed for 15 hours using, as the media, 170 g of glass beads having a diameter of from 0.8 to 1.2 mm. Thereafter, an aqueous gelatin solution was added and mixed to give a hydrazine compound concentration of 0.5% and a gelatin concentration of 5%, and then proxel as an antiseptic was added in an amount of 2,000 ppm based on the gelatin. Finally, an ascorbic acid was added to adjust the pH to 5.0. The average particle size of each solid dispersion of hydrazine compound is shown in Table 14.

For comparison with the hydrazine compound of the present invention, the following hydrazine compounds were used.

Comparative Compound 1

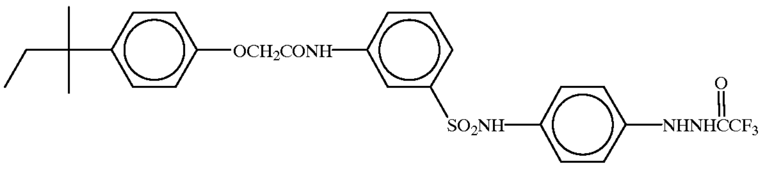

Comparative Compound 2

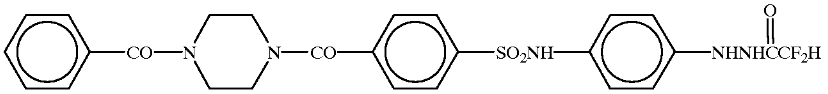

-continued

Comparative Compound 3

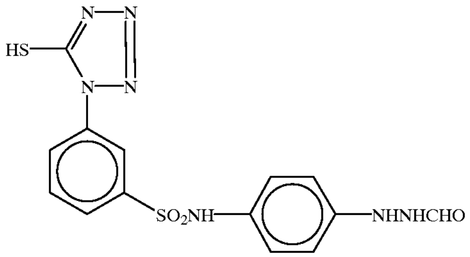

Comparative Compound 4

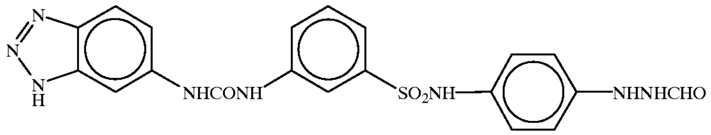

Comparative Compound 5

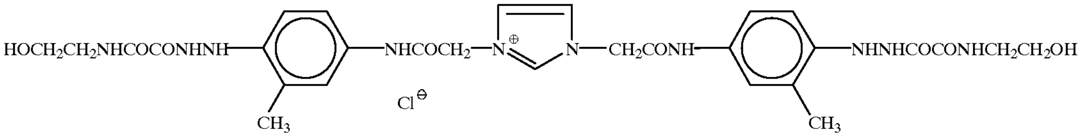

(compound described in WO 95/32453)

Comparative Compound 6

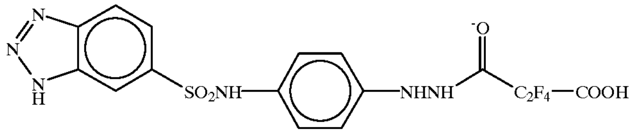

Comparative Compound 7

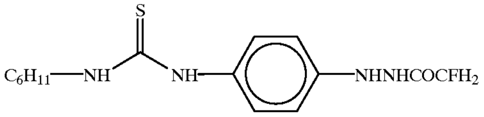

(compound described in U. S. Patent 5,252,426)

TABLE 14

| Solid Dispersion No. | Hydrazine Compound | Average Particle Size (μm) |
|---|---|---|
| K-1 | Comparative Compound 1 | 0.21 |
| K-2 | Comparative Compound 2 | 0.40 |
| K-3 | Comparative Compound 3 | 0.46 |
| K-4 | Comparative Compound 4 | 0.36 |
| K-5 | Comparative Compound 5 | 0.38 |
| K-6 | Comparative Compound 6 | 0.40 |
| K-7 | Comparative Compound 7 | 0.39 |
| K-8 | 4b | 0.43 |
| K-9 | 17b | 0.46 |
| K-10 | 21b | 0.39 |
| K-11 | 5b | 0.40 |
| K-12 | 6b | 0.39 |
| K-13 | 13b | 0.49 |
| K-14 | 10b | 0.50 |
| K-15 | 41c | 0.50 |
| K-16 | 4c | 0.39 |
| K-17 | 17c | 0.40 |
| K-18 | 21c | 0.45 |
| K-19 | 5c | 0.38 |
| K-20 | 6c | 0.38 |
| K-21 | 13c | 0.44 |
| K-22 | 10c | 0.37 |
| K-23 | 41b | 0.44 |

EXAMPLE 2

Preparation of Silver Halide Photographic Light-Sensitive Material

Preparation of Emulsion A

An aqueous silver nitrate solution and an aqueous halogen salt solution containing potassium bromide, sodium chloride, $K_3IrCl_6$ corresponding to $3.5\times10^{-7}$ mol/mol-Ag and $K_2Rh(H_2O)Cl_5$ corresponding to $2.0\times10^{-7}$ mol/mol-Ag, were added to an aqueous gelatin solution containing sodium chloride and 1,3-dimethyl-2-imidazolidinethione, while stirring by a double jet method to prepare silver chlorobromide grains having an average grain size of 0.25 μm and a silver chloride content of 70 mol %.

Thereafter, the emulsion was washed with water by flocculation according to a usual method, 40 g/mol-Ag of gelatin was added thereto, then 7 mg/mol-Ag of sodium benzenethiosulfonate and 2 mg/mol-Ag of sodium benzenesulfinate were further added, and the pH and the pAg were adjusted to 6.0 and 7.5, respectively. Thereto, 2 mg/mol-Ag of sodium thiosulfate and 4 mg/mol-Al of chloroauric acid were added, and the mixture was subjected to chemical sensitization to have an optimal sensitivity at 60° C. Then, 150 mg of 4-hydroxy-6-methyl-1,3,3a,7-tetraazaindene as a stabilizer and 100 mg of proxel as an antiseptic were added. The resulting grains were silver chlorobromide cubic grains having an average grain size of 0.25 μm and a silver chloride content of 70 mol % (coefficient of variation: 10%).

Preparation of Coated Sample:

On a polyethylene terephthalate film support undercoated by a moisture-proofing layer containing vinylidene chloride, a UL layer, an EM layer, a PC layer and an OC layer were coated in this order from the support side to prepare a sample.

The preparation method and the coating amount of each layer are described below.

(UL Layer)

To an aqueous gelatin solution, a dispersion of polyethyl acrylate was added in an amount of 30 wt % based on the gelatin and the mixture was coated to have a gelatin coverage of 0.5 g/m$^2$.

(EM Layer)

To Emulsion A prepared above, 5x10$^{-4}$ mol/mol-Ag of Compound (S-1) shown below and 5x10$^{-4}$ mol/mol-Ag of Compound (S-2) shown below were added as sensitizing dyes, and further 3x10$^{-4}$ mol/mol-Ag of a mercapto compound shown below as Compound (a), 4x10$^{-4}$ mol/mol-Ag of a mercapto compound shown below as Compound (b), 4x10$^{-4}$ mol/mol-Ag of a triazine compound shown below as Compound (c), 2x10$^{-3}$ mol/mol-Ag of 5-chloro-8-hydroxyquinoline, 5x10$^{-4}$ mol/mol-Ag of a nucleation accelerator shown below as Compound (A) and 5x10$^{-4}$ mol/mol-Ag of a surface active agent shown below as Compound (p) were added. Furthermore, hydroquinone and N-oleyl-N-methyltaurine sodium salt were added to give a coated amount of 100 mg/M$^2$ and 30 mg/M$^2$, respectively. Then, a solid dispersion of hydrazine compound prepared in Example 1 as a nucleating agent was added as shown in Table 15 in an amount of 5x10$^{-3}$ mol/mol-Ag in terms of the hydrazine compound. Further, 200 mg/m$^2$ of a water-soluble latex shown below as Compound (d), 200 mg/m$^2$ of a polyethyl acrylate latex dispersion, 200 mg/m$^2$ of a latex copolymer of methyl acrylate, sodium 2-acrylamido-2-methylpropanesulfonate and 2-acetoacetoxyethyl methacrylate (weight ratio: 88:5:7), 200 mg/m$^2$ of colloidal silica having an average particle size of 0.02 μm, 200 mg/m$^2$ of 1,3-divinylsulfonyl-2-propanol as a hardening agent and 30 mg/m$^2$ of sodium polystyrenesulfonate as a thickener were added. The resulting solution was adjusted to have a pH of 5.5 using an acetic acid. Then, the solution was coated to have a coated silver amount of 2.5 g/m$^2$.

(PC Layer)

To an aqueous gelatin solution, a dispersion of ethyl acrylate was added in an amount of 50 wt % based on the gelatin. Thereto, Surface Active Agent (w) shown below and 1,5-dihydroxy-2-benzaldoxime were added to give a coated amount of 5 mg/m$^2$ and 10 mg/m$^2$, respectively. The resulting mixed solution was coated to give a gelatin coverage of 0.5 g/m$^2$.

(OC Layer)

The layer was provided by coating 0.5 g/m$^2$ of gelatin, 40 mg/m$^2$ of an amorphous $SiO_2$ matting agent having an average particle size of about 3.5 μm, 0.1 g/m$^2$ of methanol silica, 100 mg/m$^2$ of polyacrylamide, 20 mg/m$^2$ of silicone oil, and as coating aids, 5 mg/m$^2$ of a fluorine surface active agent shown by the following structural formula (e) and 100 mg/m$^2$ of sodium dodecylbenzenesulfonate.

(S-1)

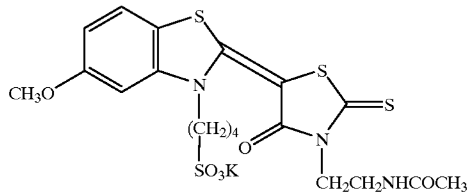

(S-2)

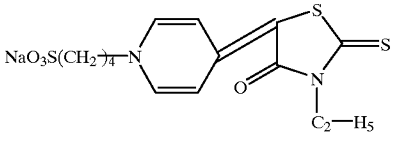

(a)

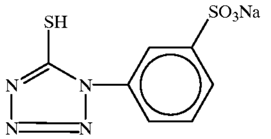

(b)

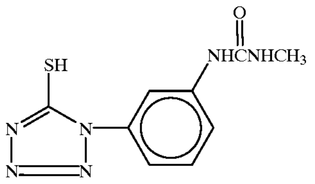

(c)

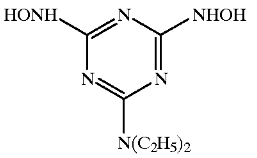

(A)

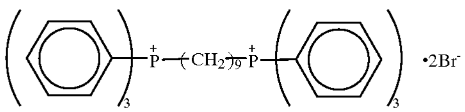

(p)

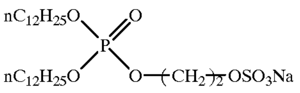

(d)

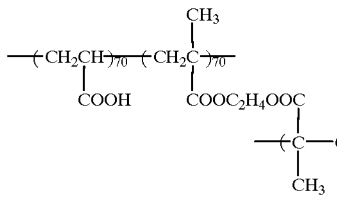

(e)

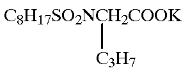

-continued (w)

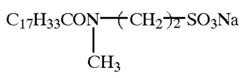

The thus-obtained coated samples each had a back layer and a back protective layer having the following compositions.

Formulation of Back Layer:

| | | |
|---|---|---|
| Gelatin | 3 | g/m$^2$ |
| Latex: Polyethyl acrylate | 2 | g/m$^2$ |
| Surface active agent: | | |
| Sodium p-dodecylbenzenesulfonate | 40 | mg/m$^2$ |
| 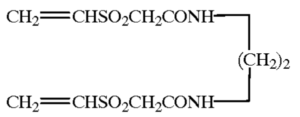 | 110 | mg/m$^2$ |
| $SnO_2$/Sb (weight ratio: 90/10, average particle size: 0.20 μm) | 200 | mg/m$^2$ |
| Dye: Mixture of Dye [a], Dye [b] and Dye [c] | | |
| Dye [a] | 70 | mg/m$^2$ |
| Dye [b] | 70 | mg/m$^2$ |
| Dye [c] | 90 | mg/m$^2$ |

Dye [a]

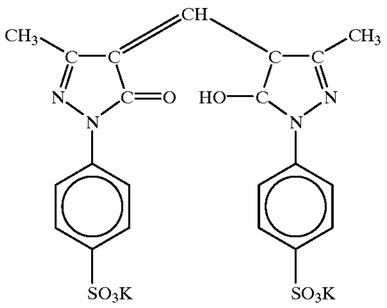

Dye [b]

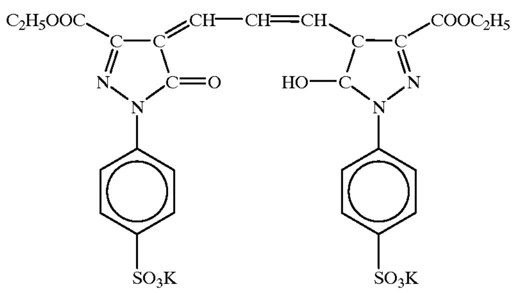

-continued

Dye [c]

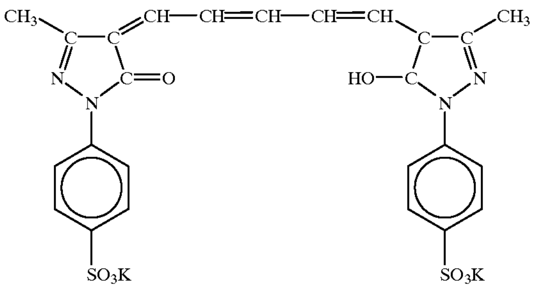

Back Protective Layer:

| | |
|---|---|
| Gelatin | 0.8 mg/m$^2$ |
| Polymethyl methacrylate fine particles (average particle size: 4.5 μm) | 30 mg/m$^2$ |
| Sodium dihexyl-α-sulfosuccinate | 15 mg/m$^2$ |
| Sodium p-dodecylbenzenesulfonate | 15 mg/m$^2$ |
| Sodium acetate | 40 mg/m$^2$ |

Samples shown in Table 15 were prepared as described above.

TABLE 15

| Sample No. | Solid Dispersion of Hydrazine Compound | Remarks |
|---|---|---|
| 1-1 | K-1 | Comparison |
| 1-2 | K-2 | Comparison |
| 1-3 | K-3 | Comparison |
| 1-4 | K-4 | Comparison |
| 1-5 | K-5 | Comparison |
| 1-6 | K-6 | Comparison |
| 1-7 | K-7 | Comparison |
| 1-8 | K-8 | Invention |
| 1-9 | K-9 | Invention |
| 1-10 | K-10 | Invention |
| 1-11 | K-11 | Invention |
| 1-12 | K-12 | Invention |
| 1-13 | K-13 | Invention |
| 1-14 | K-14 | Invention |
| 1-15 | K-15 | Invention |

Preparation of Developer:

Developer A having the following composition was prepared.

Developer A:

| | |
|---|---|
| Sodium hydroxide | 1.71 g |
| Diethylenetriaminepentaacetic acid | 4 g |
| Potassium carbonate | 33 g |
| Sodium carbonate | 30 g |
| Sodium erythorbate | 45 g |
| N-Methyl-p-aminophenol | 7.5 g |
| KBr | 2 g |
| 5-Methylbenzotriazole | 0.1 g |
| 1-Phenyl-5-mercaptotetrazole | 0.02 g |
| Sodium sulfite | 2 g |
| Glacial acetic acid | 9 g |
| Water to make | 1 l |
| pH adjusted to | 9.7 |

Developer B and Developer C were prepared by adding an acetic acid to Developer A to adjust the pH to 9.2 and adding sodium hydroxide to Developer A to adjust the pH to 10, respectively.

Evaluation:

(1) Exposure and Development

The thus-prepared samples each was exposed to a xenon flash light through a step wedge via an interference filter having a peak at 488 nm for an emission time of $10^{-5}$ sec and then developed with Developer A, Developer B or Developer C at 35° C. for 15 seconds in an automatic developing machine AP-560 manufactured by Fuji Photo Film Co., Ltd., followed by fixing, water washing and drying. In the processing, the developer and the fixing solution were replenished in an amount of 100 ml and 150 ml, respectively, per 1 $m^2$ of the sample.

Fixing Solution A having the following formulation was used as the fixing solution.

Fixing Solution A:

| | |
|---|---|
| Ammonium thiosulfate | 119.7 g |
| Disodium ethylenediaminetetraacetate dihydrate | 0.03 g |
| Sodium thiosulfate pentahydrate | 10.9 g |
| Sodium sulfite | 25.0 g |
| NaOH (as purity) | 12.4 g |
| Glacial acetic acid | 29.1 g |
| Tartaric acid | 2.92 g |
| Sodium gluconate | 1.74 g |
| Aluminum sulfate | 8.4 g |
| pH (adjusted by sulfuric acid or sodium hydroxide) | 4.8 |
| Water to make | 1 l |

(2) Contrast

The contrast obtained on development with Developer A was expressed as follows. With respect to the index (γ) for showing the contrast of an image, a point giving fog+density of 0.1 and a point giving fog+density of 3.0 on a characteristic curve were connected by a straight line and the gradient of the straight line was shown as the γ value. In other words, γ=(3.0-0.1)/[log(exposure amount necessary for giving density of 3.0)−(exposure amount necessary for giving density of 0.1)], and the larger the γ value, the higher the contrast.

(3) Photographic Sen sitivity ($S_{1.5}$)

The sensitivity was expressed by a logarithmic value of the exposure amount necessary for giving a density of 1.5. The smaller the value, the higher the sensitivity.

(4) Dependency of Photographic Property on pH of Developer

Using the sensitivity values obtained on development with Developer B and with Develop er C, dependency of the sensitivity on the pH of the developer was calculated according to the following formula:

pH Dependency of sensitivity ($\Delta S_{1.5}$)=$S_{1.5}$ (Developer B)−$S_{1.5}$ (Developer C)

The closer to 0 the value, the smaller the dependency on pH of the developer, that is, the higher the processing stability.

(5) Aging Stability of Light-Sensitive Material

Samples stored at a temperature of 60° C. and a humidity of 65% for 3 days each was developed with Developer A according to the above-described method, and the sensitivity was measured. The change in the photographic property between the sample obtained above and the sample stored at room temperature and normal humidity for 3 days was determined according to the following formula:

Change in sensitivity due to aging ($\Delta S_{1.5}$)=$S_{1.5}$ (sample stored at a temperature of 60° C. and a humidity of 65% for 3 days)−$S_{1.5}$ (sample stored at room temperature and normal humidity for 3 days)

The closer to 0 the value, the higher the aging stability of the light-sensitive material.

The results obtained are shown in Table 16.

TABLE 16

| Sample No. | γ | Dependency on pH of Developer ($\Delta S_{1.5}$) | Aging Stability of Light-Sensitive Material ($\Delta S_{1.5}$) | Remarks |
|---|---|---|---|---|
| 1-1 | 12 | 0.29 | 0.01 | Comparison |
| 1-2 | 13 | 0.35 | 0.17 | Comparison |
| 1-3 | 10 | 0.16 | 0.07 | Comparison |
| 1-4 | 10 | 0.19 | 0.07 | Comparison |
| 1-5 | 12 | 0.17 | 0.08 | Comparison |
| 1-6 | 12 | 0.18 | 0.06 | Comparison |
| 1-7 | 13 | 0.20 | 0.09 | Comparison |
| 1-8 | 19 | 0.07 | 0.01 | Invention |
| 1-9 | 19 | 0.06 | 0.01 | Invention |
| 1-10 | 18 | 0.06 | 0.01 | Invention |
| 1-11 | 16 | 0.09 | 0.02 | Invention |
| 1-12 | 19 | 0.06 | 0.01 | Invention |
| 1-13 | 17 | 0.08 | 0.02 | Invention |
| 1-14 | 17 | 0.08 | 0.02 | Invention |
| 1-15 | 20 | 0.05 | 0.01 | Invention |

Results:

Only when the hydrazine compound of the present invention was used as a nucleating agent, a light-sensitive material for argon laser scanner, having ultrahigh contrast, high processing stability and excellent storage stability of the light-sensitive material could be obtained with a developer having a low pH.

EXAMPLE 3

Preparation of Silver Halide Photographic Light-Sensitive Material

Preparation of Emulsion:

Emulsion B was prepared as follows.

Emulsion B was prepared in the same manner as Emulsion A except for performing chemical sensitization to have optimal sensitivity at 60° C. by adding 1 mg/mol-Ag of a selenium sensitizer having the following structural formula, 1 mg/mol-Ag of sodium thiosulfate and 4 mg/mol-Ag of chloroauric acid.

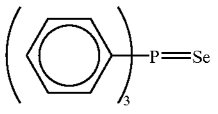

Preparation of Coated Sample:

Samples were prepared in the same manner as in Example 2 except for adding $2.1\times10^{-4}$ mol/mol-Ag of Compound (S-3) shown below in place of the sensitizing dye in the EM Layer in Example 2 and using Emulsion B as the emulsion in the EM Layer.

(S-3)

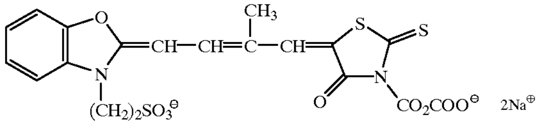

Evaluation:

(1) Exposure and Development

The thus-prepared samples each was exposed to a xenon flash light through a step wedge via an interference filter having a peak at 633 nm for an emission time of $10^{-6}$ sec. Then, samples each was developed with Developer A described in Example 2 at 35° C. for 15 seconds in an automatic developing machine AP-560 manufactured by Fuji Photo Film Co., Ltd., and subjected to fixing (same as in Example 2), water washing and drying. In the processing, the developer and the fixing solution each was replenished in an amount of 100 ml per 1 $m^2$ of the sample.

Evaluation of the contrast, the dependency of sensitivity on pH of the developer and the aging stability of the light-sensitive material was performed in the same manner as in Example 2.

Results:

Similarly to Example 2, only when the hydrazine compound of the present invention was used as a nucleating agent, a light-sensitive material for helium-neon laser scanner, having ultrahigh contrast, high processing stability and excellent storage stability of the light-sensitive material could be obtained with a developer having a low pH.

EXAMPLE 4

Preparation of Silver Halide Photographic Light-Sensitive Material

Samples were prepared in the same manner as in Example 2 except for using Compound (S-4) shown below in place of the sensitizing dye in the EM Layer in Example 2.

(S-4)

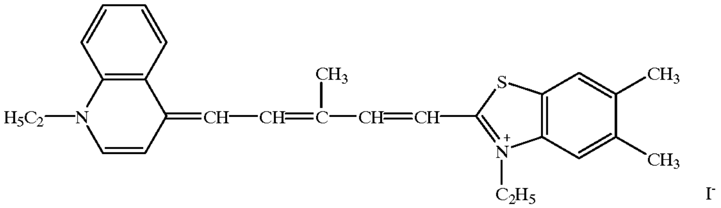

Evaluation:

The thus-prepared samples each was exposed to a xenon flash light through a step wedge via an interference filter having a peak at 780 nm for an emission time of $10^{-6}$ sec. Then, samples each was developed with Developer A described in Example 2 at 35° C. for 15 seconds in an automatic developing machine AP-560 manufactured by Fuji Photo Film Co., Ltd., and subjected to fixing (same as in Example 2), water washing and drying. In the processing, the developer and the fixing solution each was replenished in an amount of 100 ml per 1 $m^2$ of the sample.

Evaluation of the contrast, the dependency of sensitivity on pH of the developer and the aging stability of the light-sensitive material was performed in the same manner as in Example 2.

Results:

Similarly to Example 2, only when the hydrazine compound of the present invention was used as a nucleating agent, a light-sensitive material for semiconductor laser scanner, having ultrahigh contrast, high processing stability and excellent storage stability of the light-sensitive material could be obtained with a developer having a low pH.

EXAMPLE 5

Preparation of Silver Halide Photographic Light-Sensitive Material

Samples were prepared in the same manner as in Example 2 except for using Compound (S-5) shown below in place of the sensitizing dye in the EM Layer in Example 2.

(S-5)

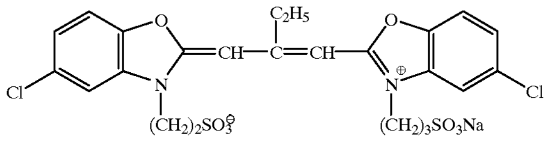

Evaluation:

The thus-prepared samples each was exposed to a tungsten light at 3,200° K. through a step wedge. Then, samples each was developed with Developer A described in Example 2 at 35° C. for 15 seconds in an automatic developing machine AP-560 manufactured by Fuji Photo Film Co., Ltd., and subjected to fixing (same as in Example 2), water washing and drying. In the processing, the developer and the fixing solution each was replenished in an amount of 100 ml per 1 $m^2$ of the sample.

Evaluation of the contrast, the dependency of sensitivity on pH of the developer and the aging stability of the light-sensitive material was performed in the same manner as in Example 2.

Results:

Similarly to Example 2, only when the hydrazine compound of the present invention was used as a nucleating agent, a light-sensitive material for photographing, having ultrahigh contrast, high processing stability and excellent storage stability of the light-sensitive material could be obtained with a developer having a low pH.

EXAMPLE 6

Preparation of Silver Halide Photographic Light-Sensitive Material

Preparation of Emulsion C:

To a 1.5% aqueous gelatin solution kept at 38° C., containing sodium chloride, $3\times10^{-5}$ mol/mol-Ag of Compound Z shown below and $5\times10^{-3}$ mol/mol-Ag of 4-hydroxy-6-methyl-1,3,3a,7-tetrazaindene, and having a pH of 2.0, an aqueous silver nitrate solution and an aqueous sodium chloride solution containing $5\times10^{-5}$ mol/mol-Ag of $K_2Ru(NO)Cl_5$ were added simultaneously in an amount of consuming a half of the silver amount of a final grain by a double jet method at an electric potential of 95 mV over 3 minutes and 30 seconds to prepare core grains having a size of 0.12 μm. Thereafter, an aqueous silver nitrate solution and an aqueous sodium chloride solution containing $5\times10^{-5}$ mol/mol-Ag of $K_2Ru(NO)Cl_5$ were added in the same manner as above over 7 minutes to prepare silver chloride cubic grains having an average grain size of 0.13 μm (coefficient of variation: 12%).

Thereafter, the emulsion was washed with water by flocculation well known in the art to remove soluble salts, then gelatin was added, Compound Z and phenoxyethanol as antiseptics were added each in an amount of 60 mg/mol-Ag, the pH and the pAg were adjusted to 5.5 and 7.5, respectively, further $4\times10^{-5}$ mol/mol-Ag of chloroauric acid, $1\times10^{-5}$ mol/mol-Ag of the above-described selenium sensitizer and $1\times10^{-5}$ mol/mol-Ag of sodium thiosulfate were added, the mixture was heated at 60° C. for 60 minutes to perform chemical sensitization, and then $1\times10^{-3}$ mol/mol-Ag of 4-hydroxy-6-methyl-1,3,3a,7-tetrazaindene as a stabilizer was added (the final grain was silver chloride having a pH of 5.7 and a pAg of 7.5 and containing $5\times10^{-5}$ mol/mol-Ag of Ru). Compound Z:

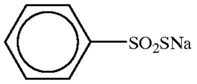

Preparation of Coated Sample:

Silver Halide Emulsion Layer:

To Emulsion C, the following compounds were added, and the mixture was coated on a support having an undercoat layer, which will be described later, to provide a silver halide emulsion layer having a gelatin coated amount of 0.9 g/m$^2$ and a coated silver amount of 2.75 g/m$^2$.

| | |
|---|---|
| N-Oleyl-N-methyltaurine sodium salt | 19 mg/m$^2$ |
| Solid dispersion of hydrazine compound prepared in Example 1, shown in Table 14 (hydrazine compound basis) | 30 mg/m$^2$ |
| Nucleation Accelerator Z | 20 mg/m$^2$ |
| Sodium 3-(5-mercaptotetrazole)-benzenesulfonate | 11 mg/m$^2$ |
| Compound A | 13 mg/m$^2$ |
| Ascorbic acid | 1 mg/m$^2$ |
| Compound B | 15 mg/m$^2$ |
| Compound C | 70 mg/m$^2$ |
| Acetic acid | in an amount of giving the layer surface pH of from 5.2 to 6.0 |
| Compound D | 950 mg/m$^2$ |
| Compound E (hardening agent) | in an amount of giving a swelling rate with water of 80% |

On the thus-provided emulsion layer, emulsion protective lower and upper layers were coated.

Emulsion Protective Lower Layer:

To an aqueous gelatin solution, the following compounds were added and the solution was coated to give a gelatin coated amount of 0.8 g/m$^2$.

| | |
|---|---|
| Gelatin ($Ca^{++}$ content: 2,700 ppm) | 0.8 g/m$^2$ |
| Compound F | 1 mg/m$^2$ |
| 1,5-Dihydroxy-2-benzaldoxime | 14 mg/m$^2$ |
| $C_2H_5SO_2SNa$ | 3 mg/m$^2$ |
| Compound C | 3 mg/m$^2$ |
| Sodium p-dodecylbenzenesulfonate | 7 mg/m$^2$ |
| Water-soluble Dye Y | 25 mg/m$^2$ |

Preparation of Coating Solution for Emulsion Protective Upper Layer and Coating of the Solution:

To an aqueous gelatin solution, the following compounds were added, and the solution was coated to give a gelatin coated amount of 0.45 g/m$^2$.

| | |
|---|---|
| Gelatin ($Ca^{++}$ content: 2,700 ppm) | 0.45 g/m$^2$ |
| Amorphous silica matting agent (average particle size: 4.4 μm) | 40 mg/m$^2$ |
| Amorphous silica matting agent (average particle size: 3.6 μm) | 10 mg/m$^2$ |
| Compound F | 1 mg/m$^2$ |
| Compound C | 8 mg/m$^2$ |
| Solid Disperse Dye $G_1$ | 68 mg/m$^2$ |
| Liquid paraffin | 21 mg/m$^2$ |
| Potassium N-perfluoroctanesulfonyl-N-propylglycine | 5 mg/m$^2$ |
| Sodium p-dodecylbenzenesulfonate | 29 mg/m$^2$ |

Then, on the opposite surface of the support, an electrically conductive layer and a back layer described below were coated simultaneously.

Electrically Conductive Layer:

To an aqueous gelatin solution, the following compounds were added, and the solution was coated to give a gelatin coated amount of 0.06 g/m$^2$.

| | |
|---|---|
| $SnO_2$/Sb (9/1 by weight, average particle size: 0.25 μm) | 186 mg/m$^2$ |
| Gelatin ($Ca^{++}$ content: 2,700 ppm) | 0.06 mg/m$^2$ |
| Sodium p-dodecylbenzenesulfonate | 13 mg/m$^2$ |
| Sodium dihexyl-α-sulfosuccinate | 12 mg/m$^2$ |
| Compound C | 12 mg/m$^2$ |
| Compound F | 1 mg/m$^2$ |

Back Layer:

To an aqueous gelatin solution, the following compounds were added, and the solution was coated to give a gelatin coated amount of 1.94 g/m$^2$.

| | |
|---|---|
| Gelatin ($Ca^{++}$ content: 30 ppm) | 1.94 g/m$^2$ |
| Polymethyl methacrylate fine particle (average particle size: 4.7 μm) | 7 mg/m$^2$ |
| Compound H | 233 mg/m$^2$ |
| Compound I | 21 mg/m$^2$ |
| Compound G | 146 mg/m$^2$ |
| Compound F | 3 mg/m$^2$ |
| Sodium p-dodecylbenzenesulfonate | 68 mg/m$^2$ |
| Sodium dihexyl-α-sulfosuccinate | 21 mg/m$^2$ |
| $C_8F_{17}SO_3Li$ | 4 mg/m$^2$ |
| Potassium N-perfluoroctanesulfonyl-N-propylglycine | 6 mg/m$^2$ |
| Sodium sulfate | 177 mg/m$^2$ |
| Compound E (hardening agent) | in an amount of giving a swelling rate with water of 90% |

Support and Undercoat Layer:

On both surfaces of a biaxially stretched polyethylene terephthalate support (thickness: 100 μm), undercoat first and second layers each having the following composition were coated.

Undercoat First Layer:

| | |
|---|---|
| Core-shell Type Vinylidene Chloride Copolymer (1) | 15 g |
| 2,4-Dichloro-6-hydroxy-s-triazine | 0.25 g |
| Polystyrene fine particle (average particle size: 3 μm) | 0.05 g |
| Compound M | 0.20 g |
| Colloidal silica (Snowtex ZL, | 0.12 g |

-continued

| | |
|---|---|
| produced by Nissan Chemical KK, particle size: 70 to 100 μm) | |
| Water to make | 100 g |

Further, the coating solution was adjusted to have a pH of 6 by adding 10 wt % of KOH and coated to have a dry thickness of 0.9 μm at a drying temperature of 180° C. within 2 minutes.

Undercoat Second Layer:

| | |
|---|---|
| Gelatin | 1 g |
| Methyl cellulose | 0.05 g |
| Compound J | 0.02 g |
| $C_{12}H_{25}O(CH_2CH_2O)_{10}H$ | 0.03 g |
| Compound F | $3.5 \times 10^{-3}$ g |
| Acetic acid | 0.2 g |
| Water to make | 100 g |

The thus-obtained coating solution was coated to have a dry thickness of 0.1 μm at a drying temperature of 170° C. within 2 minutes. Thus, a support having undercoat layers was prepared.

Nucleation Accelerator Z:

Nucleation Accelerator Z:

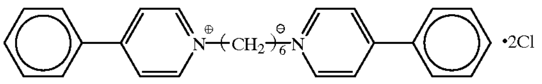

Compound A:

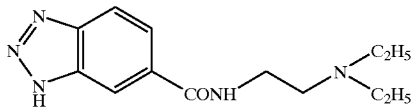

Compound B:

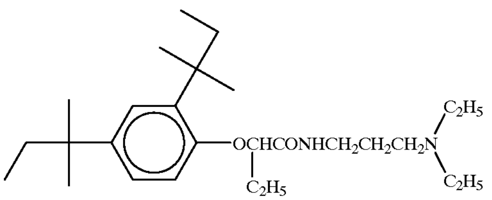

Compound C:

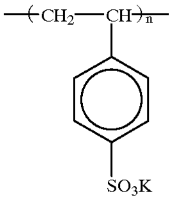

Compound D:

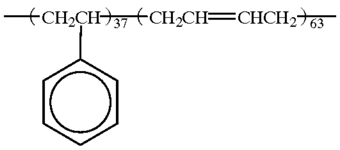

core/shell = 50/50
(core part: Sr/Bu = 37/63)

-continued

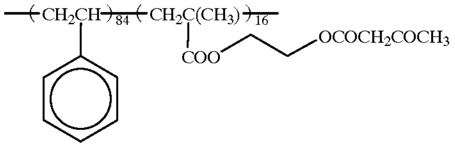

(shell part: St/AAEMA = 84/16)

Compound E:

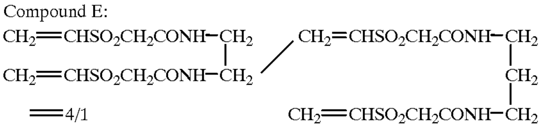

Compound F:

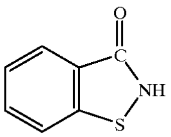

Compound G:

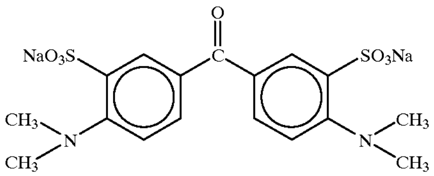

Solid Disperse Dye $G_1$:

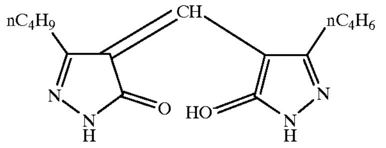

Compound H:

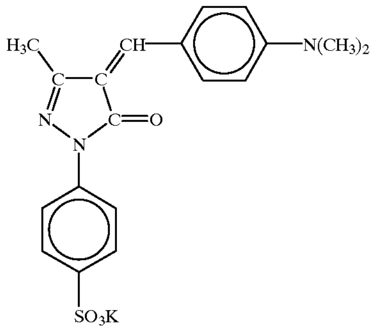

Water Soluble Dye Y:

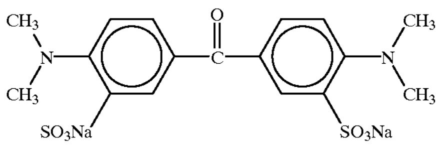

-continued

Compound I:

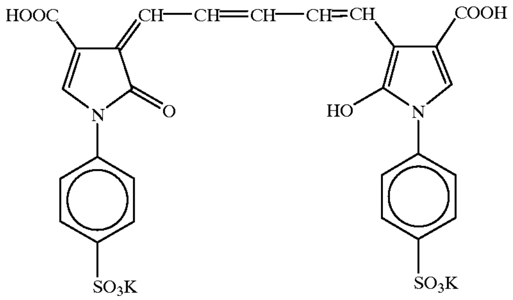

Compound J:

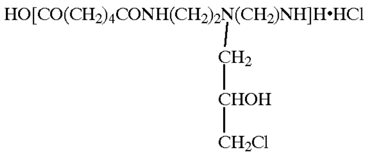

Core-shell Type Vinylidene Chloride Copolymer (1):

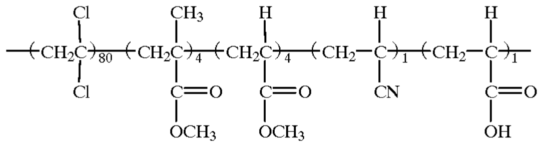

VDC MMA MA AN AA

Core: VDC/MMA/MA (80 wt %)
Shell: VDC/AN/AA (20 wt %)
Average particle size: 70 μm Compound M:

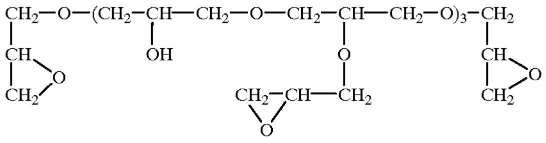

The coating method and the drying conditions were as follows.

Coating Method:

On the emulsion surface side of the support having undercoat layers provided thereon, an emulsion layer, an emulsion protective lower layer and an emulsion protective upper layer were simultaneously coated one on another in sequence from the side nearer to the support while keeping at 35° C. and while adding a hardening agent solution by a slide hopper method, and the coated sample was passed through a cold blast set zone (5° C.). Thereafter, on the side opposite the emulsion surface, an electrically conductive layer and a back layer were similarly simultaneously coated one on another in sequence from the side nearer to the support while adding a hardening agent solution by the slide hopper method, and the coated sample was passed through a cold blast set zone (5° C.). After passing through respective set zones, the coating solution exhibited satisfactory setting property. Subsequently, both surfaces were simultaneously dried in the drying zone under the following drying conditions. After coating on the back surface side, the coated sample was transported without coming into contact with a roller and others at all until winding up. At this time, the coating rate was 120 m/min.

Drying Condition:

After setting, the coated sample was dried by drying air at 30° C. until the weight ratio of water/gelatin became 800% and then by drying air at 35° C. and 30% to give the ratio of from 200 to 800%. The blowing of air was continued and 30 seconds after the time when the surface temperature reached 34° C. (regarded as completion of the drying), the coated sample was dried by air at 48° C. and 2% for one minute. At this time, the drying time of from the initiation of drying until the water/gelatin ratio reached 800% was 50 seconds, the drying time until the ratio reached from 800 to 200% was 35 seconds and the drying time of from the ratio of 200% until completion of the drying was 5 seconds.

The thus-obtained light-sensitive material was wound up at 23° C. and 40%, cut under the same environment, subjected to humidity conditioning at 40° C. and 10% for 8 hours in a barrier bag of which humidity was conditioned for 6 hours, and then sealed together with a cardboard of which humidity was conditioned at 23° C. and 40% for 2 hours, to prepare a sample.

The humidity in the barrier bag was measured and found to be 40%.

Samples shown in Table 17 were prepared as described above.

TABLE 17

| Sample No. | Solid Dispersion of Hydrazine Compound | Remarks |
|---|---|---|
| 2-1 | K-1 | Comparison |
| 2-2 | K-2 | Comparison |
| 2-3 | K-3 | Comparison |
| 2-4 | K-4 | Comparison |
| 2-5 | K-5 | Comparison |
| 2-6 | K-6 | Comparison |
| 2-7 | K-7 | Comparison |
| 2-8 | K-16 | Invention |
| 2-9 | K-17 | Invention |
| 2-10 | K-18 | Invention |
| 2-11 | K-19 | Invention |
| 2-12 | K-20 | Invention |
| 2-13 | K-21 | Invention |
| 2-14 | K-22 | Invention |
| 2-15 | K-23 | Invention |

Evaluation:

The above-described samples each was exposed through a step wedge in a printer P-627FM manufactured by Dainippon Screen Mfg. Co., Ltd. Then, the samples each was developed with Developer A described in Example 2 in an automatic developing machine FG-680AG manufactured by Fuji Photo Film Co., Ltd, at 38° C. for 15 seconds, and subjected to fixing (same as in Example 2), water washing and drying. In the processing, the developer and the fixing solution were replenished each in an amount of 100 ml per $m^2$ of the sample.

Evaluation of the contrast, the dependency of sensitivity on pH of the developer and the aging stability of the light-sensitive material was performed in the same manner as in Example 2.

The results obtained are shown in Table 18.

TABLE 18

| Sample No. | γ | Dependency on pH of Developer ($\Delta S_{1.5}$) | Aging Stability of Light-Sensitive Material ($\Delta S_{1.5}$) | Remarks |
|---|---|---|---|---|
| 2-1 | 8 | 0.12 | 0.03 | Comparison |
| 2-2 | 11 | 0.27 | 0.11 | Comparison |
| 2-3 | 11 | 0.24 | 0.09 | Comparison |
| 2-4 | 10 | 0.14 | 0.07 | Comparison |
| 2-5 | 12 | 0.15 | 0.10 | Comparison |
| 2-6 | 11 | 0.13 | 0.08 | Comparison |
| 2-7 | 12 | 0.16 | 0.07 | Comparison |
| 2-8 | 18 | 0.06 | 0.01 | Invention |
| 2-9 | 18 | 0.06 | 0.01 | Invention |
| 2-10 | 18 | 0.07 | 0.01 | Invention |
| 2-11 | 16 | 0.09 | 0.02 | Invention |
| 2-12 | 18 | 0.06 | 0.01 | Invention |
| 2-13 | 16 | 0.07 | 0.02 | Invention |
| 2-14 | 17 | 0.09 | 0.02 | Invention |
| 2-15 | 19 | 0.04 | 0.01 | Invention |

Results:

Only when the hydrazine compound of the present invention was used as a nucleating agent, a light-sensitive material for dot-to-dot work in a bright room, having ultrahigh contrast, high processing stability and excellent storage stability of the light-sensitive material could be obtained with a developer having a low pH.

EXAMPLE 7

In Examples 2, 3, 4, 5 and 6, even when Developer D or Developer E having the following composition was used in place of Developer A and Fixing Solution B having the following composition was used in place of Fixing Solution A, a light-sensitive material having ultrahigh contrast, high processing stability and excellent storage stability of the light-sensitive material could be obtained with a developer having a low pH, only when the hydrazine compound of the present invention was used as a nucleating agent, similarly to Examples 2, 3, 4, 5 and 6. In examining the dependency of the photographic property on pH of the developer, each developers reduced in the pH by 0.5 with acetic acid or increased in the pH by 0.5 with sodium hydroxide were used.

Developer D:

| | |
|---|---|
| Potassium hydroxide | 40.0 g |
| Diethylenetriaminepentaacetic acid | 2.0 g |
| Potassium carbonate | 60.0 g |
| Sodium metabisulfite | 70.0 g |
| Potassium bromide | 7.0 g |
| Hydroquinone | 40.0 g |
| 5-Methylbenzotriazole | 0.35 g |
| 4-Hydroxymethyl-4-methyl-1-phenyl-3-pyrazolidone | 1.50 g |
| Sodium 2-mercaptobenzimidazole-5-sulfonate | 0.30 g |
| Sodium 3-(5-mercaptotetrazol-1-yl)-benzenesulfonate | 0.10 g |
| Sodium erythorbate | 6.0 g |
| Diethylene glycol | 5.0 g |
| Water to make | 1 l |

pH was adjusted by adding potassium hydroxide to 10.65.

Developer E:

A developer stored as a solid was formed into a use solution by adding water to make 10 l.

The solid developer was produced by packing developer components in the form of solid, corresponding to 10 l portion as a use solution, in a container (average wall thickness: 500 μm, partially: from 200 to 1,000 μm) made of a high density polyethylene. The respective components were first mixed and then packed in the container.

The composition of the developer as a 10 l use solution and the shapes of raw materials are shown in Table 19.

TABLE 19

| Developer No. | Shape of Raw Material | |
|---|---|---|
| Sodium hydroxide (99.5%) (purity in the parenthesis) | beads | 115 g |
| Potassium sulfite | raw powder | 718 g |
| Sodium sulfite | raw powder | 350 g |
| Diethylenetriaminepentaacetic acid | | 20 g |
| 5-Methylbenzotriazole | | 3.5 g |
| Sodium 2-mercaptobenz-imidazole-5-sulfonate | | 3.0 g |
| Sodium 3-(5-mercaptotetrazol-1-yl)-benzenesulfonate | briquetted collectively | 1.0 g |
| Potassium bromide | | 66 g |
| 4-Hydroxymethyl-4-methyl-1-phenyl-3-pyrazolidone | | 15 g |
| Sodium erythorbate | | 60 g |
| Potassium carbonate | raw powder | 620 g |
| Hydroquinone | briquet | 400 g |
| Total weight | | 2,336 g |
| Alkali wt % | | 4.9% |
| pH | | 10.6 |

With respect to the shape of raw materials, the raw powder was a general industrial product as it is and the beads and the pellets of alkali metal salt were commercially available products.

The raw materials in the shape of a briquet each was compressed under pressure using a briquetting machine to have an undefined Rugby ball form having a length of approximately from 4 to 6 mm, and the briquet was crushed and used. With respect to components in a small amount, respective components were blended and then briquetted.

Fixing Solution B:

The following solid agent and liquid agent were formed into a use solution by adding water to make 10 l. The fixing solution used was obtained by packing the following formulation, including both the solid agent part and the liquid agent part, in a container (average wall thickness: 500 μm, width: from 200 to 1,000 μm) made of a high density polyethylene. After dissolving, the amount of solution was 10 l and the pH was 4.85.

Solid agent part:

| | |
|---|---|
| Ammonium thiosulfate | 1,200 g |
| Sodium thiosulfate | 150 g |
| Sodium acetate | 400 g |
| Sodium metabisulfite | 200 g |

Liquid agent part:

| | |
|---|---|
| Aluminum sulfate (27%) | 300 g |
| Sulfuric acid (75%) | 30 g |
| Sodium gluconate | 20 g |
| EDTA | 0.3 g |
| Citric acid | 40 g |

The solid agent part was packed after mixing.

EXAMPLE 8

A light-sensitive material was prepared in the same manner as in Example 6, except that the hydrazine compound powder shown in Table 20 was dissolved in methanol and then added to the coating solution. The samples each was developed in the same manner as in Example 6 and evaluated on the contrast and the dependency of sensitivity on pH of the developer.

The results obtained are shown in Table 20.

TABLE 20

| Sample No. | Hydrazine Compound | γ | Dependency on pH of Developer ($\Delta S_{1.5}$) | Remarks |
|---|---|---|---|---|
| 3-1 | Comparative Compound 1 | 12 | 0.25 | Comparison |
| 3-2 | Comparative Compound 2 | 13 | 0.27 | Comparison |
| 3-3 | Comparative Compound 3 | 11 | 0.18 | Comparison |
| 3-4 | Comparative Compound 4 | 13 | 0.20 | Comparison |
| 3-5 | 4b | 16 | 0.05 | Invention |
| 3-6 | 17b | 17 | 0.04 | Invention |
| 3-7 | 21b | 16 | 0.04 | Invention |
| 3-8 | 6b | 17 | 0.05 | Invention |
| 3-9 | 41c | 19 | 0.02 | Invention |
| 3-10 | 4c | 20 | 0.07 | Invention |
| 3-11 | 17c | 19 | 0.08 | Invention |
| 3-12 | 21c | 21 | 0.07 | Invention |
| 3-13 | 6c | 21 | 0.08 | Invention |
| 3-14 | 41b | 23 | 0.05 | Invention |

Results:

Similarly to Example 6, only when the hydrazine compound of the present invention was used as a nucleating agent, a light-sensitive material having ultrahigh contrast and high processing stability could be obtained with a developer having a low pH.

While the invention has been described in detail and with reference to specific embodiments thereof, it will be apparent to one skilled in the art that various changes and modifications can be made therein without departing from the spirit and scope thereof.

What is claimed is:

1. A hydrazine compound represented by the following formula (I):

$$Ar_1—NH—NH—G_1—R_1 \quad (I)$$

wherein $Ar_1$ represents an aromatic group; $G_1$ represents a carbonyl group, a sulfonyl group, a sulfoxy group, a phosphoryl group, an oxalyl group or an iminomethylene group; $R_1$ represents a hydrogen atom or a blocking group; and at least one of $Ar_1$ and $R_1$ has a group represented by the following formula (II):

(II)

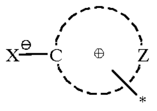

wherein * represents a bond for connecting directly or through a linking group to $Ar_1$ or $R_1$; Z represents a nonmetallic atom group capable of forming a 5- or 6-membered unsaturated heterocyclic ring having a conjugated positive charge; and $X^-$ represents $—O^-$, $—S^-$ or $—N^-—R_2$, wherein $R_2$ represents an alkyl group, an alkenyl group, an alkynyl group, an aryl group or a heterocyclic group.

2. The hydrazine compound of claim 1, which is represented by the following formulae (III-A) or (III-B):

(III-A)

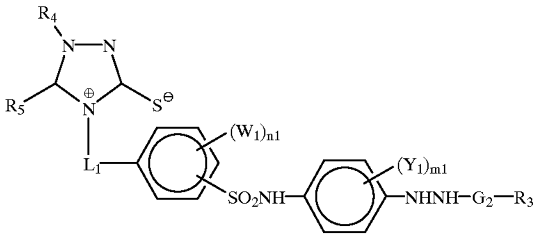

(III-B)

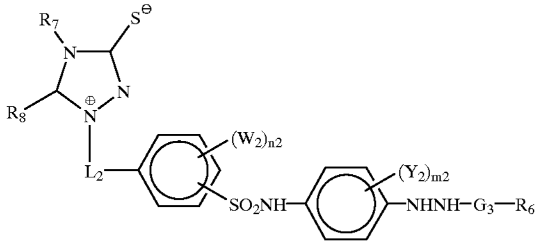

wherein $L_1$ and $L_2$ each represents a linking group; $G_2$ and $G_3$ each represents a carbonyl group, a sulfonyl group, a sulfoxy group, a phosphoryl group, an oxalyl group or an iminomethylene group; $R_3$ and $R_6$ each represents a hydrogen atom or a blocking group; $W_1$ and $W_2$ each represents a halogen atom or a substituent which comprises a carbon, oxygen, nitrogen, or sulfur atom and which bonds to the benzene ring at said carbon, oxygen, nitrogen or sulfur atom; $Y_1$ and $Y_2$ each represents a halogen atom or a substituent which comprises a carbon, oxygen, nitrogen, or sulfur atom and which bonds to the benzene ring at said carbon, oxygen, nitrogen or sulfur atom; $n_1$, $n_2$, $m_1$ and $m_2$ each represents an integer from 0 to 4; $R_4$ and $R_7$ each represents a halogen atom or a substituent which comprises a carbon, oxygen, nitrogen, or sulfur atom and which bonds to the ring at said carbon, oxygen, nitrogen or sulfur atom; and $R_5$ and $R_8$ each represents a hydrogen atom, a halogen atom or a substituent which comprises a carbon, oxygen, nitrogen, or sulfur atom and which bonds to the ring at said carbon, oxygen, nitrogen or sulfur atom.

3. A silver halide photographic light-sensitive material comprising a hydrazine compound represented by the following formula (I):

$$Ar_1—NH—NH—G_1—R_1 \quad (I)$$

wherein $Ar_1$ represents an aromatic group; $G_1$ represents a carbonyl group, a sulfonyl group, a sulfoxy group, a phosphoryl group, an oxalyl group or an iminomethylene group; $R_1$ represents a hydrogen atom or a blocking group; and at least one of $Ar_1$ and $R_1$ has a group represented by the following formula (II):

(II)

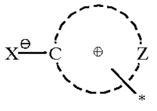

wherein * represents a bond for connecting directly or through a linking group to $Ar_1$ or $R_1$; Z represents a nonmetallic atom group capable of forming a 5- or 6-membered unsaturated heterocyclic ring having a conjugated positive charge; and $X^-$ represents $—O^-$, $—S^-$ or $—N^-—R_2$, wherein $R_2$ represents an alkyl group, an alkenyl group, an alkynyl group, an aryl group or a heterocyclic group.

4. The silver halide photographic light-sensitive material according to claim 3, which contains the compound of formula (I) in an amount of from $1\times10^{-6}$ to $1\times10^{-2}$ mol per mol of silver halide.

5. The silver halide photographic light-sensitive material according to claim 3, which further comprises a nucleation accelerator represented by the following formulae (IV), (V), (VI) or (VII):

(IV)

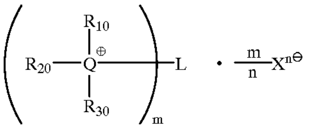

wherein $R_{10}$, $R_{20}$ and $R_{30}$ each represents an alkyl group, a cycloalkyl group, an aralkyl group, an aryl group, an alkenyl group, a cycloalkenyl group, an alkynyl group or a heterocyclic group; Q represents a nitrogen atom or a phosphorus atom; L represents an m-valent organic group bonded to $Q^+$ through the carbon atom thereof, wherein m represents an integer of from 1 to 4; and $X^{n-}$ represents an n-valent counter anion, wherein n represents an integer of from 1 to 3, provided that when $R_{10}$, $R_{20}$, $R_{30}$ or L has an anion group on the substituent thereof and forms an inner salt with $Q^+$, $X^{n-}$ can be omitted;

(V)

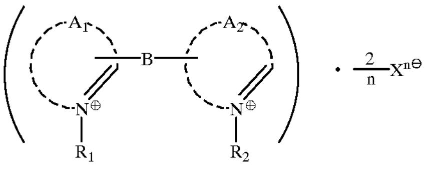

(VI)

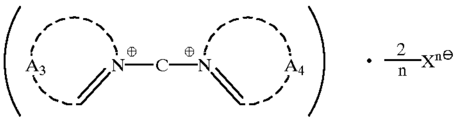

wherein $A_1$, $A_2$, $A_3$ and $A_4$ each represents an organic residue for completing a substituted or unsubstituted unsaturated heterocyclic ring containing the quaternized nitrogen atom; B and C each represents a divalent linking group comprising at least one of alkylene, arylene, alkenylene, alkynylene, $—SO_2—$, —SO—, —O—, —S—, $—N(R'_N)—$ (wherein $R'_N$ represents a hydrogen atom, an alkyl group, an aryl group or an aralkyl group), —C=O— and —P=O—; $R_1$ and $R_2$ each represents an alkyl group or an aralkyl group; and $X^{n-}$ represents an n-valent counter anion, wherein n represents an integer of from 1 to 3, provided that when an inner salt can be formed, $X^{n-}$ can be omitted;

(VII)

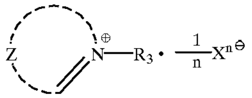

wherein Z represents an organic residue for completing a substituted or unsubstituted unsaturated heterocyclic ring containing the quaternized nitrogen atom; $R_3$ represents an alkyl group or an aralkyl group; and $X^{n-}$ represents an n-valent counter anion, wherein n represents an integer of from 1 to 3, provided that when an inner salt can be formed, $X^{n-}$ can be omitted.

6. The silver halide photographic light-sensitive material according to claim 5, which contains the nucleation accelerator in an amount of from $1\times10^{-6}$ to $2\times10^{-2}$ mol per mol of silver halide.

7. The silver halide photographic light-sensitive material according to claim 3, which further comprises a metal compound selected from a group consisting of a rhodium compound, a ruthenium compound, a rhenium compound and a chromium compound.

8. The silver halide photographic light-sensitive material according to claim 7, wherein the metal compound is represented by the following formula:

$$[M(NY)_m L_{6-m}]^n$$

wherein M is a heavy metal selected from Ir, Ru, Rh, Re and Cr; L is a cross-linking ligand; Y is an oxygen or sulfur atom; m is 0, 1 or 2; and n is 0, −1, −2 or −3.

* * * * *